(12) United States Patent
Siepmann et al.

(10) Patent No.: US 8,088,414 B2
(45) Date of Patent: Jan. 3, 2012

(54) LATEX OR PSEUDOLATEX COMPOSITIONS, COATINGS AND COATING PROCESSES

(75) Inventors: Juergen Siepmann, Lille (FR); Florence Siepmann, Lille (FR); Brian A. C. Carlin, Pittsgrove, NJ (US); Jian-Xin Li, North Brunswick, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 11/669,630

(22) Filed: Jan. 31, 2007

(65) Prior Publication Data

US 2007/0184102 A1 Aug. 9, 2007

Related U.S. Application Data

(60) Provisional application No. 60/870,012, filed on Dec. 14, 2006, provisional application No. 60/790,418, filed on Apr. 7, 2006, provisional application No. 60/771,199, filed on Feb. 7, 2006.

(51) Int. Cl.
*A61K 9/50* (2006.01)
(52) U.S. Cl. .................................................... 424/495
(58) Field of Classification Search .................. None
See application file for complete search history.

(56) References Cited

U.S. PATENT DOCUMENTS

| | | | |
|---|---|---|---|
| 4,330,338 A | 5/1982 | Banker | |
| 4,975,284 A * | 12/1990 | Stead et al. | 424/497 |
| 5,370,880 A | 12/1994 | Jones et al. | |
| 6,129,933 A | 10/2000 | Oshlack et al. | |
| 6,274,173 B1 * | 8/2001 | Sachs et al. | 424/480 |
| 2002/0155156 A1 | 10/2002 | Mulye | |
| 2002/0192285 A1 | 12/2002 | Mulye | |
| 2003/0107149 A1 | 6/2003 | Yang et al. | |
| 2003/0175342 A1* | 9/2003 | Kolter et al. | 424/468 |
| 2005/0196444 A1* | 9/2005 | Kolter et al. | 424/472 |
| 2005/0220878 A1* | 10/2005 | Fegely et al. | 424/473 |
| 2006/0269605 A1 | 11/2006 | Lizio et al. | |
| 2007/0184198 A1 | 8/2007 | Li et al. | |

FOREIGN PATENT DOCUMENTS

| | | |
|---|---|---|
| EP | 0315414 A1 | 5/1989 |
| EP | 0425023 A2 | 5/1991 |
| EP | 1430889 A | 6/2004 |
| JP | 1997-194347 | 7/1997 |
| WO | WO-0132152 A1 | 5/2001 |
| WO | WO-02085335 A1 | 10/2002 |

OTHER PUBLICATIONS

BASF Press Release, "BASF Extends Kollicoat IR Range," Dec. 13, 2004.
Lange, Ronald F.M. et al., "The Development of an Instant Release Tablet Coating," International Pharmaceutical Excipients Council Europe News, May 2004.
Rohera, Ghagwan D. and Parikh, Nilesh H., "Influence of Type and Level of Water-Soluble Additives on Drug Release and Surface and Mechnical Properties of Surelease(R) Films," Pharmaceutical Development and Technology, 2002, pp. 421-432, vol. 7, No. 4.
Kollicoat(R) IR, Technical Information Bulletin, Jul. 2006.
Kollicoat(R) SR 30 D, Technical Information Bulletin, Aug. 2005.
Mies, S. et al., "Correlation of Drug Permeation Through Isolated Films and Coated Dosage Forms Based on Kollicoat(R) SR 30 D/IR," AAPS Annual Meeting and Exposition, Nov. 7-11, 2004, Baltimore, Maryland.
Kolter, K. and Ruchatz, F., "Kollicoat(R) SR 30 D—A New Sustained Release Excipient," The 26th International Symposium on Controlled Release of Bioactive Materials, Jun. 20-25, 1999, Boston, MA.
Bordaweker, M., Zia, H., and Quadir, A., "Release Characteristics of Selected Drugs with a Newly Developed Polyvinyl Acetate Dispersion," 31st International Symposium on Controlled Release of Bioactive Material, Jun. 12-16, 2004, Honolulu, Hawaii.
Meyer, K. and Kolter, K., "Reliability of Drug Release from an Innovative Single Unit Kollicoat(R) Drug Delivery System," 31st International Symposium on Controlled Release of Bioactive Materials, Jun. 12-16, 2004, Honolulu, Hawaii.
Postel, M. et al., Innovative Tilidine-Naloxone Sustained Release Drug Delivery Systems based on Kollicoat(R) Polymers, Poster, May 21, 2004.

\* cited by examiner

*Primary Examiner* — Michael G Hartley
*Assistant Examiner* — Paul Dickinson

(57) ABSTRACT

A composition comprising: (i) at least one latex or pseudolatex water insoluble film former, (ii) at least one permeation enhancing agent and, optionally, (iii) one or more plasticizers. The present invention is also directed to substrates coated with the composition of the invention, films made from the composition and methods for making and using such compositions, coated substrates and films.

36 Claims, 45 Drawing Sheets

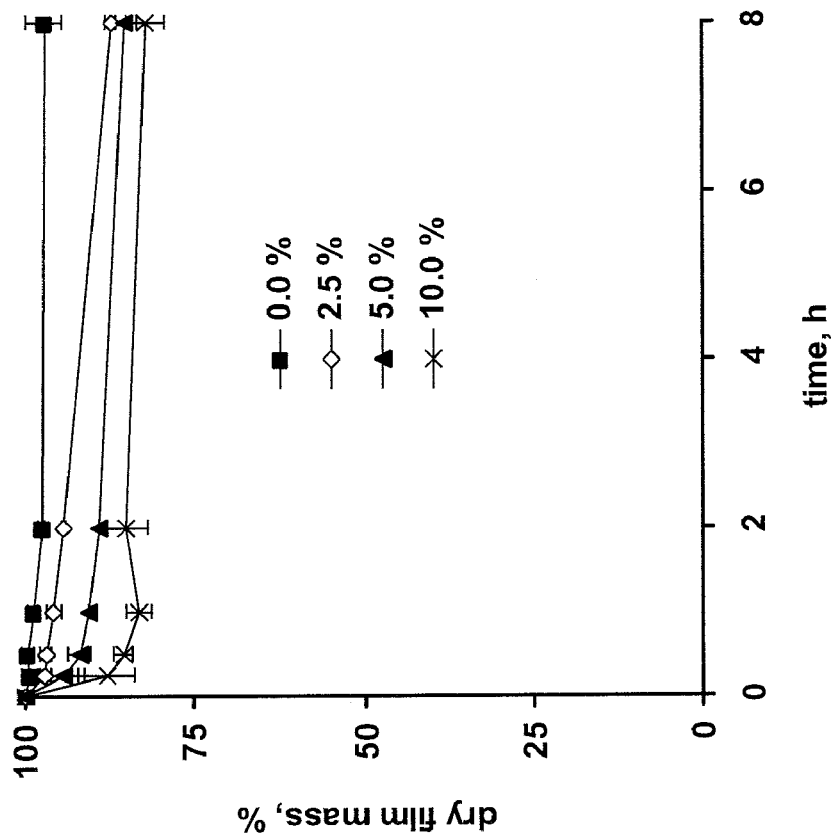
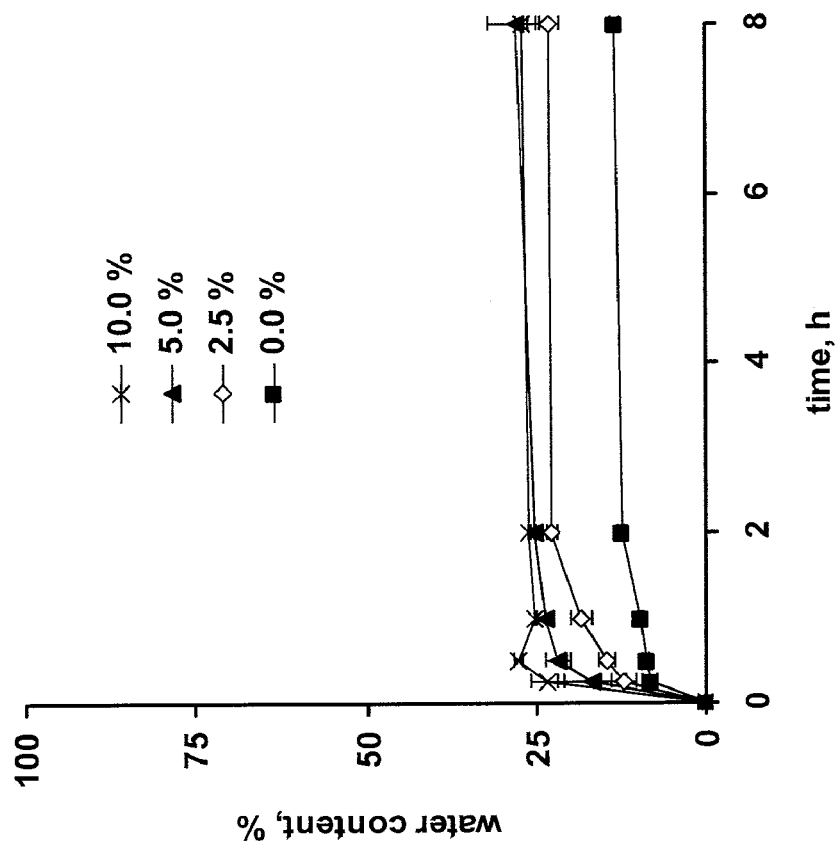
Figure 1(a)
Figure 1(b)

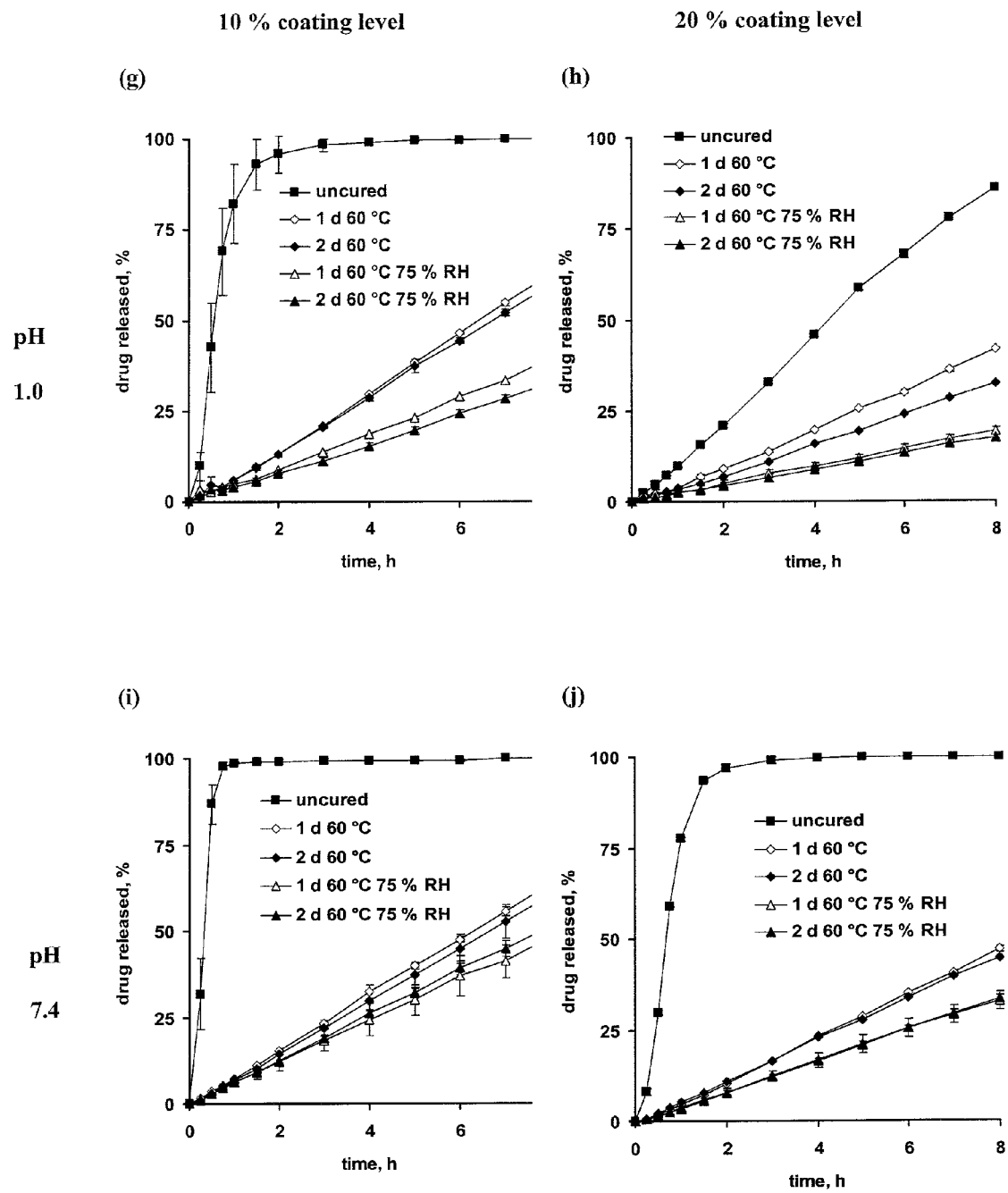

(o)

(p)

(q)

(r)

0.1 M HCl

Demineralized water

| curing \ storage | RT & ambient RH | 40 °C & 75 % RH |
|---|---|---|
| 1 d 60 °C |  |  |
| 2 d 60 °C |  |  |
| 1 d 60 °C & 75 % RH |  |  |
| 2 d 60 °C & 75 % RH |  |  |

US 8,088,414 B2

LATEX OR PSEUDOLATEX COMPOSITIONS, COATINGS AND COATING PROCESSES

BACKGROUND OF THE INVENTION

1. Field of the Invention

The present invention relates to a latex or pseudolatex composition. The present invention also relates to substrates coated with the latex or pseudolatex composition, films made from the latex or pseudolatex composition and methods for making and using such compositions, coated substrates and films.

2. Brief Description of the Related Art

To provide compositions to modulate the release of drug from films or substrates coated with films of latex or pseudolatex water insoluble film formers. The barrier efficiency of such pseudolatex or latex films can be so high as to limit the coating loading to levels low enough to pose manufacturing reproducibility problems.

Addition of compatible permeation enhancing agents increases the permeability of pseudolatex or latex films without compromising on loading or choice of plasticizer. Based on the obtained knowledge the optimization of, for example, Aquacoat ECD-coated dosage forms can significantly be facilitated. Desired membrane properties (in particular drug permeabilities) can easily be adjusted.

Polymeric film coatings are frequently used to control the release rate of a drug out of a pharmaceutical dosage form. Showing good oral biocompatibility and film forming properties, ethylcellulose is a suitable polymer for this purpose. However, continuous ethylcellulose films are poorly permeable for most drugs Siepmann, J. et al (1999) *J. Controlled Release* 60: 379-389, resulting in low release rates. To overcome this restriction, hydroxypropyl methylcellulose (HPMC) has been proposed as a pore former accelerating drug release, Frohoff-Huelsmann, M. et al (1999) *Int. J. Pharm.* 177: 69-82. However, relatively high quantities are required and the presence of HPMC in the coating dispersions causes coagulation.

SUMMARY OF THE INVENTION

The present invention is directed to a composition comprising: (i) at least one latex or pseudolatex water insoluble film former, (ii) at least one permeation enhancing agent and, optionally, (iii) one or more plasticizers. The present invention is also directed to substrates coated with the composition of the invention, films made from the composition and methods for making and using such compositions, coated substrates and films.

BRIEF DESCRIPTION OF THE DRAWINGS

FIGS. 1(a)-1(b) show the effect of the Kollicoat® IR content on: 1(a) the water uptake, and 1(b) dry weight loss behavior of thin polymeric films in 0.1M HCl for mixtures of Kollicoat® IR with Aquacoat® ECD30.

FIG. 16(g) shows the release of theophylline from cured pellets coated with ethylcellulose containing 5% by weight of carrageenan upon exposure to 0.1M HCl at a 10% (w/w) coating level.

FIG. 16(h) shows the release of theophylline from cured pellets coated with ethylcellulose containing 5% by weight of carrageenan upon exposure to 0.1M HCl at a 20% (w/w) coating level.

FIG. 16(i) shows the release of theophylline from cured pellets coated with ethylcellulose containing 5% by weight of carrageenan upon exposure to phosphate buffer pH 7.4 at a 10% (w/w) coating level.

FIG. 16(j) shows the release of theophylline from cured pellets coated with ethylcellulose containing 5% by weight of carrageenan upon exposure to phosphate buffer pH 7.4 at a 20% (w/w) coating level.

DETAILED DESCRIPTION OF THE INVENTION

Figure 2:
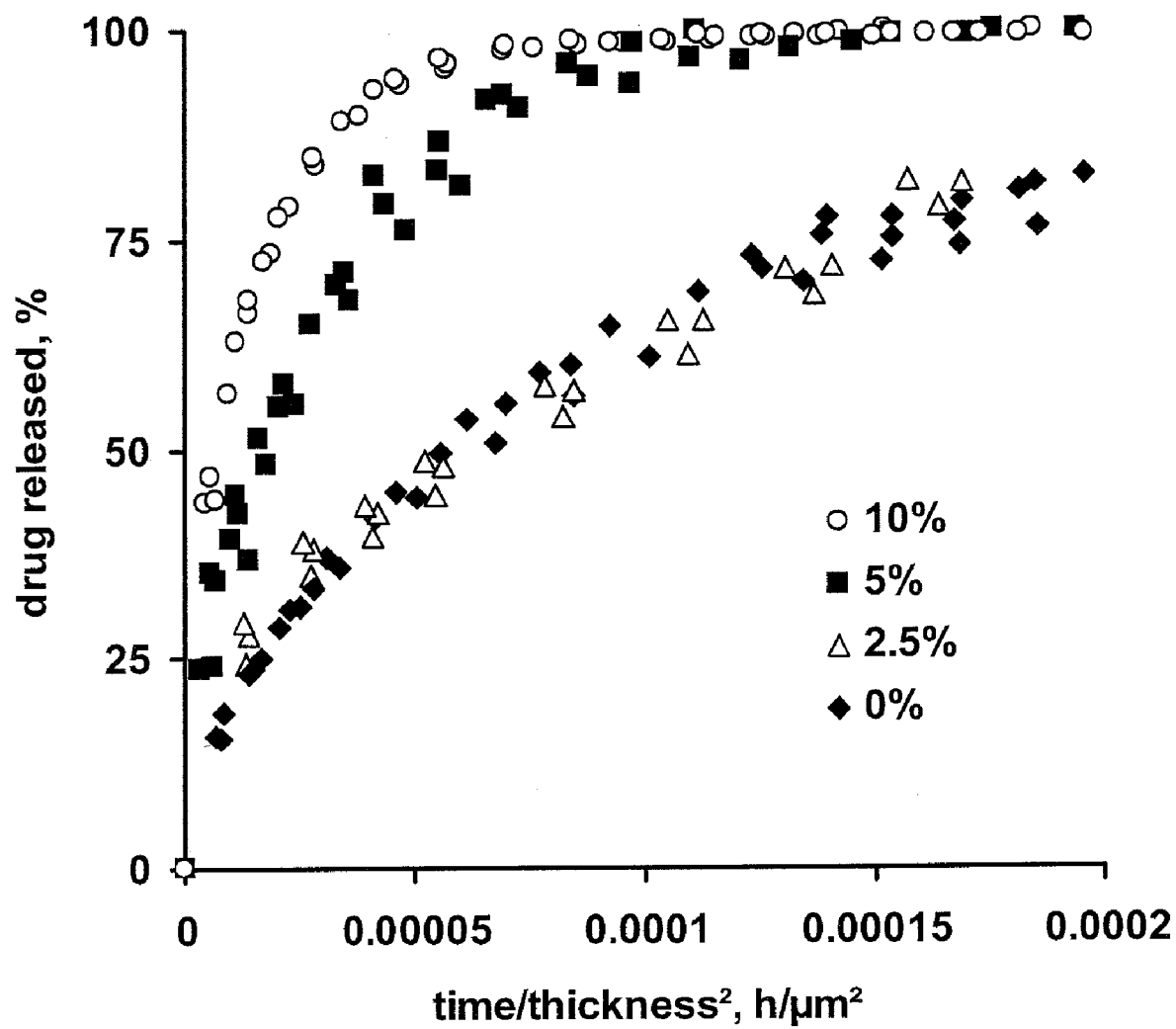
FIG. 2 shows the effect of the Kollicoat® IR content on theophylline release from thin polymeric films in 0.1M HCl for mixtures of Kollicoat® IR with Aquacoat® ECD30

This invention relates to compositions that allow modulation of release of drug from films or substrates coated with films of latex or pseudolatex water insoluble film formers. The addition of permeation enhancing agents to the latex or pseudolatex water insoluble film formers offers a method for the modulation of the release rate of a drug.

As used herein, "latex or pseudolatex water insoluble film formers" refers to that group of water insoluble polymers that, when finely divided in aqueous dispersion, are capable of coalescing to form a film or film coating.

Pseudolatexes are prepared by emulsifying a preformed polymer. For example, pseudolatexes of ethylcellulose are prepared by dissolving the polymer in a suitable solvent, and introducing the organic phase into water to form an emulsion, using an emulsifier, such as sodium lauryl sulfate, and a stabilizer such as cetyl alcohol After homogenization, the solvent is removed by vacuum distillation, leaving about a 30% solids dispersion of ethylcellulose in water.

A latex is prepare by polymerization of a monomer or monomer blend which is usually emulsified in an aqueous medium of anionic or non-ionic surfactants. The process requires the addition of initiators that function by free radical, anionic or cationic polymerization mechanisms. The polymer latex is typically submicron in particle size.

Latex or pseudolatex film formers in accordance with the present invention may include, for example, dispersions of insoluble copolymers such as ethylcellulose, acrylate and methacrylate copolymers, water insoluble cellulosics, cellulose acetate, and cellulose acetate phthalate.

The latex or pseudolatex water insoluble film former may be present in amounts of 50% or more by weight, 60% or more by weight, 65% or more by weight, 70% or more by weight, 75% or more by weight, 85% or more by weight, or 90% or more by weight, all on a dry basis.

Films are applied to medicinal drug preparations in order to control the release rate of drugs (the active ingredients of medicinal drug products). Conventionally, a polymeric substance which is the film base composition is dissolved in an organic solvent and is supplied for the process of film coating. However, due to environmental and safety concerns, aqueous film coating compositions have come into use in order to avoid the use of organic solvents.

One aqueous film coating composition that can control the rate of release of drugs and that has strong moisture-proofing capacity is an ethylcellulose dispersion, which is sold on the market as Aquacoat® ECD by FMC Corporation and monographed in the United States National Formulary and Handbook of Japanese Excipients as Aqueous Ethylcellulose Dispersion.

However, as background, the barrier properties of the pseudolatex or latex film depend on the film thickness or loading, the amount and type of plasticizer, and the degree of coalescence of the pseudolatex or latex particles in the film, which is in turn time, temperature and humidity dependent. Optimisation and scale-up of aqueous pseudolatex or latex film coating processes can be complex. Partially coalesced films will give faster release rates but the release rates will not be stable with time as coalescence may still proceed albeit slowly under normal storage conditions. If the fully coalesced barrier properties are excessive then the thickness or the loading can be reduced but this poses problems of inconsistent release rates due to lesser precision of application of low coating loadings or to greater incidence or impact of defects on thin films. Changing the plasticizer can alter the release rate but this may also affect the mechanical properties of the film if the level or type plasticizer giving the fastest release is not optimal in terms of film properties. The limited number of approved plasticizers may also pose regulatory problems in certain jurisdictions as very few are globally accepted. Simple addition of water soluble or hydrophilic material to increase release rates may give a disproportionate and catastrophic increase in release rate due to destabilisation of the pseudolatex or latex suspension preventing subsequent coalescence of the film. This effect is exploited by the addition of water soluble polymers such as hydroxypropylmethylcellulose (HPMC) to dispersions of Aquacoat® ECD in order to take advantage of the moisture barrier and contour-following properties of pseudolatex or latex coatings in immediate-release applications. For controlled, sustained or modified release applications, having solved the complex optimization the formulator may be faced with an all or nothing release behaviour posing great problems of reproducibility and scale-up.

This invention was developed for the purpose of solving the problems described above and its object is to provide compositions of compatible permeation enhancing agents which increase the release rate of drug from coalesced pseudolatex or latex films in a concentration dependent manner thus affording a method of release rate modulation which does not necessitate reduction in film thickness or loading nor interfere with choice of plasticizer. It is essential that the latex or pseudolatex particles are not destabilized (e.g., are not aggregated, flocculated or coagulated) in the dispersion prior to or during spraying as this disrupts the mechanism of film formation which requires close packing of the particles on the substrate surface followed by sintering or coalescing into a coherent film. Surprisingly despite the widely reported incompatibility of pseudolatex or latex dispersions to the addition of polymers a few materials have been identified which do not cause flocculation, aggregation or coagulation of the pseudolatex or latex dispersion nor cause undesirable interference with pseudolatex or latex film formation.

Certain permeation enhancing agents can increase the release rate of drugs from pseudolatex or latex films and coatings without destabilizing the pseudolatex or latex dispersion and destroying the barrier properties of the pseudolatex or latex film or coating. As used herein, "permeation enhancing agent" refers to that group of materials such as polymers, salts and sugars that do not destabilize aqueous dispersions of the latex or pseudolatex water insoluble film former. Examples of such permeation enhancing agents include but are not limited to carrageenan (e.g., kappa, lambda, kappa-2 and iota), propylene glycol alginate, starch, sucrose, lactose, mannitol, sorbitol, glucose, poly(ethyl acrylate, methyl methacrylate) (Eudragit® NE 30D), polymethacrylates, methacrylic acid copolymers, polyvinyl acetate, phosphate salts, polyethylene glycols, polyvinylpyrrolidone, polyvinylalcohol-polyethylene glycol copolymer (Kollicoat® IR, BASF), polyvinyl alcohol, microcrystalline cellulose, microcrystalline cellulose-carrageenan, cellulose acetate phthalate, sodium alginate, sodium/calcium alginate, magnesium alginate, ammonium alginate, sodium starch glycolate, croscarmellose, starch, sucrose, lactose, mannitol, sorbitol, glucose, calcium hydrogen phosphate, disodium hydrogen phosphate. Preferred permeation enhancing agents of the present invention include propylene glycol alginate, starch, carrageenan or polyvinyl alcohol-polyethylene glycol copolymer (marketed by BASF as Kollicoat® IR). The permeation enhancing agent can be present at levels less than 50% relative to the pseudolatex or latex particles. The higher the level, the greater the water uptake of the pseudolatex or latex film or coating, and the higher the release rate of drug.

The permeation enhancing agent may be present in an amount of less than or equal to 30% by weight of the latex or pseudolatex composition, and, optionally, may comprise less than or equal to 25% by weight, 20% by weight, 15% by weight, 10% by weight, 5% by weight, 3% by weight or 1% by weight of said latex or pseudolatex composition. The latex or pseudolatex composition preferably includes at least 0.5% by weight of the permeation enhancing agent.

In this invention, drugs refer to substances that are used for the treatment, prevention and diagnosis of diseases of humans and animals. For example, they can include the following substances. Specifically, they can include anti-epileptic agents (examples: phenytoin, acetylpheneturide, trimethadione, phenobarbital, primidone, etc.), antipyretic-analgesic-anti-inflammatory agents (examples: acetaminophen, phenyl acetylglycine methyl amide, mefenamic acid, diclofenac sodium, floctafenine, aspirin, aspirin aluminum, ethenzamide, oxyphenbutazone, sulpyrin, phenylbutazone, ibuprofen, alclofenac, naproxen, ketoprofen, tinoridine hydrochloride, benzydamine hydrochloride, tialamide hydrochloride, indomethacin, piroxicam, salicylamide, etc.), antivertigo agents (examples: dimenhydrinate, meclizine hydrochloride, diphentoin hydrochloride, etc.), narcotics (examples: opium alkaloid hydrochlorides, ethylmorphine hydrochloride, codeine phosphate, dihydrocodeine phosphate, oxymethebanol, etc.), agents for psychological use (examples: chlorpromazine hydrochloride, levomepromazine maleate, perazine maleate, propericiazine, perphenazine, chlorprothixene, haloperidol, diazepam, oxazepam. oxazolam, mexazolam, alprazolam, zotepine, etc.), skeletal muscle relaxants (examples: chlorzoxazone, chlorphenesin carbamate, chlormezanone, pridinol mesylate, eperisone hydrochloride, etc.), autonomic nerve agents (examples: betanecol hydrochloride, neostigmine bromide, pyridostigmine bromide, etc.), antispasmodic agents (examples: atropine sulfate, butropium bromide, butylscopolammonium bromide, propantheline bromide, papaverine hydrochloride, etc.), antiparkinsonian agents (examples: biperiden hydrochloride, trihexyphenidyl hydrochloride, amantadine hydrochloride, levodopa, etc.), ophthalmological agents (examples: dichlorophenamide, metazolamide, etc.), antihistaminic agents (examples: diphenhydramine hydrochloride, di-chlorpheniramine maleate, d-chlorpheniramine maleate, promethazine, mequitazine, clemastine fumarate, etc.), cardiotonics (examples: aminophylline, caffeine, dl-isoproterenol hydrochloride, etilefrin hydrochloride, norfenefrine hydrochloride, ubidecarenone, etc.), antiarrhythmic agents (examples: procainamide hydrochloride, pindolol, metoprolol tartrate, disopyramide, etc,), diuretics (examples: potassium chloride, cyclopenthiazide, hydrochlorothiazide, triamterene, furosemide, etc,).

They can further include antihypertensive agents (examples: hexamethonium bromide, hydralazine hydrochloride, syrosingopine, reserpine, propranolol hydrochloride, captopril, methyldopa, etc.), vasoconstrictors (examples: dihydroergotamine mesylate, etc.), vasodilators (examples: etafenone hydrochloride, diltiazem hydrochloride, carbochromen hydrochloride, pentaerythritol tetranitrate, dipyridamole, isosorbide nitrate, nifedipine, nicametate citrate, cyclandelate, cinnarizine, etc.), agents for arteriosclerosis (examples: ethyl linoleate, lecithin, clofibrate, etc.), agents for the circulatory system (examples: nicardipine hydrochloride, meclofenoxate hydrochloride, cytochrome C, pyridinol carbamate, vinpocetine, hopantenate calcium, pentoxifylline, idebenone, etc.), respiratory stimulants (examples: dimefline hydrochloride, etc.), antitussives and expectorants (examples: codeine phosphate, dihydrocodeine phosphate, dextromethorphan hydrobromide, noscapine, L-cysteine methyl ester hydrochloride, bromhexine hydrochloride, theophylline, ephedrine hydrochloride, amlexanox, etc.), hepatoprotectants (examples: osalmid, phenyl propanol, hymecromone, etc.), agents for intestinal disorders (examples: berberine hydrochloride, loperamide hydrochloride, etc,), agents for digestive organs (examples: metoclopramide, fenipentol, domperidone, etc.), vitamins (examples: retinol acetate, dihydrotachysterol, etretinate, thiamine hydrochloride, thiamine sulfate, fursultiamine, octotiamine, shikochiamin*, riboflavin, pyridoxine hydrochloride, pyridoxal phosphate, nicotinic acid, pantethine, cyanocobalamin, biotin, ascorbic acid, phytonadione, menatetrenome, etc.), antibiotics (examples: benzathine benzylpenicillin, amoxicillin, ampicillin, cyclacillin, cefaclor, cephalexin, erythromycin, kitasamycin, josamycin, chloramphenicol, tetracycline, griseofulvin, cefuzonam, etc.), chemical therapeutic agents (examples: sulfamethoxazole, isoniazid, ethionamide, thiazosulfone, nitrofurantoin, enoxacin, ofloxacin, norfloxacin, etc.).

Water-soluble polymers may also be added. Examples include hydroxypropylmethylcellulose (HPMC), or carboxymethylcellulose (CMC). These materials without the permeation enhancing agent of the invention may increase the release rate of drugs but in an uncontrolled catastrophic manner by destabilizing the pseudolatex or latex dispersion and rendering the pseudolatex or latex film or coating essentially immediate release.

The plasticizer that may be used in this invention is a substance that lowers the glass transition temperature and the minimum film forming temperature of ethylcellulose. Examples that can be cited include acetylated monoglyceride, triethyl citrate, medium-chain fatty acid triglycerides, acetyl triethyl citrate, tributyl citrate, acetyl tributyl citrate, dibutyl adipate, dibutyl sebacate, diethyl phthalate, glycerol, propylene glycol, polyethylene glycol, oleic acid and oleinol. In general, the amount of plasticizer is on the order of 10 to 50 parts by weight, and, preferably, 20 to 40 parts by weight per 100 parts by weight of ethylcellulose.

The plasticizer may comprise less than or equal to 50% by weight, less than or equal to 40% by weight, less than or equal to 30% by weight, less than or equal to 25% by weight, less than or equal to 20% by weight, less than or equal to 15% by weight, less than or equal to 10% by weight, less than or equal to 5% by weight, less than or equal to 3% by weight, or less than or equal to 50% by weight of said latex or pseudolatex composition. Preferably, the plasticizer comprises 0.5% to 25% by weight of said latex or pseudolatex composition.

In this invention, the thickness of the film of film coated particles should generally be, but not limited to, 30 microns or greater. When it is less than 30 microns the film strength and integrity may be low and may tend to change over time. Although there is no specific upper limit, if it is too thick, film coating may take a long time, which may not be practical. In terms of an upper limit, a general upper limit may be, but is not limited to, approximately 100 microns. When the film becomes thicker, there is the effect that the release rate may be excessively slowed. In such a case, a suitable permeation enhancing agent may be used to give a suitable release rate and a suitable film thickness. The quantity of coating varies greatly depending on the area, particle size and shape of the uncoated particles and the smoothness of their surfaces. However, though not limiting, it should be on the order of 1 to 100 parts by weight, and, preferably, on the order of 3 to 25 parts by weight, per 100 parts by weight of the uncoated particles.

In this invention, the film coated particles may also include a seal coat of immediate release coating such as hydroxypropylmethylcellulose, microcrystalline cellulose-carrageenan (LustreClear FMC Corp) etc. with the objective of decreasing the batch variations that may occur with coating of aqueous dispersion films or for preventing interactions between the drug and the aqueous dispersion film former, or they may also be coated on the outside of the aqueous dispersion film with other film coating agents in addition to the aqueous dispersion with the objective of preventing agglomeration during heat treatment or storage or for conferring enteric properties.

The thickness of the film increases the particle size distribution of the uncoated particles. It is preferred that the particle size distribution is in the range of 75 to 1410 microns. It is more preferred that it is in the range of 75 to 1000 microns. When the particle size distribution is in this range, the preparation is easily taken orally The film coated particles can also be taken orally mixed with food products, enclosed in a capsule, enrobed in film or embedded in a tablet.

In this invention, the film coated particles can be administered as is, or they can be used mixed with other drug preparations, or they can be mixed with other vehicles and drugs or particles that contain drugs or particles that have been subjected to film coating, after which they can be made into tablets or pills. In addition to medicinal or veterinary uses, they can also be used for agricultural chemicals, fertilizers, foods, cosmetics or industrial applications.

The process of the invention involves a process for coating a substrate with aqueous latex or pseudolatex film coating composition as described above. The coating step may be followed by a heat treatment step. The coating step may optionally be carried out under high relative humidity conditions and the heating step may be carried out under low relative humidity conditions. The humidity may be maintained by direct humidification of the process air, spraying an aqueous solution into a coating chamber where the substrate is located, or by diluting the aqueous latex or pseudolatex coating composition with an aqueous solution. The terms, "high" and "low" relative humidity refer to a relative humidity higher than ambient relative humidity without intervention and to a relative humidity lower than ambient relative humidity without intervention, respectively. Spraying can be done at, for example about 15% solids content.

The present invention recognizes that a high capillary force also can be maintained by use of high humidity during the coating process, e.g. greater than 40% in the coating step, followed by a low humidity heat treatment step, e.g. less than 55% relative humidity in the drying step. Suitable high humidity conditions for the coating step are, for example, greater than 40% relative humidity, greater than 50% relative humidity, greater than 60% relative humidity, greater than 70% relative humidity, greater than 80% relative humidity, or greater than 90% relative humidity, so long as the pellets do not aggregate. Suitable low humidity conditions for the heat treatment step are, for example, less than 16 g water/kg of air, less than 10 grams of water/kg air, less than 8 grams of water/kg air, less than 5 grams of water per kg of air or less than 3 grams of water per kg of air so long as overdrying is avoided The air flow, temperature, and relative volume of moisture to be removed will guide selection of the appropriate low humidity condition for heat treatment step. For example, use of a fluidized bed requires a higher humidity of the inlet air stream to avoid over drying. After coalescence, the film properties are said to remain constant.

The heat treatment step is preferably carried out at a temperature above a minimum film-forming temperature of the aqueous latex or pseudolatex coating composition. The substrate may be a pellet, tablet, soft capsule, hard capsule, powders, granules, beads, films and film enrobed dosage forms.

The coated substrate may exhibit one or more of superior barrier properties, superior stability of release profile over a period of up to three years under normal storage conditions, and/or a lower diffusivity, all as compared to a substrate prepared under low humidity coating and curing conditions.

Figure 27:
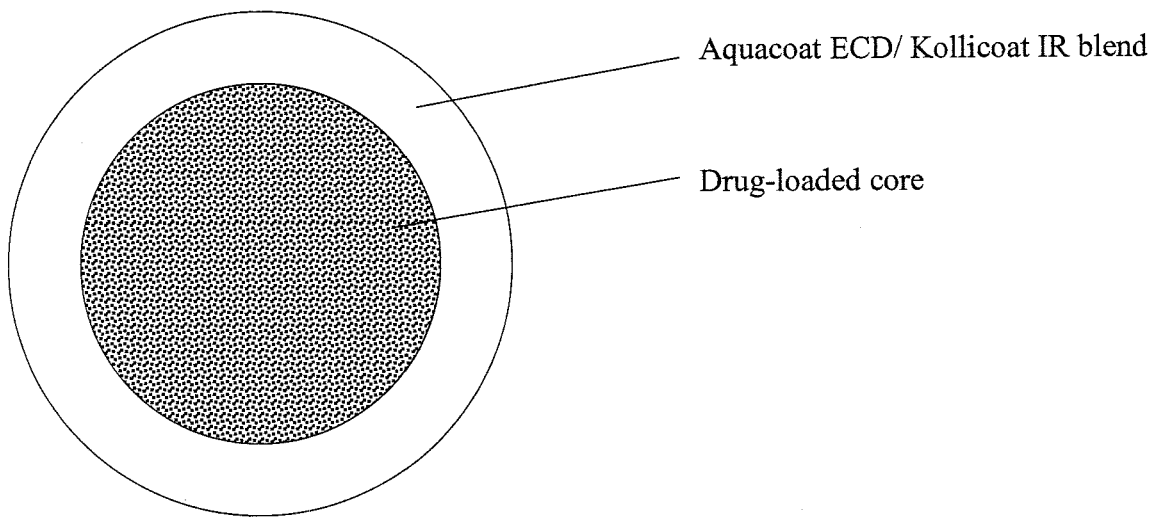
FIG. 27 shows a schematic of a second embodiment of a drug coated particle using an Aquacoat® ECD/Kollicoat® IR blend.
Figure 38:
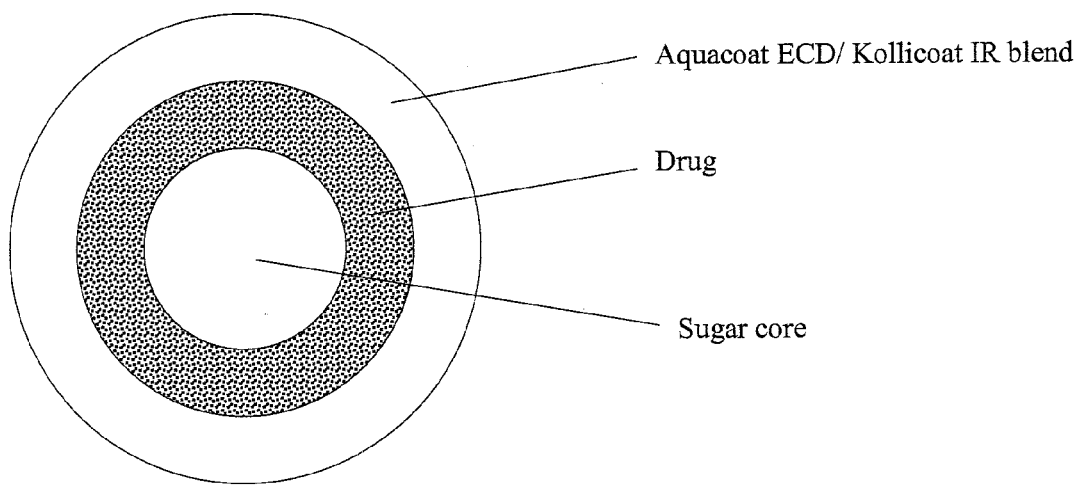
FIG. 38 shows a schematic of one embodiment of a drug coated particle using a Aquacoat® ECD/Kollicoat® IR blend.

The coated substrate may be a drug matrix as shown in FIG. 27 or a core coating with a drug layer, as shown in FIG. 38. In the embodiment of FIG. 38, the core may be osmotically active if the core is a sugar core, for example. The present invention may provide customizable release from both types of pellets.

Variations in the type and amount of plasticizer employed in the film coatings of the present invention can be used to customize drug-release properties. For example, as shown below, adding different amounts of a poly(vinyl alcohol)-poly(ethylene glycol)-graft-copolymer to ethylcellulose-based film coatings, broad ranges of release patterns have been achieved, irrespective of the water-solubility of the drug or the osmotic activity of the pellet core.

Also, as demonstrated in the examples below, the presence of only minor amounts of appropriate additives as described above can effectively provide long term stability of aqueous ethylcellulose-based film coatings in accordance with the present invention even under stress conditions.

The examples also show that coatings in accordance with the present invention, e.g. using ethylcellulose:PVA-PEG graft copolymer blends, provide substantially constant drug release rates despite some variations in the coating properties that result in many conventional manufacturing processes. Thus, the present coatings and coating process are robust and should be scalable to large scale production.

EXAMPLES

Adding only very small amounts of a poly(vinyl alcohol)-poly(ethylene glycol)-graft-copolymer to Aquacoat® ECD-based film coatings, desired membrane properties can effectively be adjusted. In particular, the resulting water uptake rates and extents, dry weight loss kinetics and drug permeabilities can be altered. Importantly, these effects can be quantitatively predicted based on Fick's 2nd law of diffusion.

Ethylcellulose-based film coatings are frequently used to control the release rates of drugs from solid oral dosage forms, e.g. pellets and tablets. As ethylcellulose is water-insoluble the resulting release patterns can be controlled within the entire gastrointestinal tract. However, due to the limited permeability of this polymer for many drugs it is sometimes challenging to adjust desired release rates. The addition of hydroxypropyl methylcellulose (HPMC) to the coatings has been proposed in the past to accelerate drug release. However, relatively high quantities are required and the presence of HPMC in the coating dispersions can cause coagulation.

The major aim of the present study was to identify an easily adjustable formulation parameter allowing effective alteration of the properties of Aquacoat® ECD-based film coatings, in particular their drug permeabilities.

In a screening phase permeation enhancing agents were mixed with Aquacoat® ECD plasticized with triethyl citrate (25% w/w based on ECD solids). Aquacoat® ECD was plasticized by stirring with triethyl citrate for 24 hours prior to addition of permeation enhancing agent. The dispersion stability was checked by optical microscopy for aggregation, coagulation or flocculation. Films were cast on Teflon® and cured for 24 hours at 60° C. The cast films were assessed in terms of appearance, transparency, inhomogeneities, or cracks and mechanical properties (semi-quantitative brittleness or flexibility).

The following materials were evaluated at levels of 10 to 30% w/w with respect to Aquacoat® ECD solids: Poly(ethyl acrylate, methyl methacrylate, trimethylammonioethyl methacrylate chloride) (Eudragit® RS 30 D, Eudragit® RL 30 D, Röhm GmbH), Poly(ethyl acrylate, methyl methacrylate) (Eudragit® NE 30 D Röhm GmbH), Polyvinyl acetate (Kollicoat® SR 30 D BASF), Polyvinyl alcohol-polyethylene glycol graft copolymer (Kollicoat® IR, BASF), Polyvinylpyrrolidone, Microcrystalline cellulose-carrageenan (Lustreclear LC103, Lustreclear LC200 FMC Corp), Kappa carrageenan (Gelcarin® GP 911, FMC Corp), Iota carrageenan (Gelcarin® GP 379, FMC Corp) Lambda carrageenan (Viscarin® GP 209, FMC Corp), Polyethyleneglycol 400, Polyethyleneglycol 4000, Hydroxypropylmethylcellulose, Sodium Carboxymethylcellulose, Cellulose Acetate Phthalate (Aquacoat® CPD FMC Corp), Sodium Alginate (Protanal® LFMg 5/60, Protanal® LF 120 M FMC Corp), Propylene Glycol Alginate (Protanal® ester SD-LB FMC Corp), Sodium Starch Glycolate, Starch, Sucrose (Saccharose), Lactose, Mannitol, Sorbitol, Glucose, Sodium Chloride, Calcium Hydrogen Phosphate, Disodium Hydrogen Phosphate.

Results of Dispersion Compatability/Film Properties Screening

Preferred examples of compatible mixtures of Aquacoat® ECD and permeation enhancing agent giving good films.

Polyvinyl alcohol-polyethylene glycol graft copolymer (Kollicoat® IR) was compatible in dispersion and gave good mixed films.

Gelcarin® GP911 (kappa carrageenan) and Viscarin® GP209 (lambda carrageenan) both gave viscous stable dispersions with Aquacoat® ECD and good mixed film properties.

Propylene Glycol Alginate (Protanal® ester SD-LB and starch were compatible with Aquacoat® ECD dispersions and gave good films.

Poly(ethyl acrylate, methyl methacrylate), Eudragit® NE 30 D, was physically compatible in dispersion and gave good mixed films.

Sucrose (saccharose), lactose, mannitol, sorbitol and glucose were compatible with Aquacoat® ECD dispersions and gave good films. However it is necessary to ensure recrystallisation of the sugars in the film does not occur.
Additional Examples of Compatible Mixtures of Aquacoat® ECD and Permeation Enhancing Agent.

The Aquacoat ECD dispersion was not destabilized but the viscosity of Gelcarin® GP379 (iota carrageenan) in Aquacoat ECD was high and the films were not homogenous.

Polyvinyl acetate (Kollicoat® SR 30 D) was compatible with Aquacoat® ECD in dispersion (i.e., no destabilisation) but gave inhomogenous films.

The phosphate salts (calcium hydrogen and disodium hydrogen) were compatible with Aquacoat® ECD dispersions (i.e. no destabilisation) but gave inhomogenous films.

Polyethylene glycol 400 did not destabilize the Aquacoat® ECD dispersion but exhibited phase separation in the mixed film, forming visible exudations.

Polyethylene glycol 4000 not destabilize the Aquacoat® ECD dispersion and exhibited less phase separation in the mixed film, but the films showed reduced flexibility.

Polyvinylpyrrolidone did not destabilize Aquacoat® ECD dispersion but the films were less flexible and tended to crack.

Comparative examples (of compositions not in accordance with the invention) of incompatible mixtures of Aquacoat® ECD and other additives LustreClear® LC103 (microcrystalline cellulose-carrageenan) gave very viscous destabilized Aquacoat® dispersions and the mixed films tended to crack.

Hydroxypropylmethylcellulose destabilized the Aquacoat® dispersions and gave inhomogenous films.

Sodium carboxymethylcellulose destabilized the Aquacoat® dispersions and gave films which tended to crack.

Sodium chloride destabilized the Aquacoat® dispersions and gave inhomogenous films, with recrystallisation and cracking.

The cationic copolymers poly(ethyl acrylate, methyl methacrylate, trimethylammonioethyl methacrylate chloride), Eudragit® RS 30 D and Eudragit® RL 30 D, destabilized the plasticized Aquacoat® ECD dispersion.

Using cast thin films drug (theophylline) and water permeability, weight loss and mechanical properties were determined to study the effect of the ratio of Aquacoat® ECD 30 permeation enhancing agent on the water uptake, weight loss behavior and drug release kinetics of/from thin, polymeric films in 0.1M HCl.

The films according to the present invention were relatively insensitive to calcium ion concentrations during drug-release, as demonstrated in the examples below. This provides the advantage that drug-release rates will remain relatively predictable despite potential variations in calcium ion concentrations which may be encountered in the gastrointestinal tract.

Preparation of Drug-Free Thin, Polymeric Films

Thin, polymeric films were prepared by blending an aqueous dispersion of Aquacoat® ECD 30 with an aqueous dispersion containing one of Kollicoat® IR, Gelcarin® GP 911, Viscarin® GP 209, Protanal® ester SD-LB, Maize starch.

Preparation of the Aquacoat® ECD 30 Dispersion

| Polymer: | Aquacoat® ECD 30 |
|---|---|
| Plasticizer: | 25% TEC w/w, based on the dry polymer mass (plasticization time: 24 h) |

The polymer content of the Aquacoat® dispersion was adjusted to 15% w/w by dilution with demineralised water before blending with the dispersion of permeation enhancing agent.

Preparation of Permeation Enhancing Agent Dispersions/Solutions

The permeation enhancing agents were dispersed or dissolved in demineralised water to 1 or 30% w/w solid content depending on the viscosity of the resulting solution/dispersion (Table 1).

TABLE 1

Investigated permeation enhancing agents

| Agents | Solids, % w/w | Aquacoat® ECD:agent ratio investigated (w/w) |
|---|---|---|
| Kollicoat® IR | 30 | 97.5:2.5, 95:5, 90:10 |
| Gelcarin® GP 911 | 1 | 97.5:2.5, 95:5, 90:10 |
| Viscarin® GP 209 | 1 | 97.5:2.5, 95:5, 90:10 |
| Protanal® ester SD-L | 1 | 97.5:2.5, 95:5, 90:10 |
| Maize starch | 30 | 90:10, 80:20; 70:30 |

The permeation enhancing agent solution/dispersion was carefully added to the Aquacoat® dispersion and stirred for 30 min. The resulting dispersion was poured into Teflon® plates and dried for 24 h at 60 C in an oven.

Preparation of Drug Loaded Thin, Polymeric Films

Theophylline-containing films were prepared similarly but adding a theophylline aqueous solution (0.25% w/w based on the dry polymer/solids mass) to the dispersions.

Water Uptake and Weight Loss Studies

Drug free thin, polymeric films were exposed to 0.1M HCl in a horizontal shaker at 37° C. (80 rpm). At pre-determined intervals, samples were withdrawn and dried to constant weight at 60° C. (n=3).

Drug Release Experiments

Drug-containing films were exposed to 0.1M HCl in a horizontal shaker at 37° C. (80 rpm). The drug was detected UV-spectrophotometrically at 271 nm (n=3)

Results and Discussion

FIGS. 1-2 show the results for mixtures of Kollicoat® IR with Aquacoat® ECD30

Figure 3B:
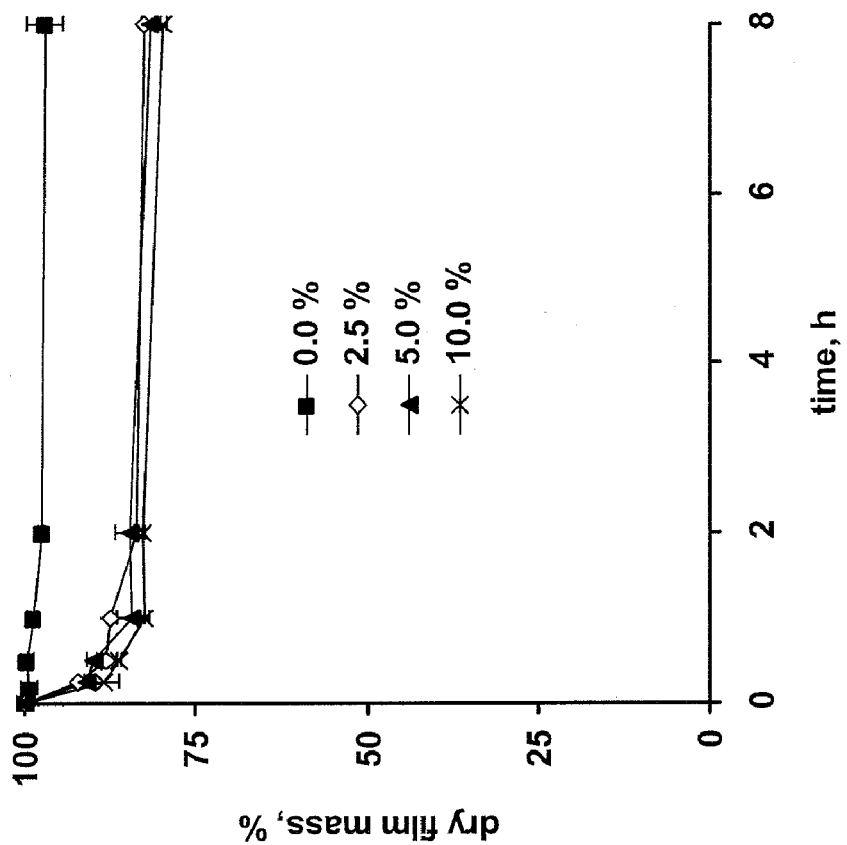
FIGS. 3(a)-3(b) show the effect of the Viscarin® GP 209 content on: (a) the water uptake and (b) dry weight loss behavior of thin polymeric films in 0.1M HCl for mixtures of Viscarin® GP 209 with Aquacoat® ECD30
Figure 3A:
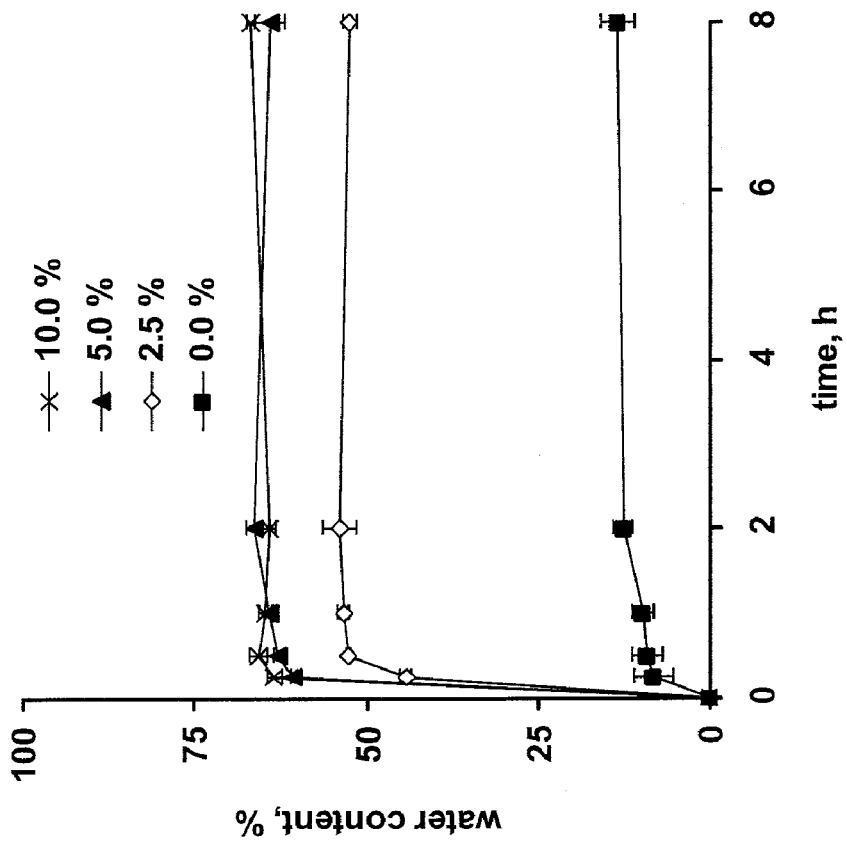
Figure 4:
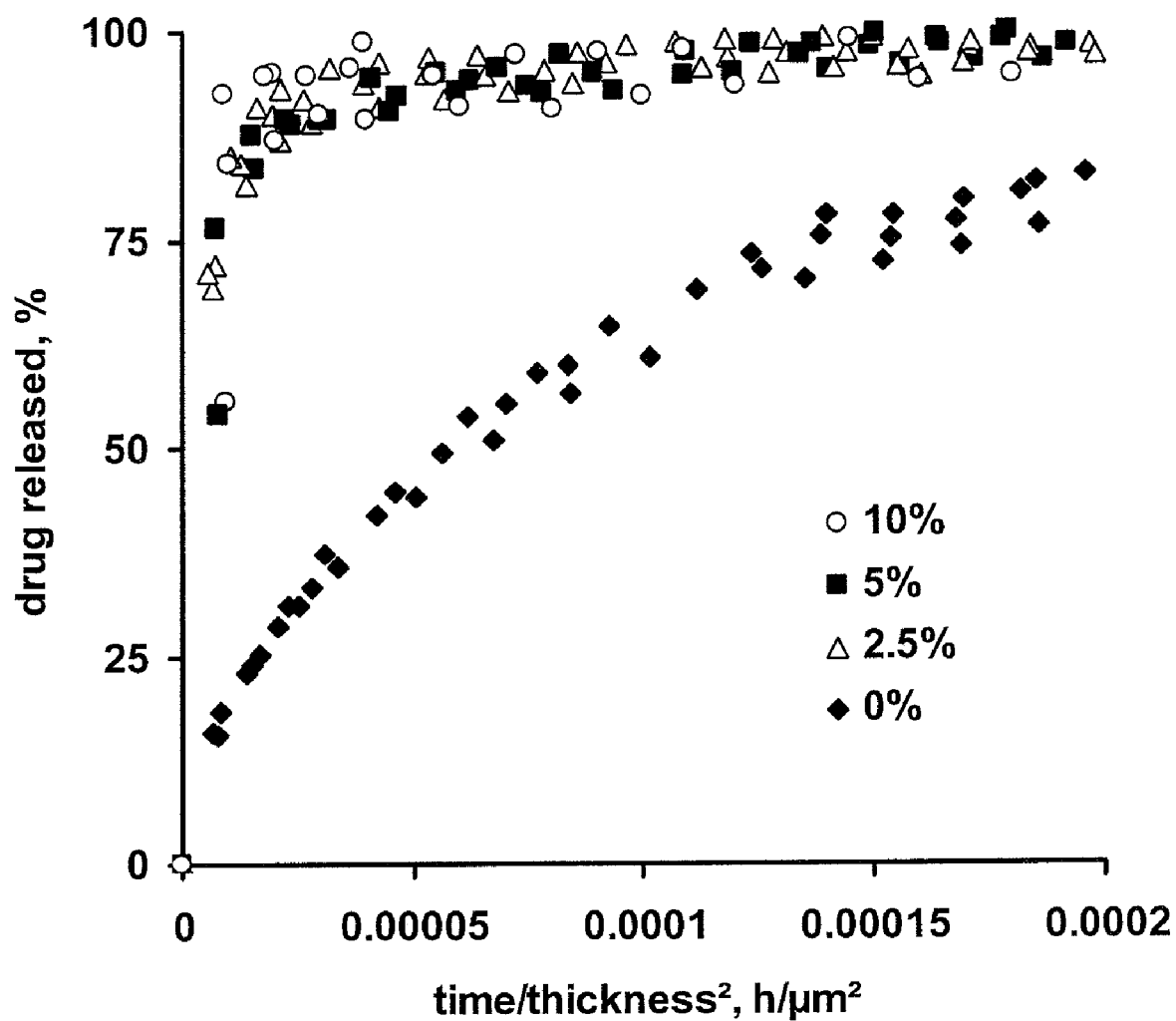
FIG. 4 shows the effect of the Viscarin® GP 209 content on theophylline release from thin polymeric films in 0.1M HCl for mixtures of Viscarin® GP 209 with Aquacoat® ECD30

FIGS. 3-4 show the results for mixtures of Viscarin® GP 209 with Aquacoat® ECD30

Figure 5B:
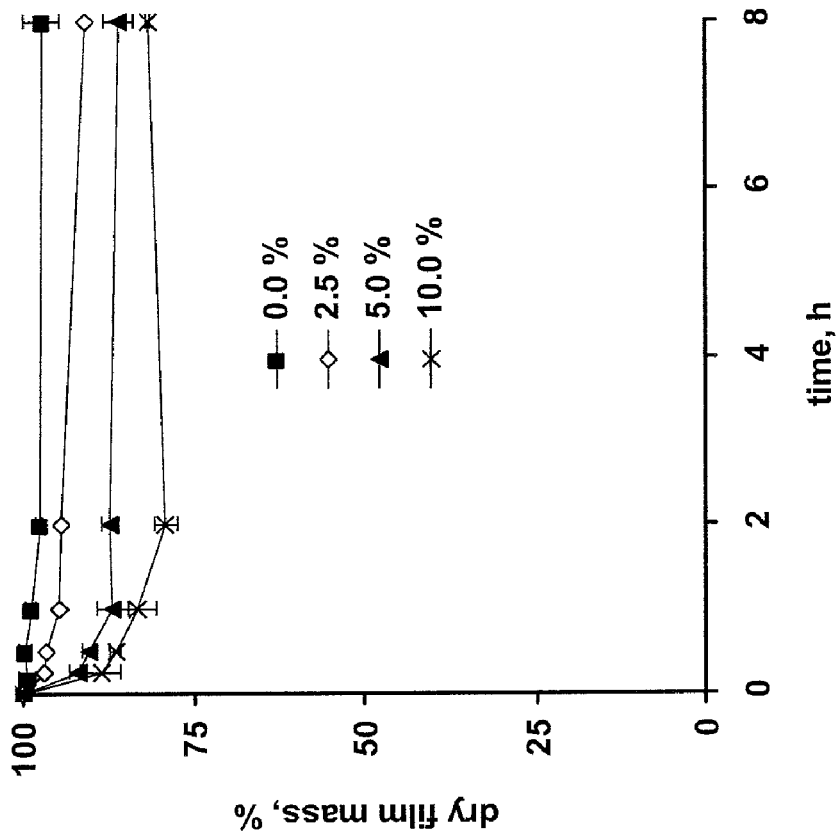
FIGS. 5(a)-5(b) show the effect of the Gelcarin® GP 911 content on: (a) the water uptake and (b) dry weight loss behavior of thin polymeric films in 0.1M HCl for mixtures of Aquacoat® ECD 30™ and Gelcarin® GP 911.
Figure 5A:
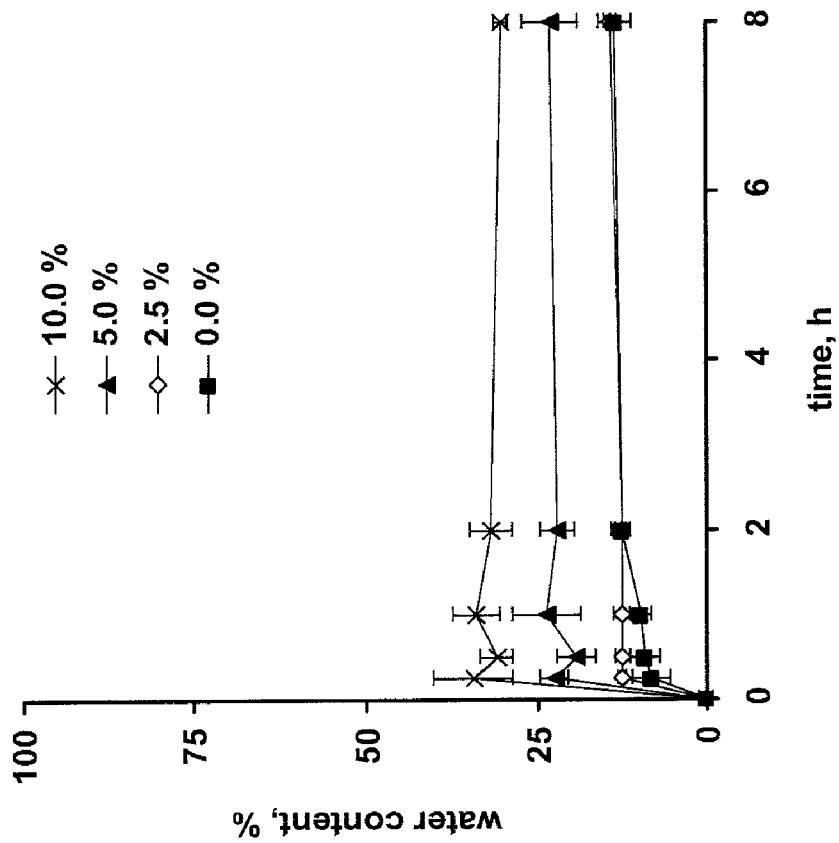
Figure 6:
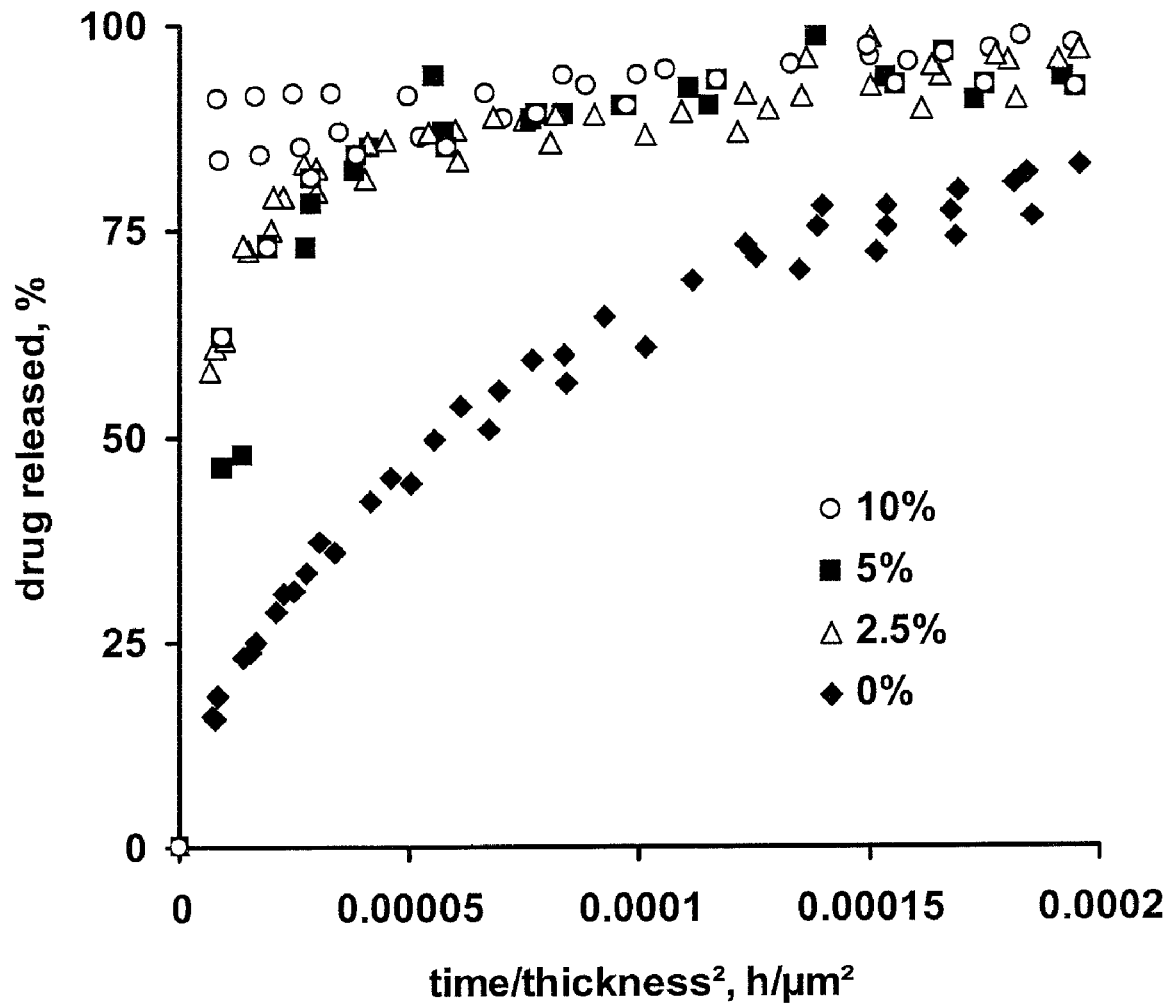
FIG. 6 shows the effect of the Gelcarin® GP 911 content on theophylline release from thin polymeric films in 0.1M HCl for mixtures of Aquacoat® ECD 30 and Gelcarin® GP 911.

FIGS. 5-6 show the results for mixtures of Aquacoat® ECD 30 and Gelcarin® GP 911

Figure 7B:
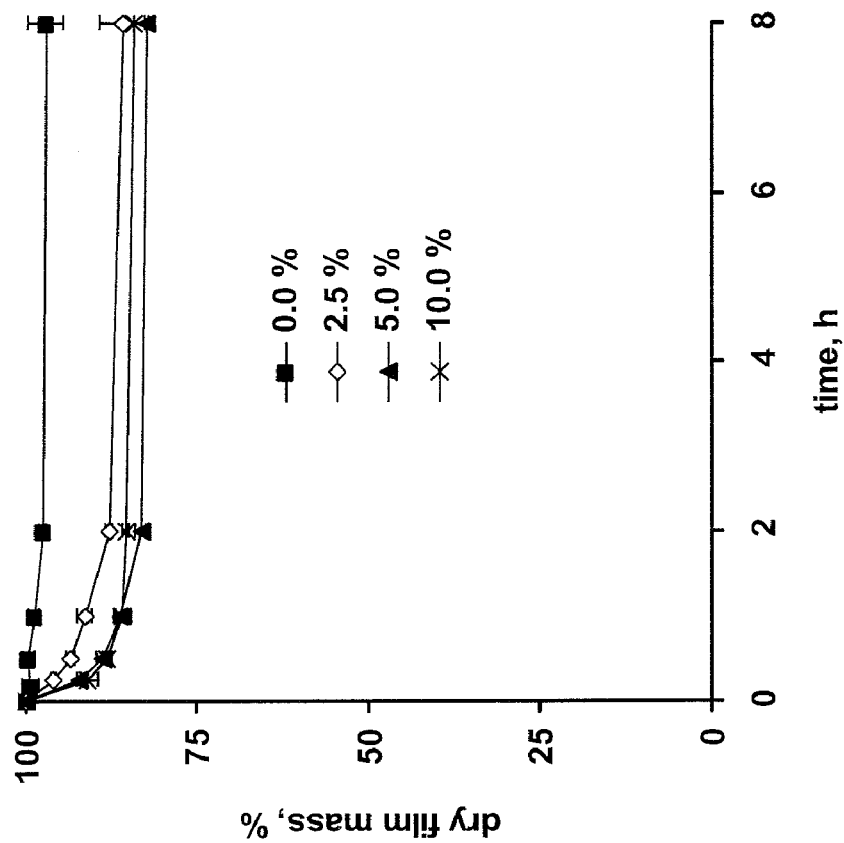
FIGS. 7(a)-7(b) show the effect of the Protanal® ester SD-LB content on: (a) the water uptake and (b) dry weight loss behavior of thin polymeric films in 0.1M HCl for mixtures of Aquacoat® ECD 30 and Protanal® ester SD-LB.
Figure 7A:
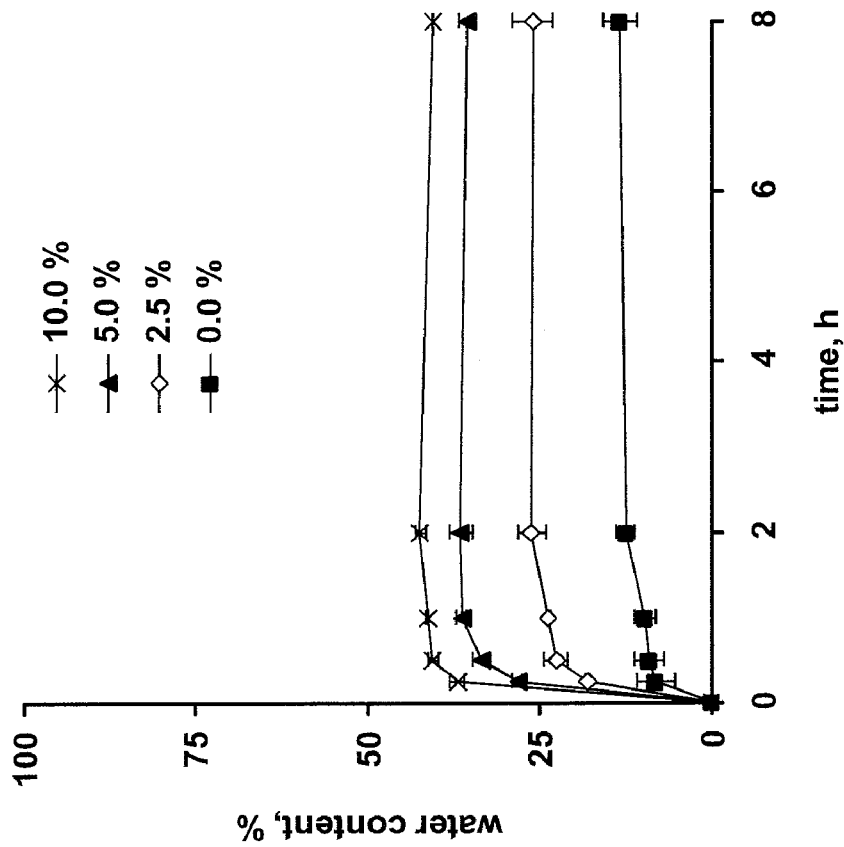
Figure 8:
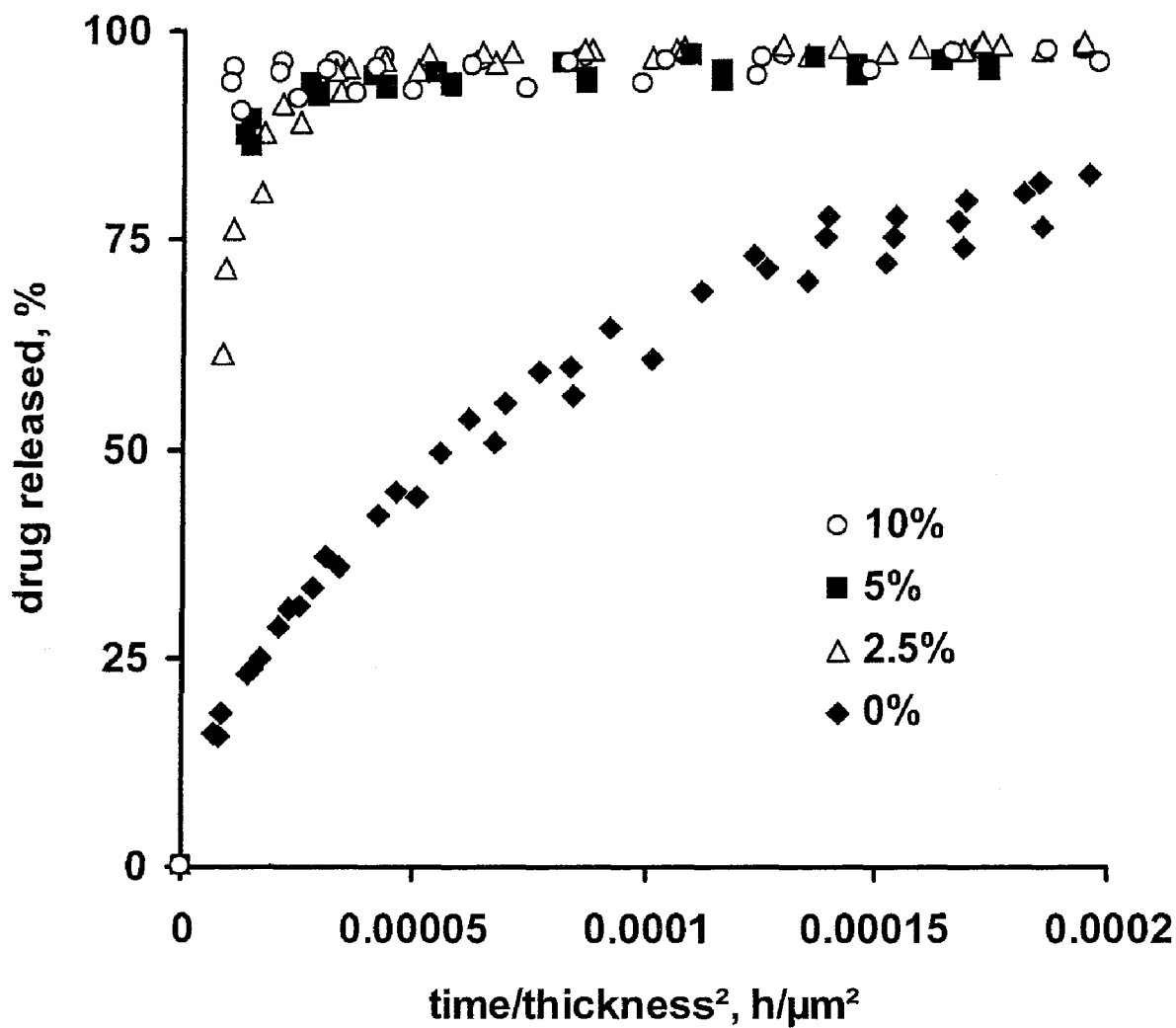
FIG. 8 shows the effect of the Protanal® ester SD-LB content on theophylline release from thin polymeric films in 0.1M HCl for mixtures of Aquacoat® ECD 30 and Protanal® ester SD-LB.

FIGS. 7-8 show the results for mixtures of Aquacoat® ECD 30 and Protanal® ester SD-LB™.

Figure 9B:
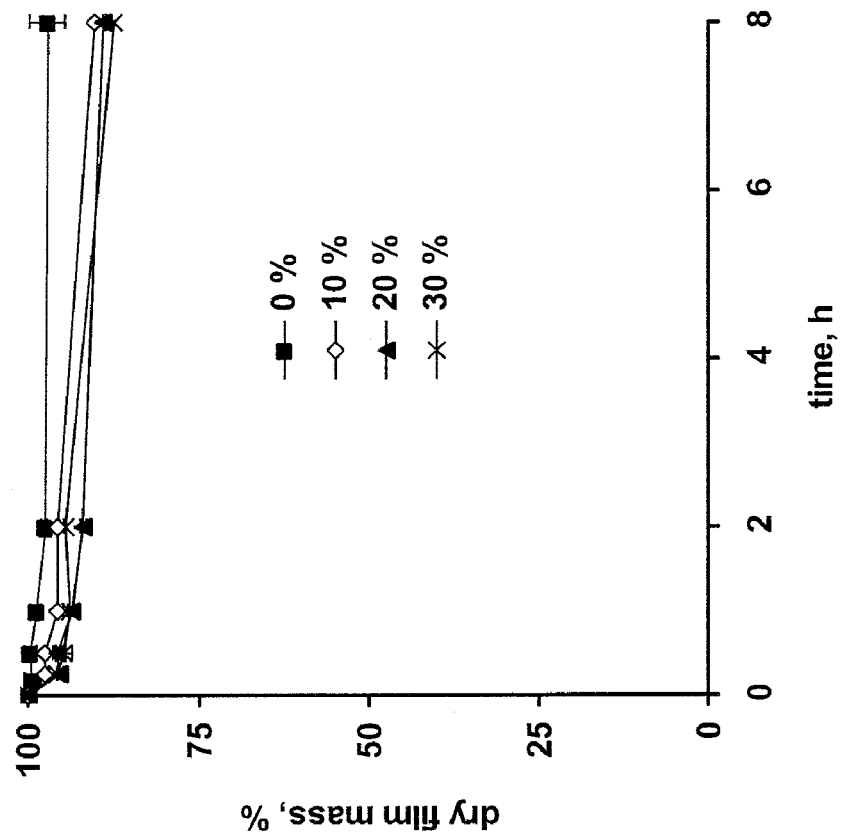
FIGS. 9(a)-9(b) show the effect of the maize starch content on: (a) the water uptake and (b) dry weight loss behavior of thin polymeric films in 0.1M HCl for mixtures of Aquacoat® ECD 30 and Maize starch.
Figure 9A:
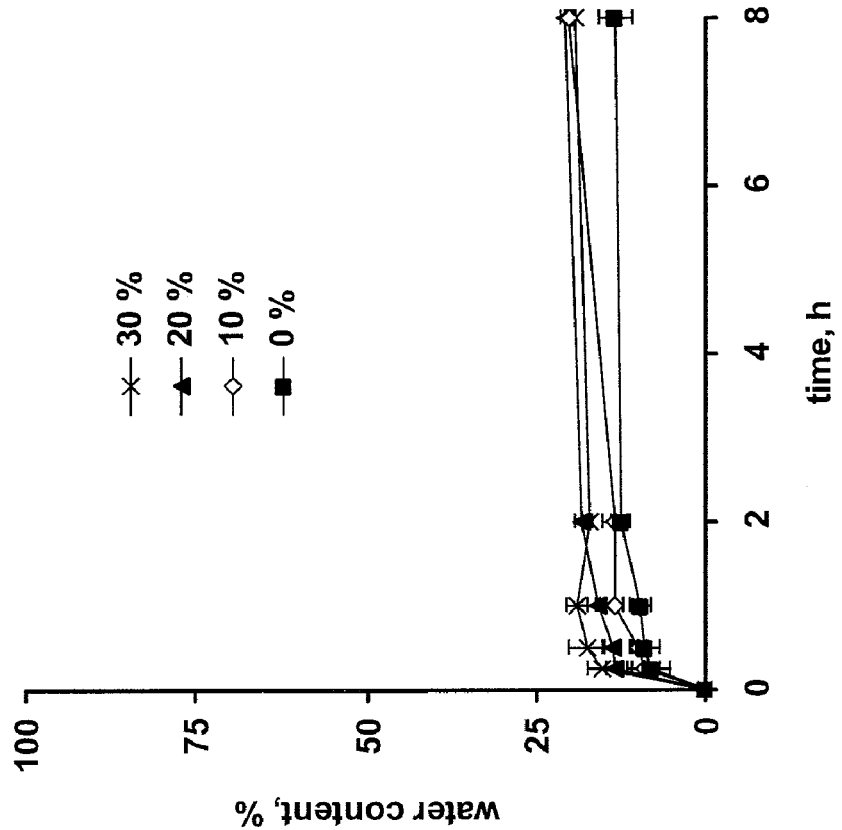
Figure 10:
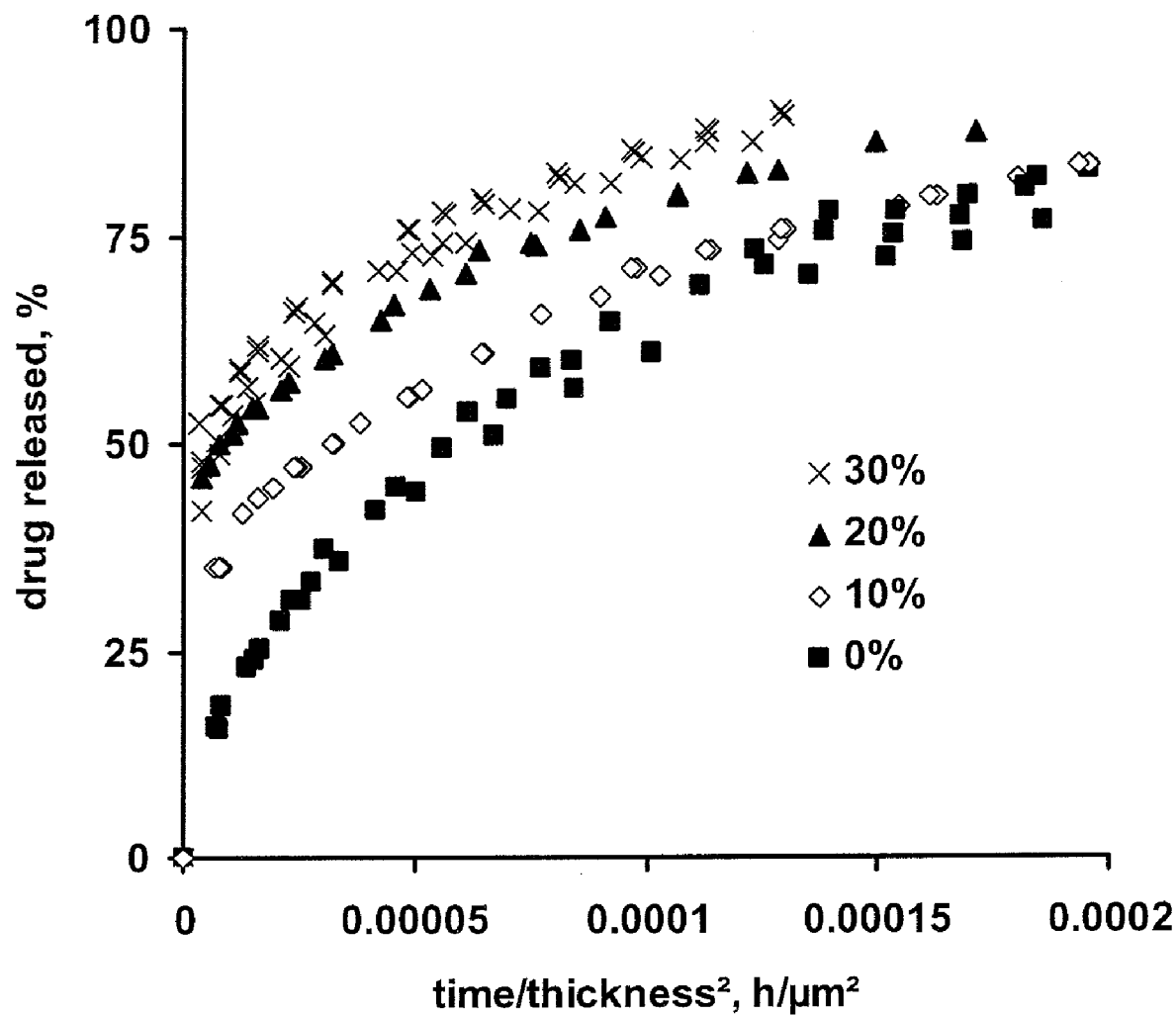
FIG. 10 shows the effect of the maize starch content on theophylline release from thin polymeric films in 0.1M HCl for mixtures of Aquacoat® ECD 30 and Maize starch.

FIGS. 9-10 show the results for mixtures of Aquacoat® ECD 30 and Maize starch.

Film Preparation

Thin, polymeric films were prepared by casting aqueous dispersions of ethylcellulose (Aquacoat® ECD) and a poly (vinyl alcohol)-poly(ethylene glycol)-graft-copolymer (Kollicoat® IR) containing triethyl citrate as a plasticizer (25% w/w) onto Teflon® plates and subsequent controlled drying. Drug-containing films were prepared accordingly, adding theophylline to the aqueous dispersions. The drug loading was below the solubility of theophylline in the polymeric systems (clear films, monolithic solutions).

Film Characterization

The water uptake and dry weight loss kinetics of the films were measured gravimetrically upon exposure to 0.1M HCl and phosphate buffer pH 7.4. In vitro drug release was monitored in the same media (horizontal shaker, 37° C., UV drug detection).

The apparent diffusion coefficients of water and drug within the polymeric systems, D, were determined by fitting the following solution of Fick's 2nd law of diffusion to the experimentally measured water uptake and drug release kinetics:

$$\frac{M_t}{M_\infty} = 1 - \sum_{n=1}^{\infty} \frac{2 \cdot G^2}{\beta_n^2 \cdot (\beta_n^2 + G^2 + G)} \cdot \exp\left(-\frac{\beta_n^2}{L^2} \cdot D \cdot t\right) \quad (1)$$

with $$\beta \cdot \tan\beta = G \quad (2)$$

and $$G = \frac{L \cdot h}{D} \quad (3)$$

where Mt and M∞ represent the absolute cumulative amounts of drug released/water taken up at time t and infinity, respectively; L denotes the half thickness of the film and h the mass transfer coefficient in the unstirred liquid boundary layer.

Figure 11:
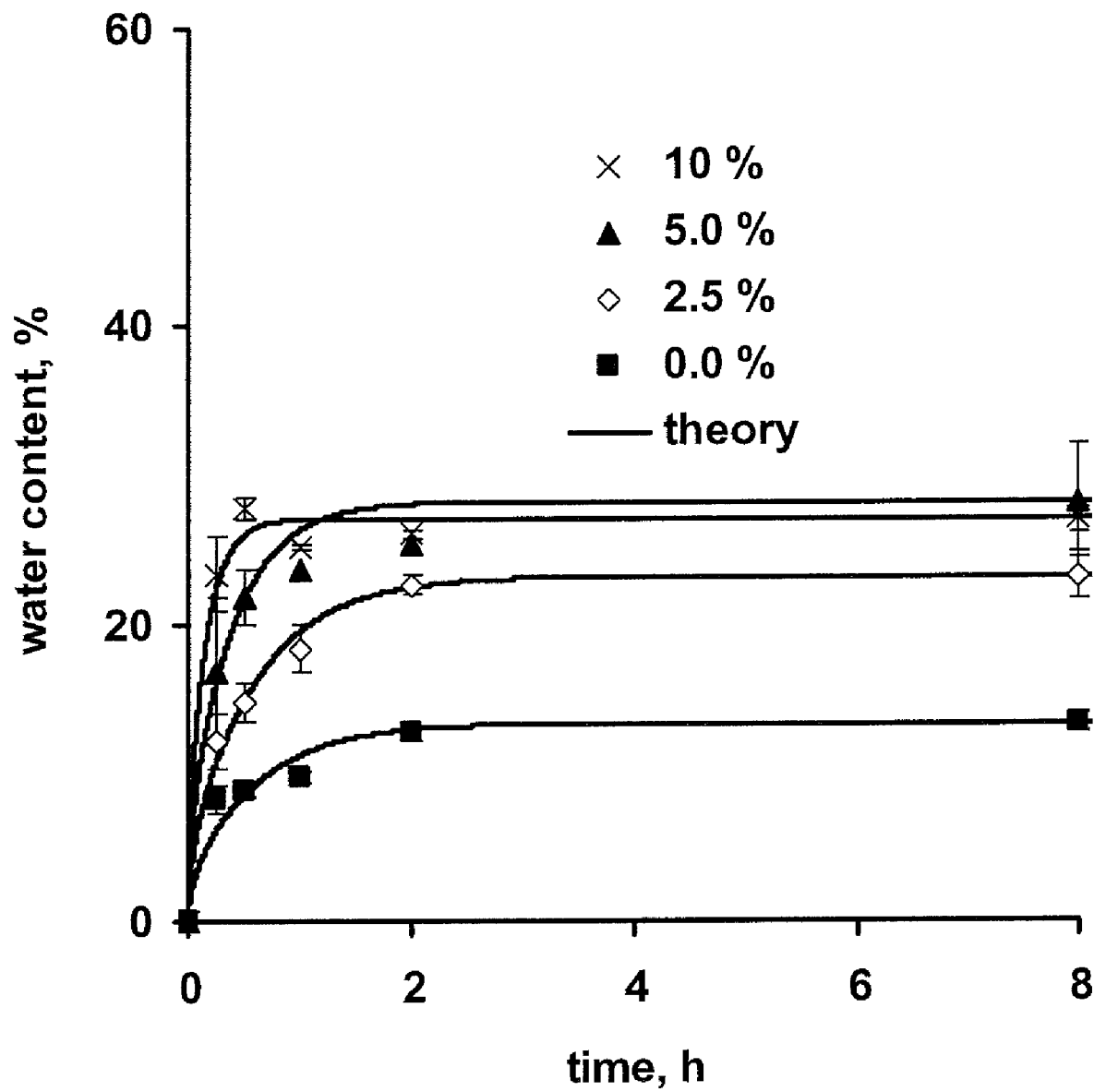
FIG. 11 shows the effects of the presence of small amounts of Kollicoat® IR (indicated in the figure) on the water uptake kinetics of thin Aquacoat® ECD-based films upon exposure to 0.1M HCl (symbols: experiment; curves: theory).

Importantly, the addition of only very small amounts of a poly(vinyl alcohol)-poly(ethylene glycol)-graft-copolymer (Kollicoat® IR) to Aquacoat® ECD-based thin films significantly increased the water-uptake rates of the systems, irrespective of the type of release medium. FIG. 11 (symbols) shows exemplarily the results obtained in 0.1M HCl. Both the rate and the extent of water penetration were affected.

An analytical solution of Fick's 2nd law of diffusion (Eqs. 1-3) could successfully be used to quantitatively describe the experimentally determined results (FIG. 11 curves). Thus, water penetration into the film coatings is primarily controlled by pure diffusion.

Figure 12:
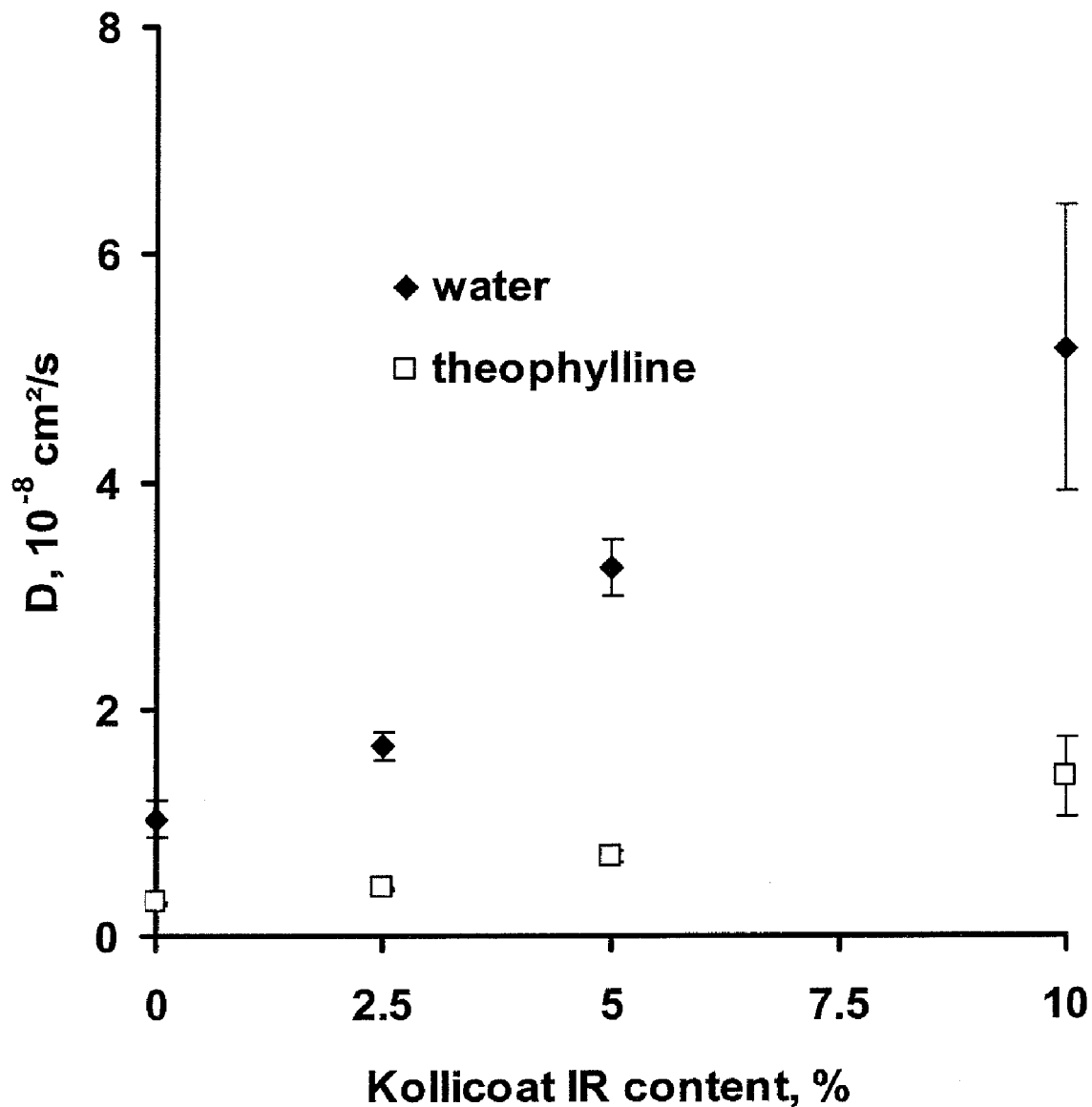
FIG. 12 shows the effects of the Kollicoat® IR content on the diffusion coefficient of water and theophylline in thin Aquacoat® ECD-based films upon exposure to phosphate buffer pH 7.4.

Based on these calculations the diffusion coefficients of water in the Aquacoat® ECD-based films could be determined as a function of the Kollicoat® IR content. FIG. 12 shows exemplarily the results obtained in phosphate buffer pH 7.4 (filled diamonds). Clearly, the water permeability significantly increased with increasing Kollicoat® IR content. In 0.1M HCl, the tendency was similar (data not shown).

Figure 13:
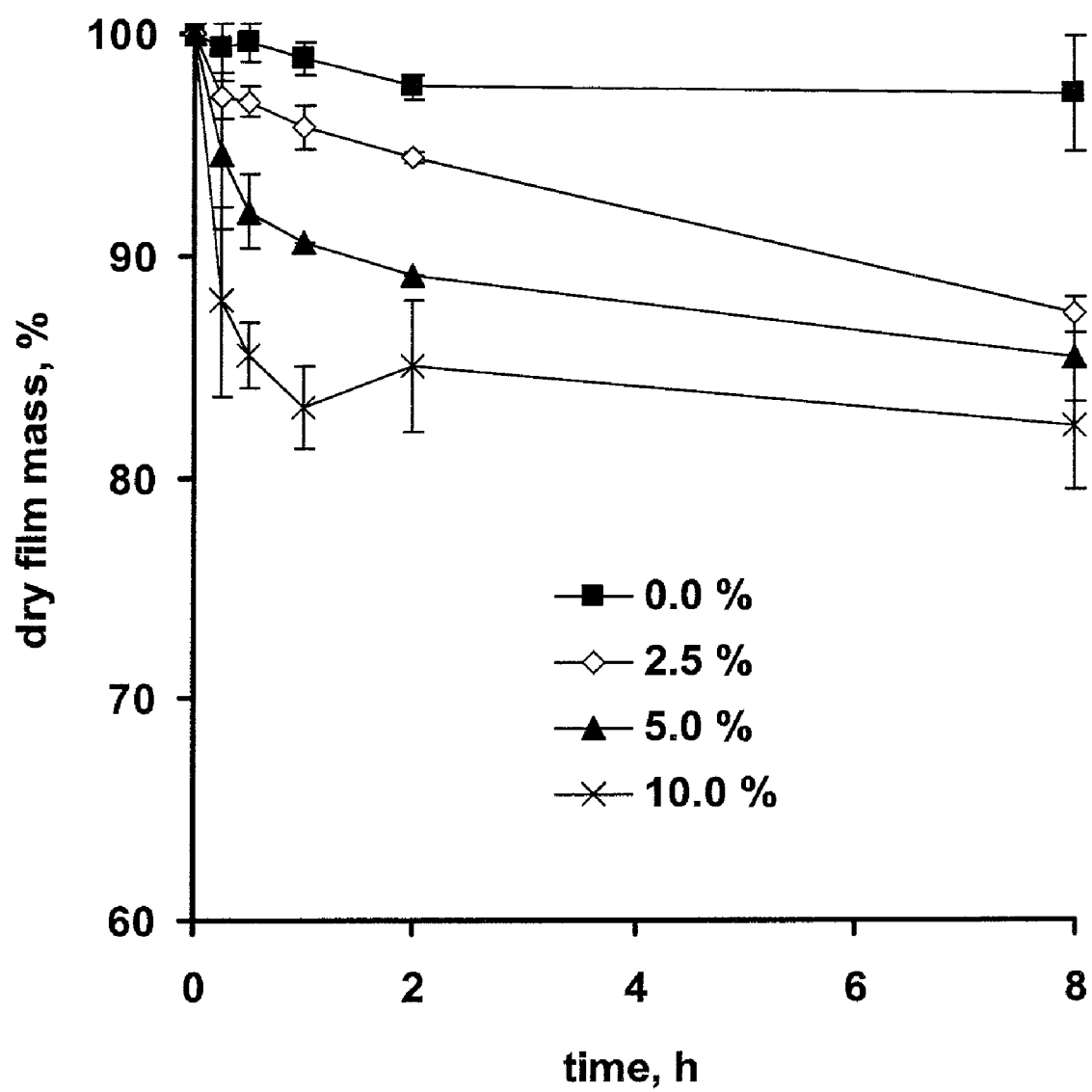
FIG. 13 shows the effects of the Kollicoat® IR content (indicated in the figure) on the dry weight loss kinetics of thin Aquacoat® ECD-based films upon exposure to 0.1M HCl.

The addition of only very small amounts of Kollicoat® IR to Aquacoat® ECD-based coatings also significantly affected the dry weight loss kinetics of the system upon exposure to the release media, e.g. 0.1M HCl (FIG. 13). The increase in dry weight loss in the presence of Kollicoat® IR can be attributed to the leaching of this water-soluble polymer out of the films and to enhanced plasticizer leaching.

Figure 14:
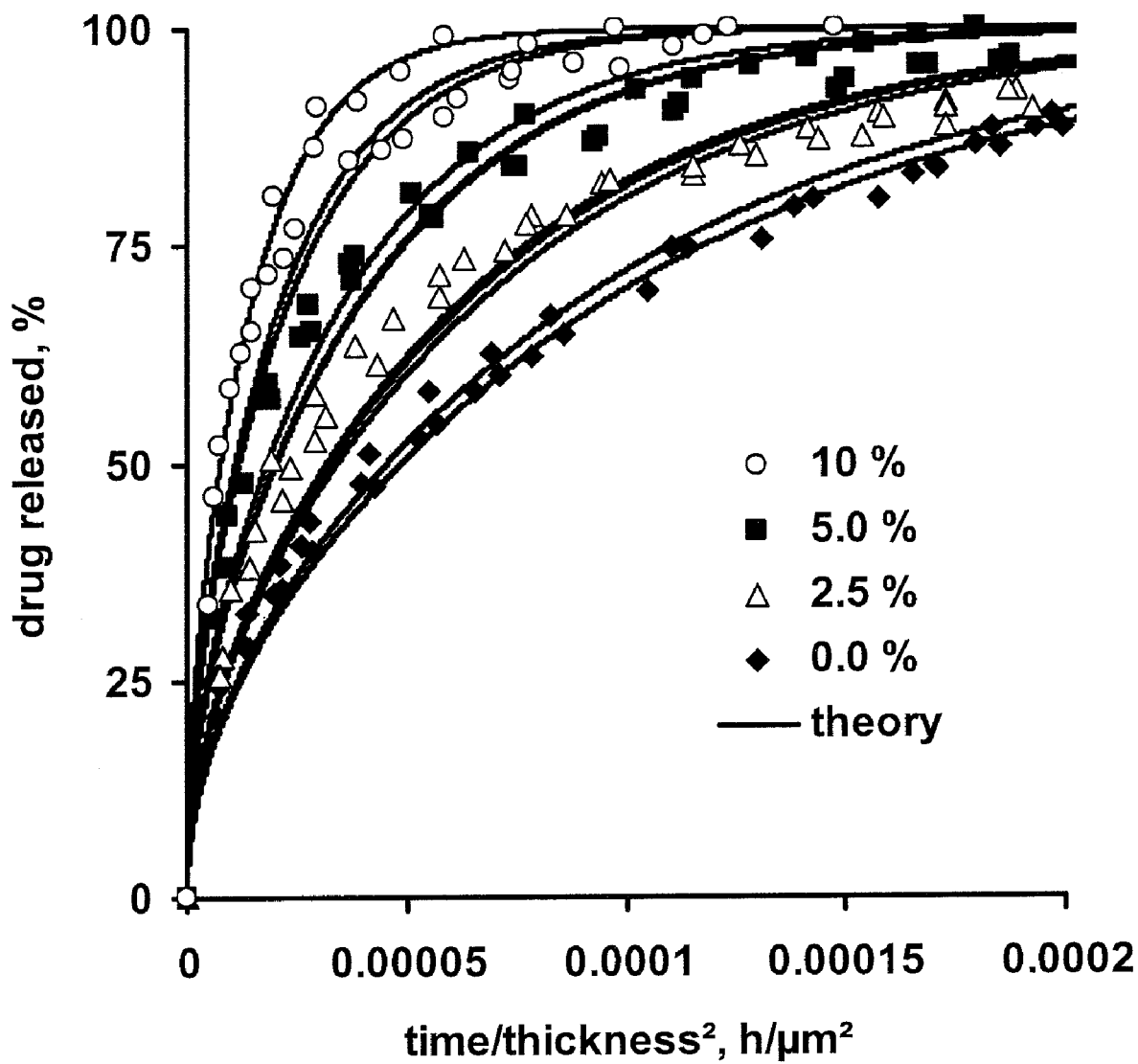
FIG. 14 shows the effects of the Kollicoat® IR content (indicated in the figure) on the release rate of theophylline from thin Aquacoat® ECD-based films upon exposure to phosphate buffer pH 7.4 (symbols: experiment; curves: theory).

Importantly, both effects, the significantly increased water uptake as well as dry weight loss led to a fundamental increase in drug permeability and, thus, release from thin films, irrespective of the type of release medium. FIG. 14 (symbols) shows exemplarily the results obtained in phosphate buffer pH 7.4.

Again, the presented analytical solution of Fick's 2nd law of diffusion (Eqs. 1-3) could successfully be used to quantitatively describe the observed mass transport kinetics (FIG. 14 curves). As it can be seen in FIG. 12, the apparent diffusion of the drug in the film coatings could effectively be increased (factor>4.9) by adding only 10% of the poly(vinyl alcohol)-poly(ethylene glycol)-graft-copolymer.

The apparent diffusion coefficients of water and drug within the polymer films (D) were determined by fitting a solution of Ficks $2^{nd}$ Law of Diffusion to the experimentally determined water uptake and drug release kinetics.

By means of this invention, the optimisation of latex or pseudolatex films or dosage forms coated with latex or pseudolatex, such as Aquacoat® ECD is significantly facilitated. Desired membrane properties, especially, drug permeabilities, can be easily adjusted.

Based on the water uptake, weight loss and thin film drug release kinetics, the following permeation enhancing agents were included in Aquacoat® ECD coatings applied to Theophylline pellets:
Viscarin® GP 209
Kollicoat® IR
Protanal® Ester SD LB The effect of coating level and release media on drug release was investigated as well as the effect of curing conditions (temperature and humidity). Four coating levels were evaluated: 5, 10, 15, 20% (w/w)
Curing Conditions
60° C. for 24 h
60° C. for 48 h
60° C. & 75% R.H. for 24 h+60° C. for 24 h
60° C. & 75% R.H. for 48 h+60° C. for 24 h
Adjustment of Drug Release Patterns from Ethylcellulose-Coated Pellets The major objectives of this study were: (i) to effectively adjust desired drug release patterns from ethylcellulose-coated pellets by adding small amounts of a water-soluble polymer, without affecting the stability of the coating dispersions; and (ii) to study the effects of different curing conditions (temperatures, time periods and relative humidity's) on the resulting drug release kinetics.

Theophylline-loaded matrix cores were coated in a fluidized bed coater with aqueous dispersions of ethylcellulose (Aquacoat® ECD, plasticized with 25% triethylcitrate), with or without adding small amounts of a poly(vinylalcohol)-poly(ethyleneglycol)-graft-copolymer (Kollicoat® IR). The pellets were cured for 24/48 h at 60° C. and ambient relative humidity (RH); or for 24/48 h at 60° C. and 75% RH (followed by 24 h at 60° C. and ambient RH). In vitro drug release was measured in 0.1M HCl and phosphate buffer pH 7.4 at 37° C. in a USP paddle apparatus.

The addition of only small amounts of the poly(vinylalcohol)-poly(ethyleneglycol)-graft-copolymer to ethylcellulose-based film coatings significantly accelerated drug release from the coated pellets, irrespective of the pH of the release medium. For instance, 0, 2, 11, 64 and 96% theophylline were released after 4 hours of exposure to phosphate buffer pH 7.4 from pellets coated with ethylcellulose-based films containing 0, 5, 10, 15 and 20% of the poly(vinylalcohol)-poly(ethyleneglycol)-graft-copolymer (coating level 10%, curing conditions: 24 h at 60° C. and ambient RH). This can be attributed to a significant increase in the water uptake of the film coatings and to the leaching of the water-soluble polymer out of the films into the bulk fluid. Both effects result in increased permeability's of the coatings for the drug. In contrast to the addition of HPMC, the presence of the poly (vinylalcohol)-poly(ethyleneglycol)-graft-copolymer did not affect the stability of the coating dispersions.

Figure 15A:
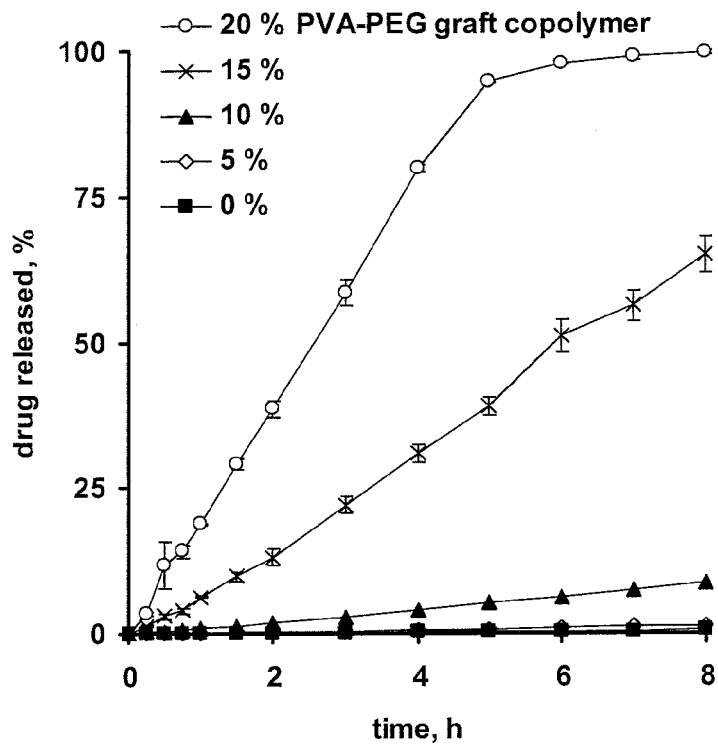
FIG. 15(a) shows theophylline release from pellets coated with ethylcellulose and blends of ethylcellulose with PVA-PEG graft copolymer upon exposure to 0.1M HCl at a coating level of 20% (w/w) after curing for 2 days at 60° C. and ambient relative humidity.
Figure 15B:
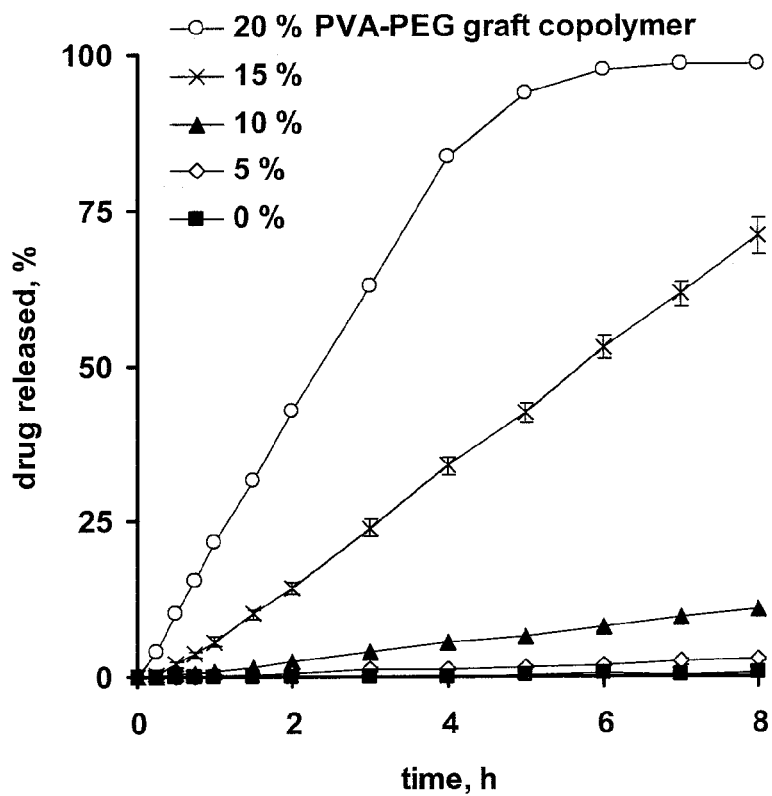
FIG. 15(b) shows theophylline release from pellets coated with ethylcellulose and blends of ethylcellulose with PVA-PEG graft copolymer upon exposure to phosphate buffer pH 7.4 at a coating level of 20% (w/w) after curing for 2 days at 60° C. and ambient relative humidity.

The release of theophylline from pellets coated with ethylcellulose-based films containing 0, 5, 10, 15 and 20% of the poly(vinylalcohol)-poly(ethyleneglycol)-graft-copolymer (PVA-PEG) (coating level: 20%, curing conditions: 2 days at 60° C. and ambient relative humidity) in simulated gastric and intestinal fluids is shown in FIGS. 15(a)-15(b). The addition of only small amounts of PVA-PEG graft copolymer significantly increases the release rate of the drug, independent of the pH of the release medium. Thus, desired release can be obtained by adjusting the PVA-PEG graft copolymer content in the ethylcellulose film.

Figure 15C:
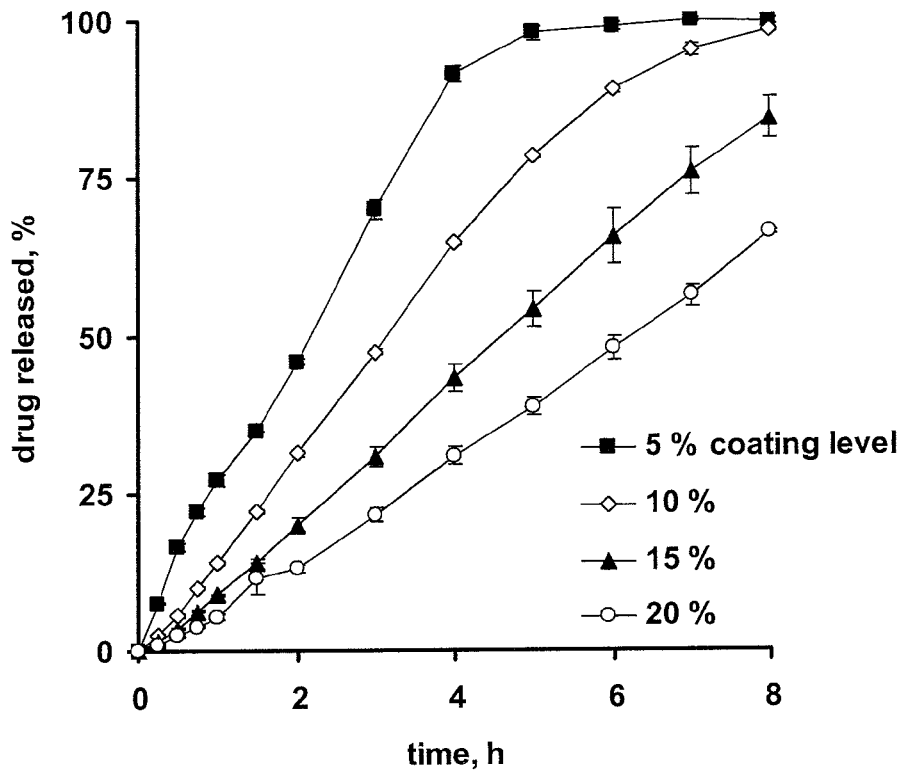
FIG. 15(c) shows the effects of coating level theophylline release from pellets coated with a blends of ethylcellulose with 15% (w/w) PVA-PEG graft copolymer upon exposure to 0.1M HCl after curing for 1 day at 60° C. and ambient relative humidity.
Figure 15D:
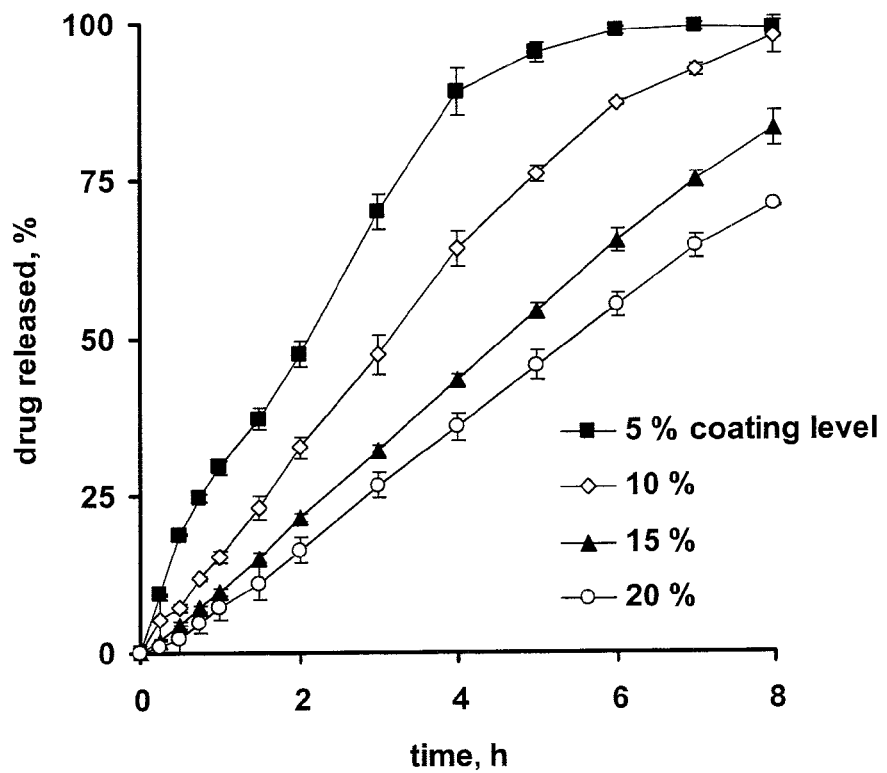
FIG. 15(d) shows the effects of coating level theophylline release from pellets coated with a blends of ethylcellulose with 15% (w/w) PVA-PEG graft copolymer upon exposure to phosphate buffer pH 7.4 after curing for 1 day at 60° C. and ambient relative humidity.

FIGS. 15(c)-15(d) show that the coating level of ethylcellulose blends with PVA-PEG graft copolymer can be varied to modify the drug release rate. Drug release rate from pellets coated with 85% ethylcellulose and 15% PVA-PEG graft copolymer decreases with increasing coating level. Higher coating levels offer the advantage of a more robust coating process. Thus, desired release rates can be easily and effectively adjusted by adding different amounts of PVA-PEG graft copolymer to ethylcellulose film coatings, as well as by varying the coating level.

The type of investigated curing conditions did not significantly alter the resulting drug release patterns. For example, 60(±3)% theophylline was released after 8 h exposure to 0.1M HCl from pellets coated with ethylcellulose-based films containing 15% of the poly(vinylalcohol)-poly(ethyleneglycol)-graft-copolymer (coating level=20%) upon curing for 24 or 48 hours at 60° C. and ambient RH or 75% RH. This can serve as an indicator that stable polymeric films were formed.

Figure 39A:
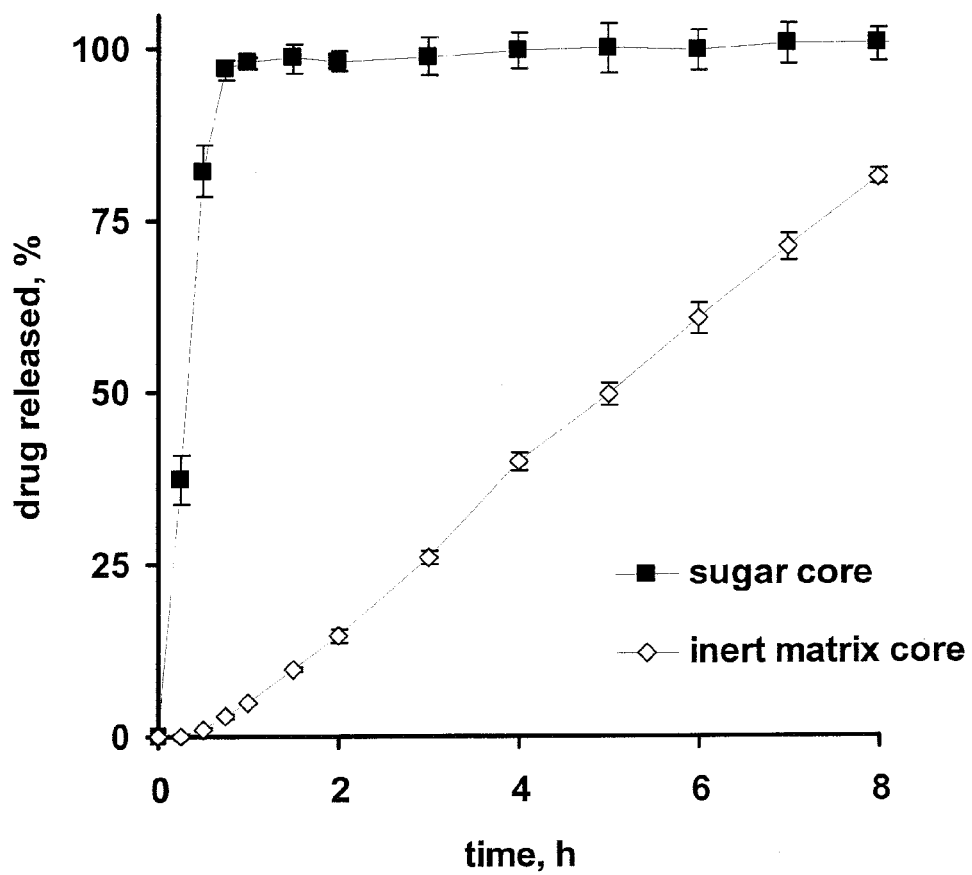
FIGS. 39(a)-39(b) show the effect of the type of bead core on the: 39(a) relative and 39(b) absolute theophylline release rate in phosphate buffer pH 7.4 from pellets coated with ethylcellulose:PVA-PEG graft polymer 85%:15% (w/w) blends with a coating level of 15%, and curing for 1 day at 60° C.
Figure 39B:
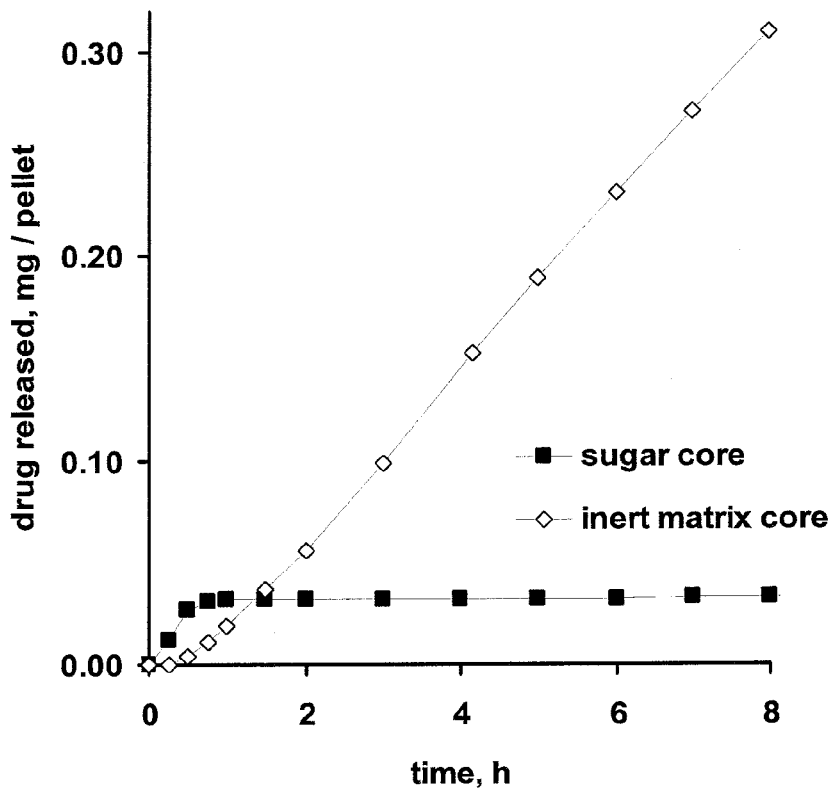
Figure 40:
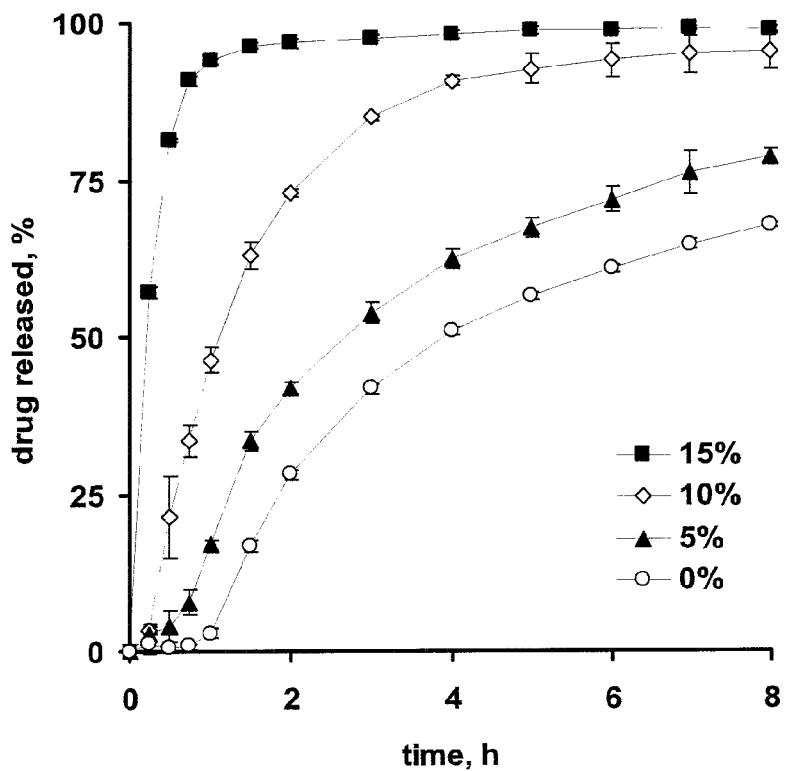
FIG. 40 shows the effect of the PVA-PEG-graft-copolymer content (indicated in the figure) on diltiazem-HCl release in 0.1M HCl from drug-layered sugar cores coated with ethylcellulose:PVA-PEG-graft-copolymer blends (curing: 1 day at 60° C., coating level: 15%).

FIGS. 39(*a*)-39(*b*) show the effects of the type of bead core on the relative and absolute theophylline release rate in phosphate buffer pH 7.4 from pellets coated with ethylcellulose: PVA:PEG graft copolymer. The type of pellet core affected the resulting relative and absolute drug release kinetics indicating differences in the mass transport mechanisms. Importantly, broad ranges of release patterns could be obtained by varying the PVA:PEG graft copolymer content from 5-15% by weight, and the coating level (5-10% by weight) irrespective of the type of drug and type of core. FIG. 40 exemplarily shows the release of diltiazem-HCl from drug-layered sugar cores coated with ethylcellulose dispersions containing different amounts of PVA-PEG graft copolymer in 0.1M HCl.

Figure 41:
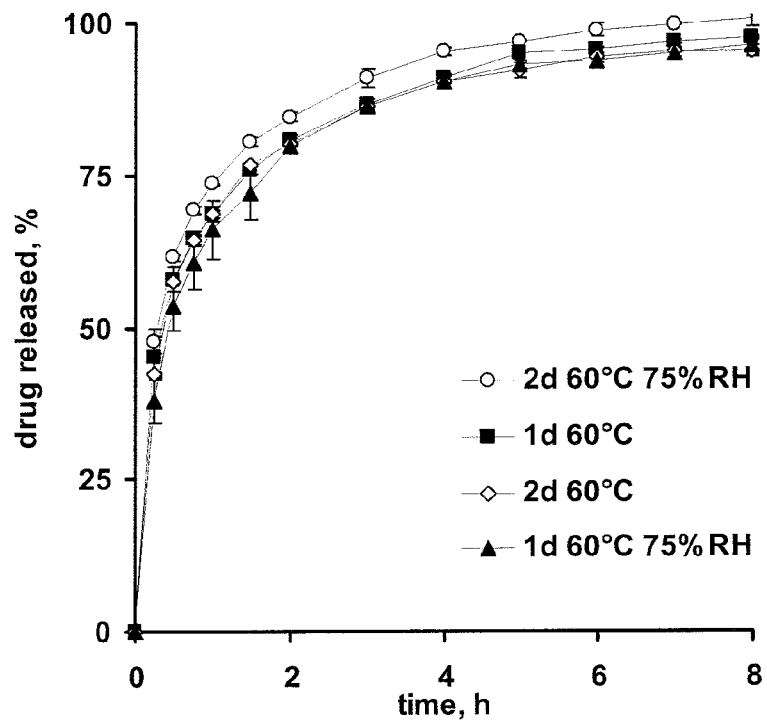
FIG. 41 shows the effect of the curing conditions (indicated in the figure) on diltiazem-HCl release in phosphate buffer pH 7.4 from drug-layered sugar cores coated with ethylcellulose:PVA-PEG-graft-copolymer 85%:15% (w/w) blends at a coating level of 15%.
Figure 42:
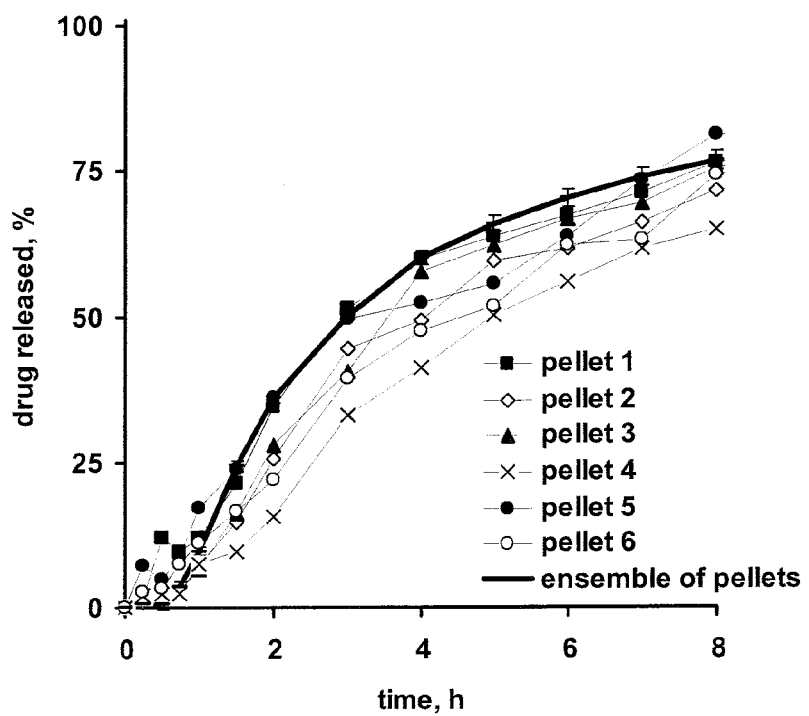
FIG. 42 shows diltiazem-HCl release in phosphate buffer pH 7.4 from single pellets (drug-layered sugar cores), coated with ethylcellulose:PVA-PEG-graft-copolymer 95:05 blends (curing: 1 day at 60° C., coating level: 15%).
Figure 43A:
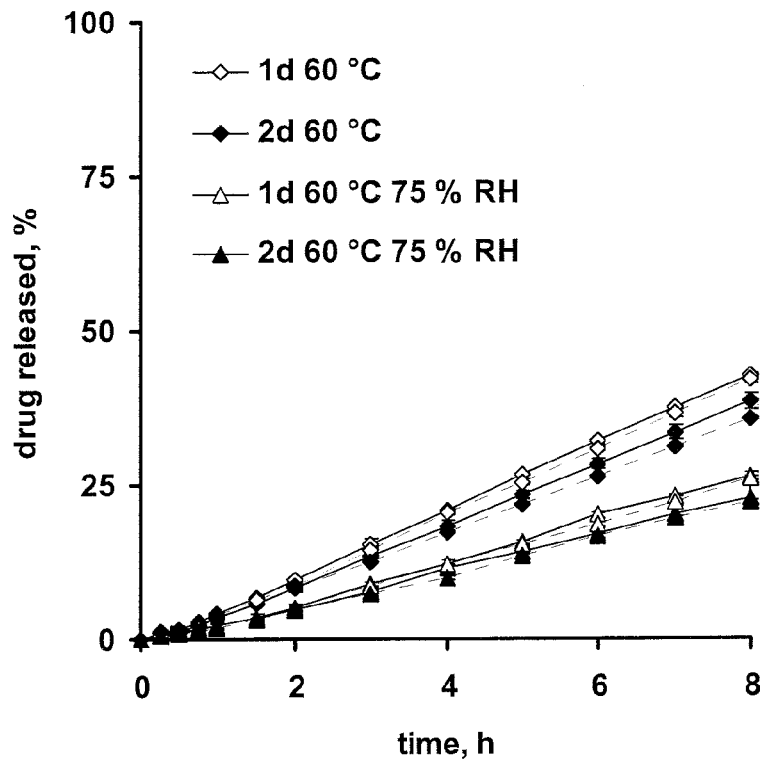
FIGS. 43(a)-43(b) show theophylline release from pellets coated with ethylcellulose:PG alginate 90:10 blends in 0.1M HCl before (dotted curves) and after (solid curves) 6 months storage at: 43(a) room temperature, and 43(b) 40° C. and 75% RH (coating level: 20%, the curing conditions are indicated in the figures).
Figure 43B:
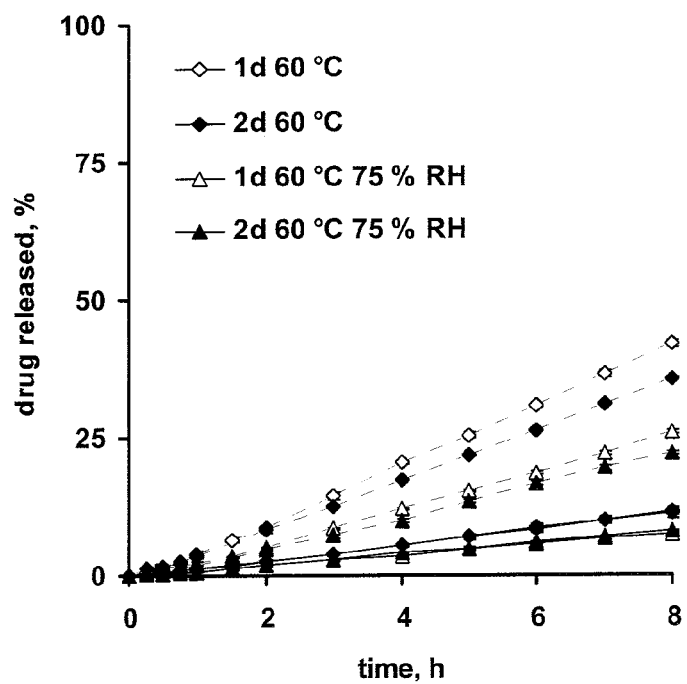
Figure 44A:
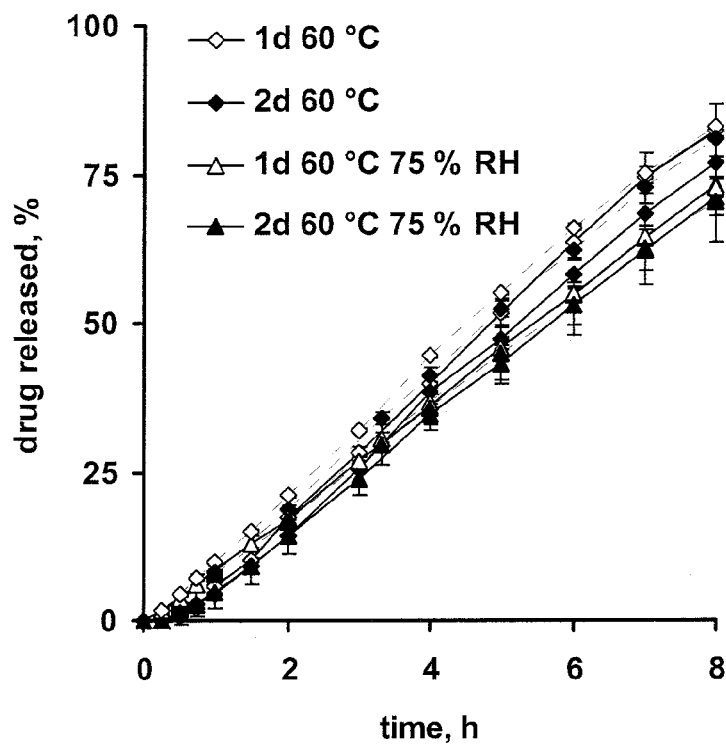
FIGS. 44(a)-44(b) show theophylline release from pellets coated with ethylcellulose:PG alginate 90:10 blends in phosphate buffer pH 7.4 before (dotted curves) and after (solid curves) 6 months storage at: 44(a) room temperature, and 44(b) 40° C. and 75% RH (coating level 20%, the curing conditions are indicated in the figures).
Figure 44B:
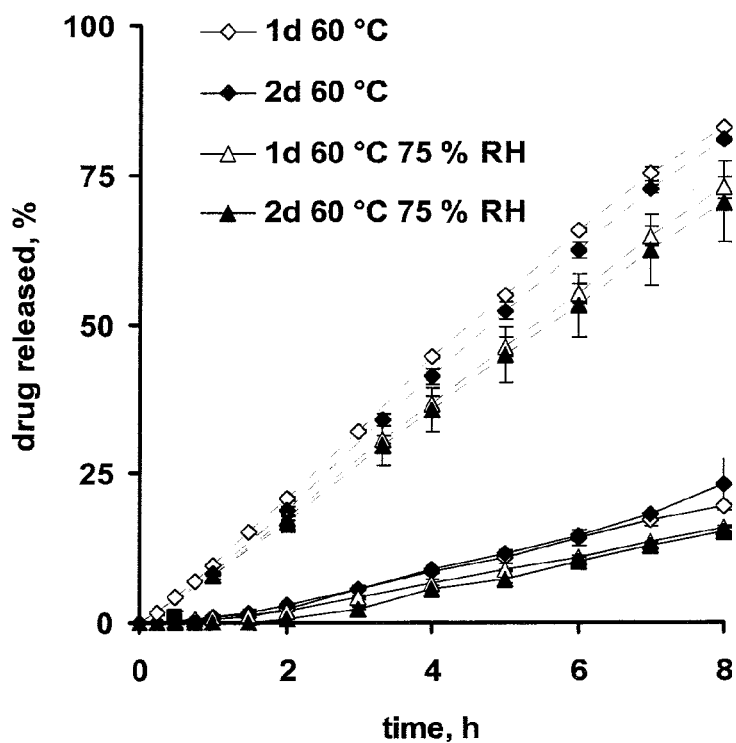

Also, the type of curing conditions did not affect the resulting drug release kinetics as shown in FIG. 41, indicating that stable film coatings were achieved. Furthermore, drug release from single pellets revealed that the observed release profiles from ensembles of coated beads are not a summation of the individual pulsatile release patters, as shown in FIG. 42. The individual pellets release the drug in a similar way.

Drug release did not depend on the pH of the release medium In conclusion, desired drug release profiles from ethylcellulose-coated pellets can effectively be adjusted by adding only small amounts of a poly(vinylalcohol)-poly(ethyleneglycol)-graft-copolymer. Importantly, the stability of the coatings dispersions is not affected and stable film coatings seem to be achieved after appropriate curing.

Carrageenan as an Efficient Modulator for the Properties of Ethylcellulose-Based Films Due to its chemical structure carrageenan is a promising candidate to render ethylcellulose-based films more hydrophilic and, thus, more permeable for many drugs. The major objectives of this study were: (i) to evaluate the potential of carrageenan as an effective modulator for the properties of ethylcellulose-based films; and (ii) to quantitatively describe the observed water uptake and drug release kinetics of/from ethylcellulose-based films using Fick's second law of diffusion.

Thin films were prepared by casting aqueous dispersions of ethylcellulose (Aquacoat® ECD, plasticized with 25% triethylcitrate) and carrageenan (Viscarin® GP 209) onto Teflon® plates and controlled drying. Drug-containing films were prepared accordingly, adding theophylline to the aqueous dispersions. The drug loading was below the solubility of theophylline in the polymeric systems (monolithic solutions). The water uptake and dry weight loss kinetics of the films were measured gravimetrically upon exposure to 0.1M HCl and phosphate buffer pH 7.4. In vitro drug release was monitored in the same media (37° C., UV drug detection). The apparent diffusion coefficients of water and theophylline in the polymeric systems were determined by fitting an analytical solution of Fick's second law of diffusion to the experimentally measured water uptake and drug release kinetics. Importantly, the addition of only 2.5% carrageenan to the ethylcellulose-based films resulted in a 4-fold increase in the extent of water uptake upon exposure to 0.1M HCl. This renders the films much more permeable for the drug.

The water penetration kinetics could be quantitatively described using Fick's second law of diffusion. The apparent diffusion coefficients of water were determined to be 1.5, 5.3, 7.8 and $9.2 \times 10^{-8}$ cm$^2$/s for films containing 0, 2.5, 5 and 10% carrageenan. In addition, the presence of carrageenan in the systems significantly increased the extent and rate of the dry weight loss of the films upon exposure to 0.1M HCl and phosphate buffer pH 7.4. Both, the increased water content as well as dry weight loss resulted in a tremendous increase in the permeability of the films for the drug.

For instance, the apparent diffusion coefficient of theophylline increased from 0.3 to 2.5, 3.6 and $5.1 \times 10^{-8}$ cm$^2$/s when adding 2.5, 5 and 10% carrageenan (upon exposure to phosphate buffer pH 7.4). Importantly, and in contrast to HPMC, the aqueous ethylcellulose dispersions were stable in the presence of carrageenan. As the addition of only small amounts of carrageenan significantly alters the properties of ethylcellulose-based film coatings and at the same time provides stable coating dispersions, it is a very promising modulator for the release kinetics from ethylcellulose-coated dosage forms. FIGS. 16(*a*)-16(*d*) illustrate the release of theophylline from pellets coated with ethylcellulose and with blends of ethylcellulose and carrageenan in simulated gastric and intestinal fluids at 10% (w/w) and 20% (w/w) coating levels. Clearly, the presence of small amounts of carrageenan effectively increases the resulting drug release rates, irrespective of the type of release medium and coating level. In practice, desired release profiles can be provided by adjusting the relative carrageenan content.

FIGS. 16(*e*)-16(*f*) show theophylline release from pellets coated with 90% ethylcellulose and 10% carrageenan, PVA-PEG graft copolymer and PG alginate in 0.1M HCl and phosphate buffer pH 7.4 at a coating level of 20% (w/w). From this, it can be seen that of these materials, carrageenan is the most efficient drug release modifier.

For long term storage stability, in some cases curing is conducted at elevated relative humidity in order to facilitate film formation. FIGS. 16(*g*)-16(*j*) show the release of theophylline from cured pellets coated with ethylcellulose containing 5% (w/w) of carrageenan at 10% (w/w) and 20% (w/w) coating levels in simulated gastric and intestinal fluids. Two different sets of curing conditions were employed: (1) 1 or 2 days at 60° C. and ambient relative humidity, and (2) 1 or 2 days at 60° C. and 75% relative humidity, followed by one day at 60° C. and ambient relative humidity for drying. Drug release from uncured pellets is also shown for comparison. Based on these results, it can be concluded that curing may be required for this type of film coating to promote long term storage stability.

FIGS. 16(*k*)-16(*r*) show the release rates of theophylline in simulated gastric and intestinal fluids (0.1M HCl and phosphate buffer pH 7.4) from coated pellets. FIGS. 16(*k*)-16(*r*) show a slight pH dependence of drug release when 5% (w/w) carrageenan is present in the film coatings, whereas the pH dependence is essentially negligible at 10% (w/w) carrageenan content, independent of coating level and curing time.

As carrageenan contains free sulfate groups, the permeability of polymeric films containing this biomacromolecule is susceptible to be affected by the concentration of (bivalent) calcium ions in the release medium: $Ca^{2+}$ ions can cross-link —$SO_3^-$ groups, resulting in a denser structure of the polymer network and, thus, decreased dug release rates. The $Ca^{2+}$ ion concentration in the contents of the gastro-intestinal tract can vary as a function of the food composition (e.g., milk is rich in calcium). For this reason it was interesting to see whether the addition of different amounts of $Ca^{2+}$ ions affect the resulting drug release kinetics from ethylcellulose:carrageenan-coated pellets. As it can be seen in FIGS. 16(s)-16(t), theophylline release slightly/moderately slowed down in 0.1M HCl/demineralized water when adding up to 50 mmol/L $Ca^{2+}$ ions (Remark: phosphate buffer pH 7.4 could not be used for these experiments, because calcium phosphate precipitates under these conditions). The fact that the decrease in drug release rate is less pronounced at low pH than at high pH can be explained by the higher degree of protonation of the free sulfate groups in carrageenan (non-charged sulfate groups are not available for cross-linking via $Ca^{2+}$ ions).

Figures 16A, 16B, 16C, 16D:
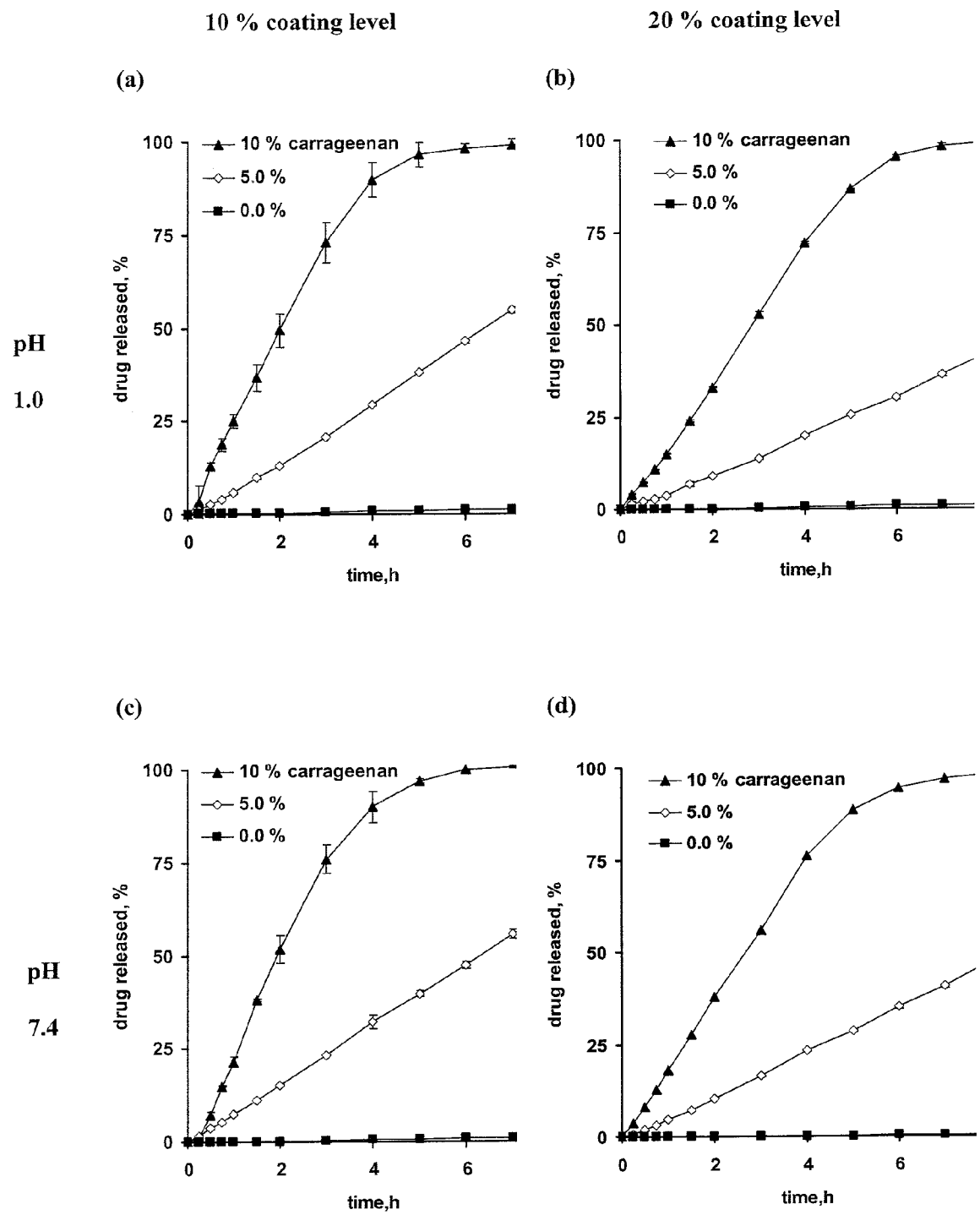
FIG. 16(a) illustrates the release of theophylline from pellets coated with ethylcellulose and with blends of ethylcellulose and carrageenan in 0.1M HCl at a 10% (w/w) coating level.
FIG. 16(b) illustrates the release of theophylline from pellets coated with ethylcellulose and with blends of ethylcellulose and carrageenan in 0.1M HCl at a 20% (w/w) coating level.
FIG. 16(c) illustrates the release of theophylline from pellets coated with ethylcellulose and with blends of ethylcellulose and carrageenan in phosphate buffer pH 7.4 at a 10% (w/w) coating level.
FIG. 16(d) illustrates the release of theophylline from pellets coated with ethylcellulose and with blends of ethylcellulose and carrageenan in phosphate buffer pH 7.4 at a 20% (w/w) coating level.
Figure 16E:
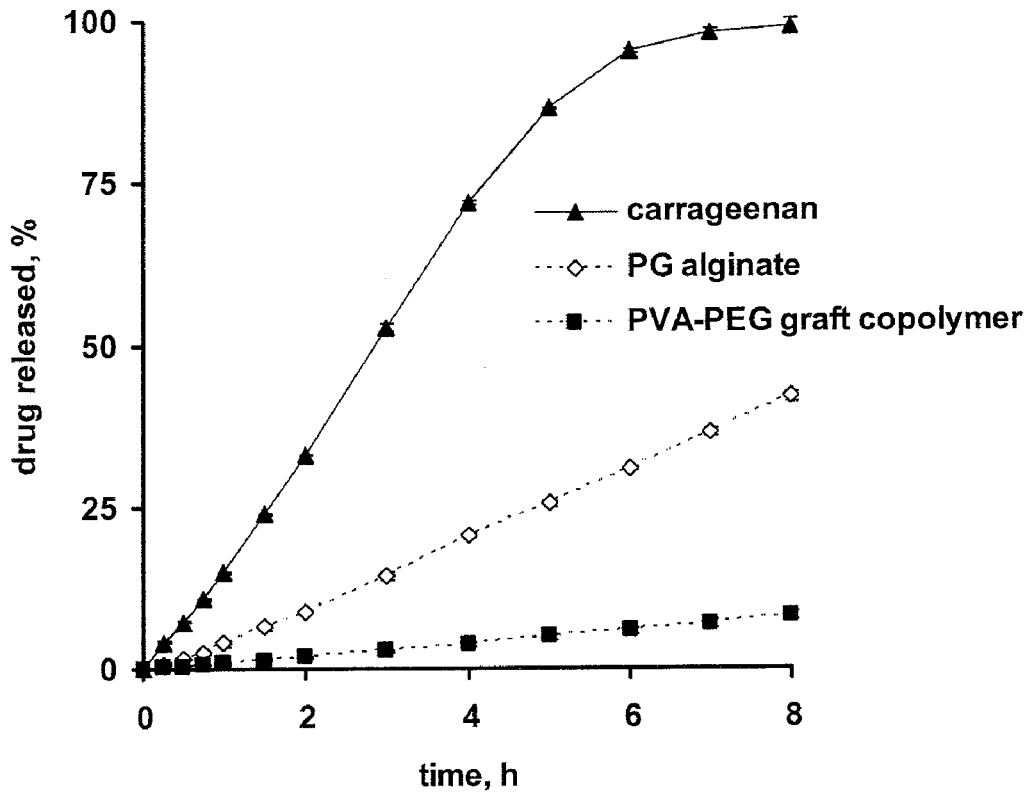
FIG. 16(e) shows theophylline release from pellets coated with 90% ethylcellulose and 10% carrageenan, PVA-PEG graft copolymer and PG alginate in 0.1M HCl at a coating level of 20% (w/w).
Figure 16F:
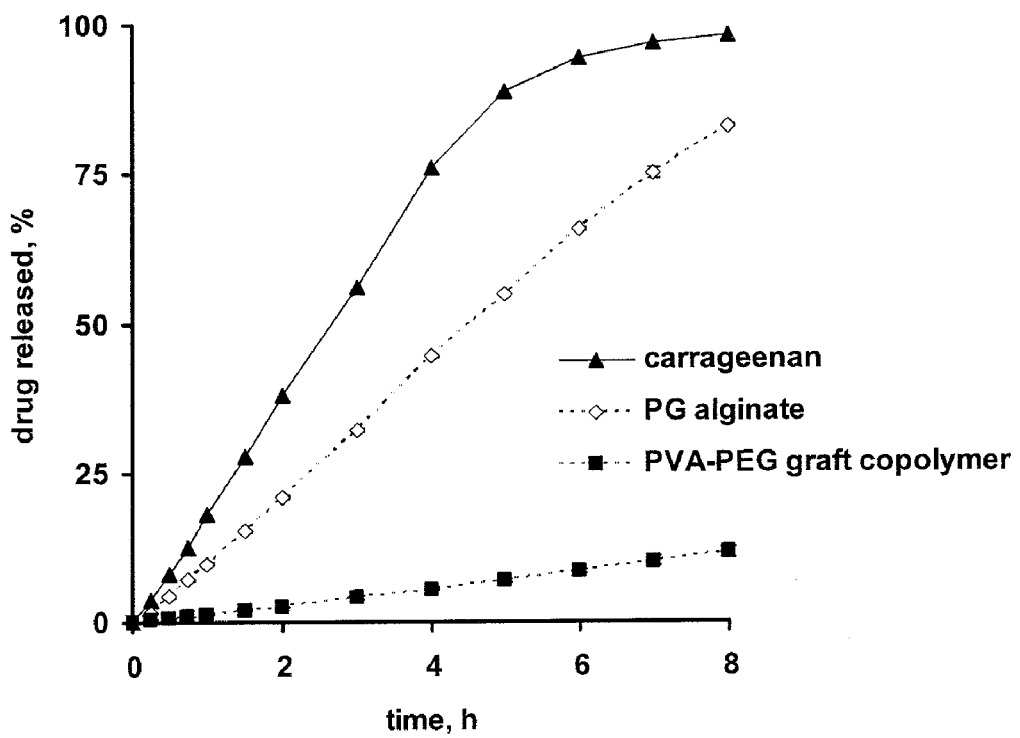
FIG. 16(f) shows theophylline release from pellets coated with 90% ethylcellulose and 10% carrageenan, PVA-PEG graft copolymer and PG alginate in phosphate buffer pH 7.4 at a coating level of 20% (w/w).
Figures 16K, 16L, 16M, 16N:
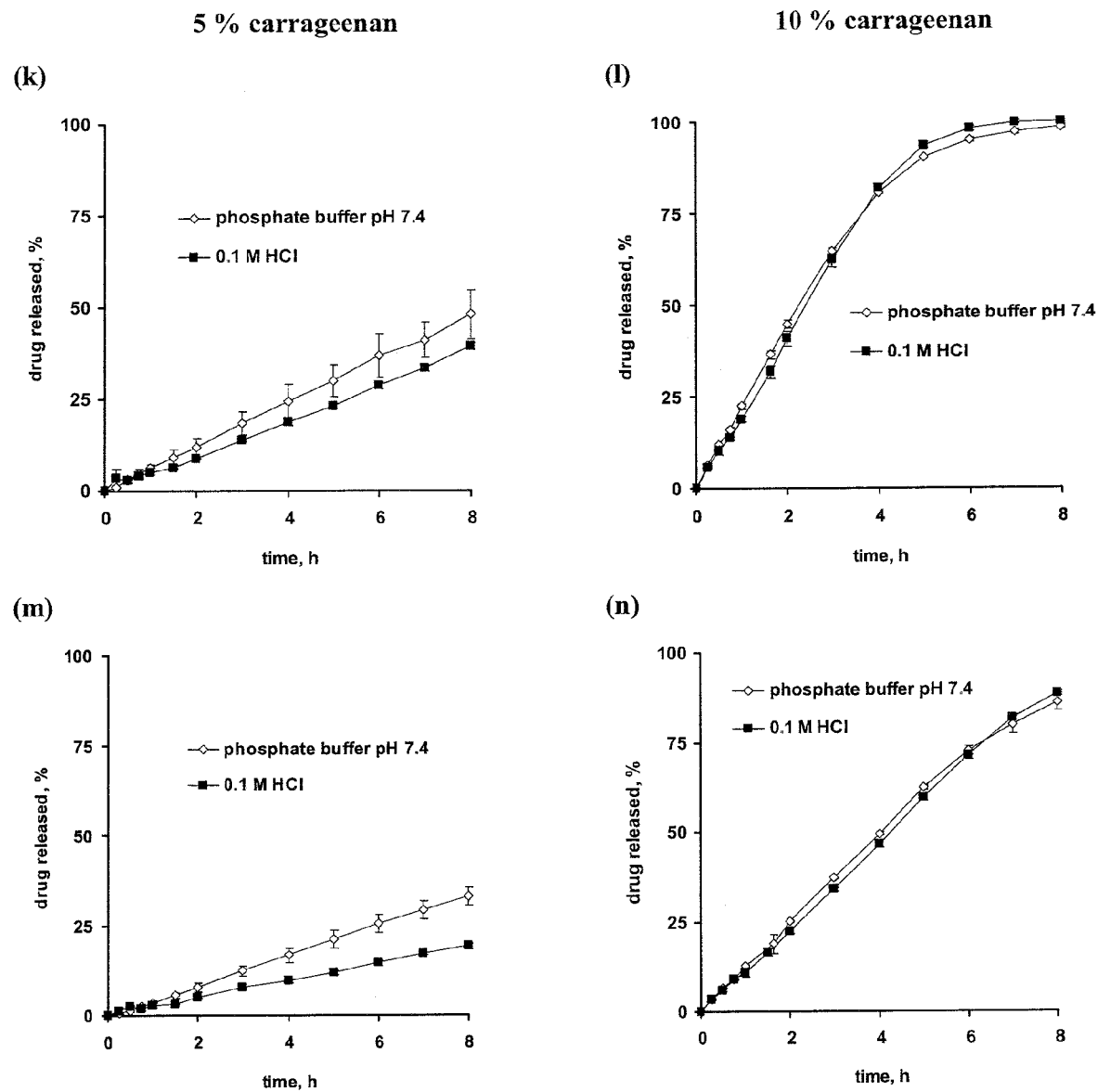
FIG. 16(k) shows the release rate of theophylline coated at a 10% (w/w) coating level with ethylcellulose containing 5% (w/w) carrageenan in simulated gastric and intestinal fluids cured for 1 day at 60° C. and 75% relative humidity.
FIG. 16(l) shows the release rate of theophylline coated at a 10% (w/w) coating level with ethylcellulose containing 10% (w/w) carrageenan in simulated gastric and intestinal fluids cured for 1 day at 60° C. and 75% relative humidity.
FIG. 16(m) shows the release rate of theophylline coated at a 20% (w/w) coating level with ethylcellulose containing 5% (w/w) carrageenan in simulated gastric and intestinal fluids cured for 1 day at 60° C. and 75% relative humidity.
FIG. 16(n) shows the release rate of theophylline coated at a 20% (w/w) coating level with ethylcellulose containing 10% (w/w) carrageenan in simulated gastric and intestinal fluids cured for 1 day at 60° C. and 75% relative humidity.
Figure 16O:
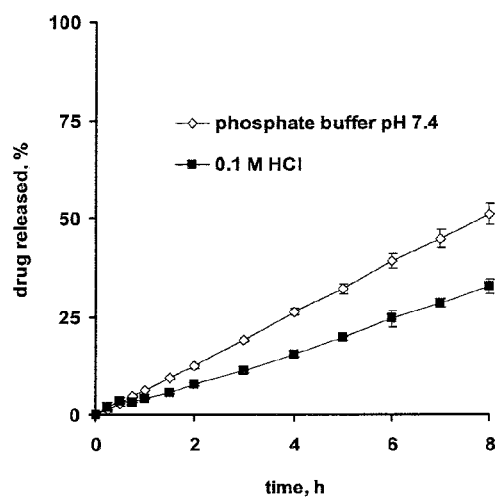
FIG. 16(o) shows the release rate of theophylline coated at a 10% (w/w) coating level with ethylcellulose containing 5% (w/w) carrageenan in simulated gastric and intestinal fluids cured for 2 days at 60° C. and 75% relative humidity.
Figure 16P:
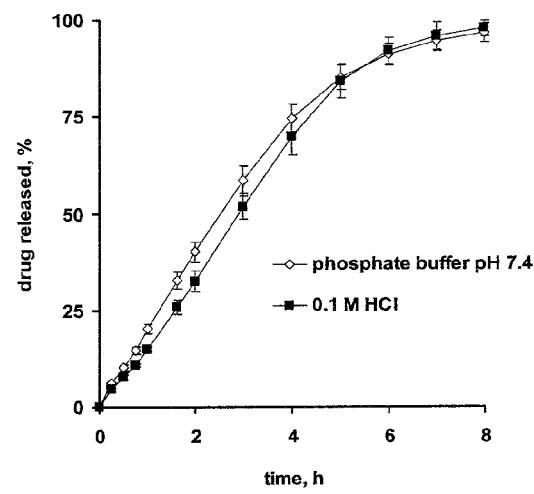
FIG. 16(p) shows the release rate of theophylline coated at a 10% (w/w) coating level with ethylcellulose containing 10% (w/w) carrageenan in simulated gastric and intestinal fluids cured for 2 days at 60° C. and 75% relative humidity.
Figure 16Q:
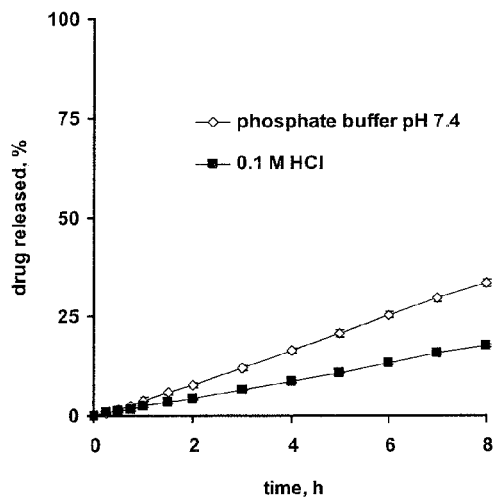
FIG. 16(q) shows the release rate of theophylline coated at a 20% (w/w) coating level with ethylcellulose containing 5% (w/w) carrageenan in simulated gastric and intestinal fluids cured for 2 days at 60° C. and 75% relative humidity.
Figure 16R:
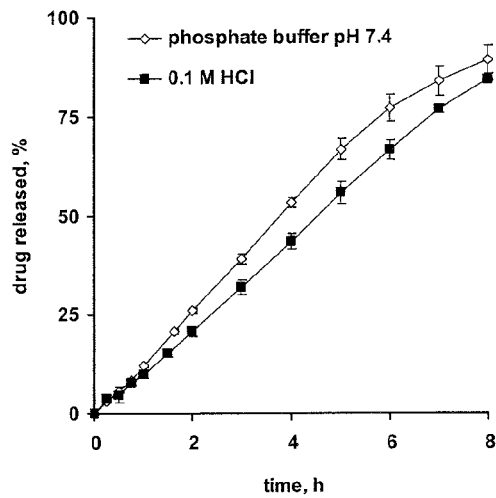
FIG. 16(r) shows the release rate of theophylline coated at a 20% (w/w) coating level with ethylcellulose containing 10% (w/w) carrageenan in simulated gastric and intestinal fluids cured for 2 days at 60° C. and 75% relative humidity.
Figure 16S:
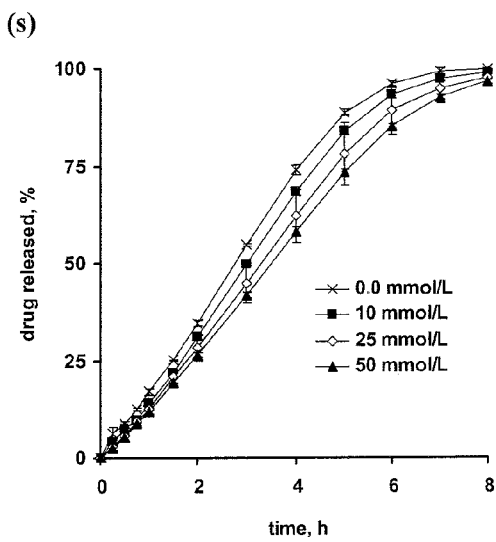
FIGS. 16(s)-16(x) show the effects of the calcium ion concentration in the release medium (indicated in the figures) on theophylline release from pellets coated with ethylcellulose containing: 16(s) 10% carrageenan, in 0.1M HCl; 16(t) 10% carrageenan, in dematerialized water; 16(u) 10% PG alginate, in 0.1M HCl; 16(v) 10% PG alginate, in demineralized water; 16(w) 15% PVA-PEG graft copolymer, in 0.1M HCl; 16(x) 15% PVA-PEG graft copolymer, in demineralized water (20% coating level; curing=1 day at 60° C. & ambient relative humidity).
Figure 16T:
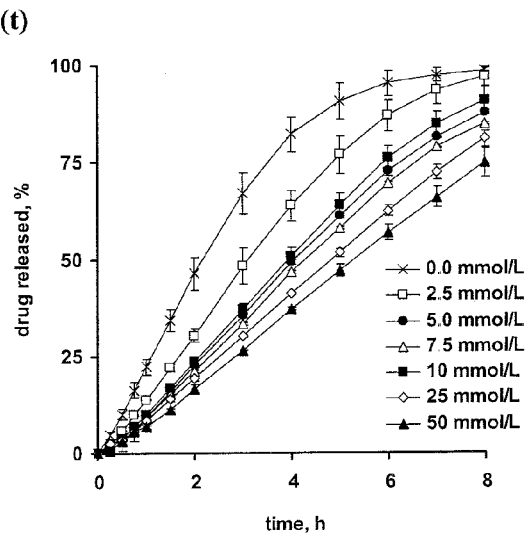
Figures 16U, 16V, 16W, 16X:
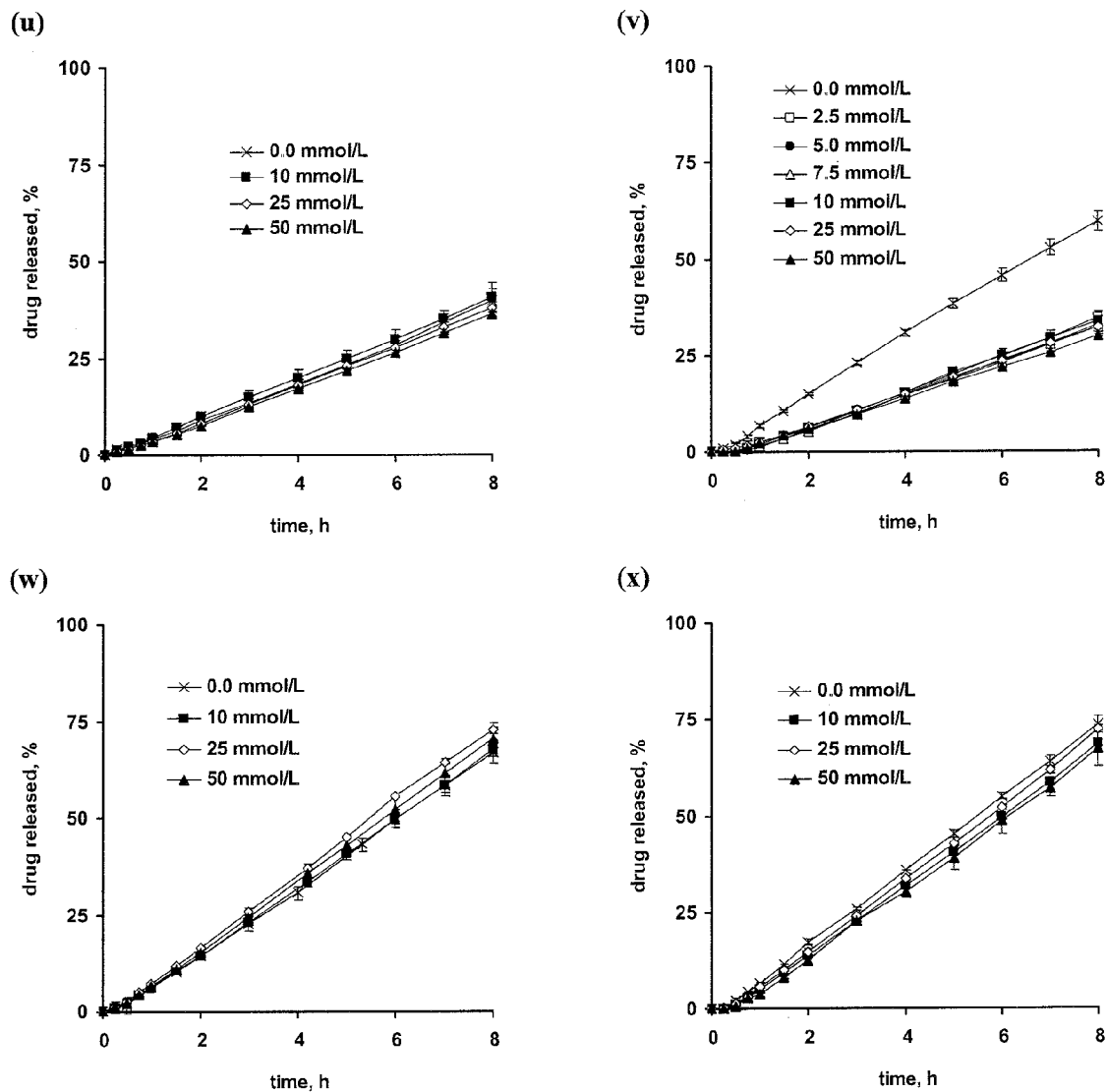
Figure 17:
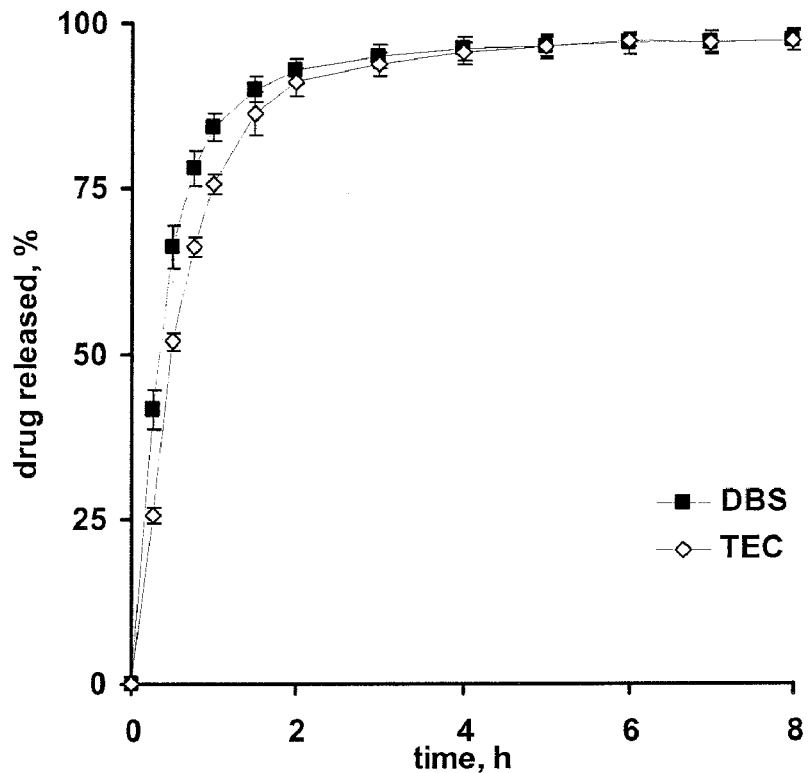
FIG. 17 shows the effects of the type of plasticizer on diltiazem-HCl release in 0.1M HCl from pellets coated with Aquacoat® ECD/Kollicoat® IR 95/05 blends (coating level: 5%; curing: for 1 day at 60° C.).
Figure 18:
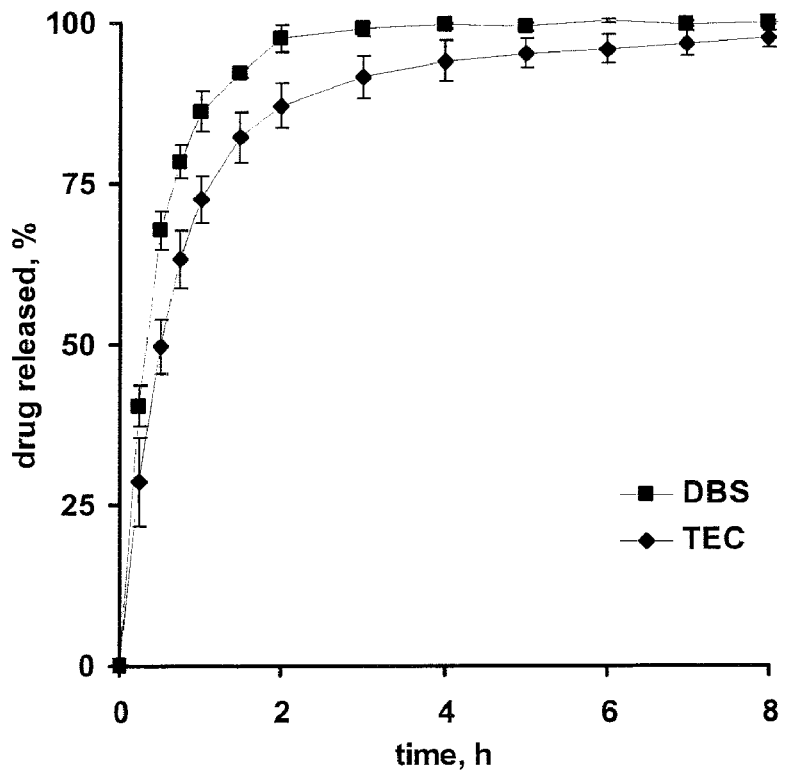
FIG. 18 shows the effects of the type of plasticizer on diltiazem-HCl release in phosphate buffer pH 7.4 from pellets coated with Aquacoat® ECD/Kollicoat® IR 95/05 blends (coating level: 5%; curing for one 1 day at 60° C.)
Figure 19:
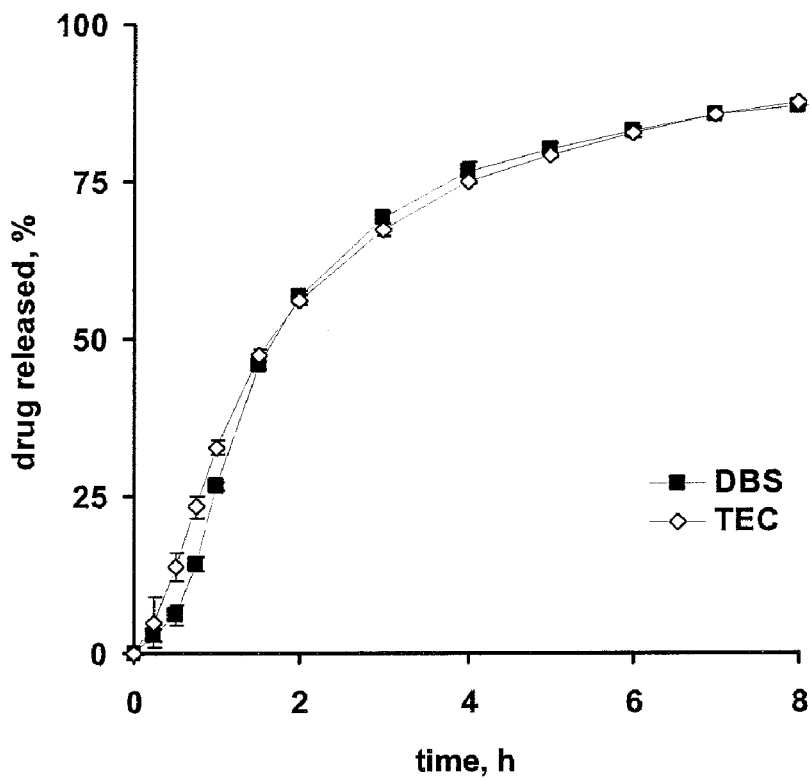
FIG. 19 shows the effects of the type of plasticizer on diltiazem-HCl release in 0.1M HCl from pellets coated with Aquacoat® ECD/Kollicoat® IR 95/05 blends (coating level: 10%; curing for 1 day at 60° C.).
Figure 20:
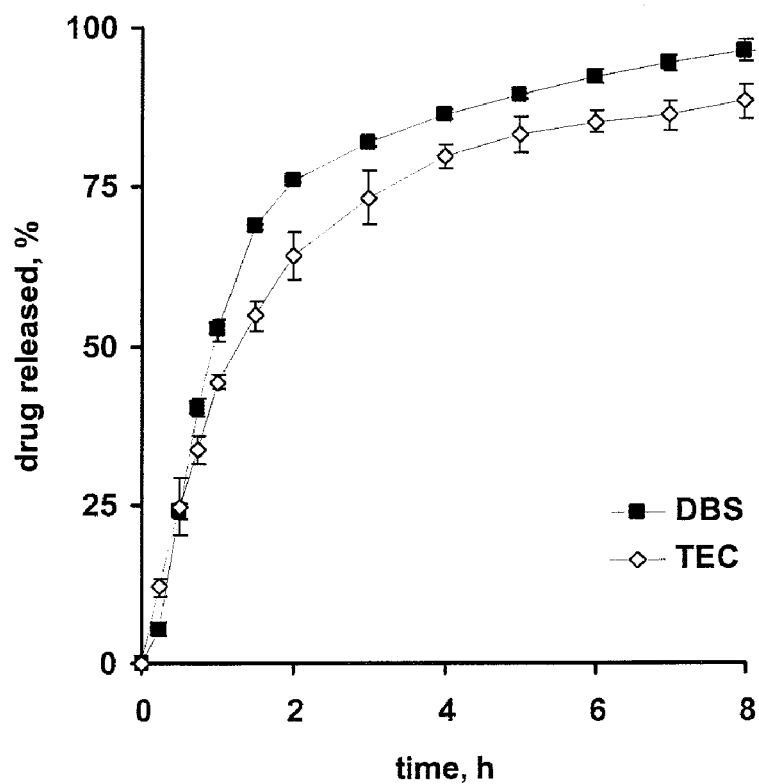
FIG. 20 shows the effects of the type of plasticizer on diltiazem-HCl release in phosphate buffer pH 7.4 from pellets coated with Aquacoat® ECD/Kollicoat® IR 95/05 blends (coating level: 10%; curing for 1 day at 60° C.).
Figure 21:
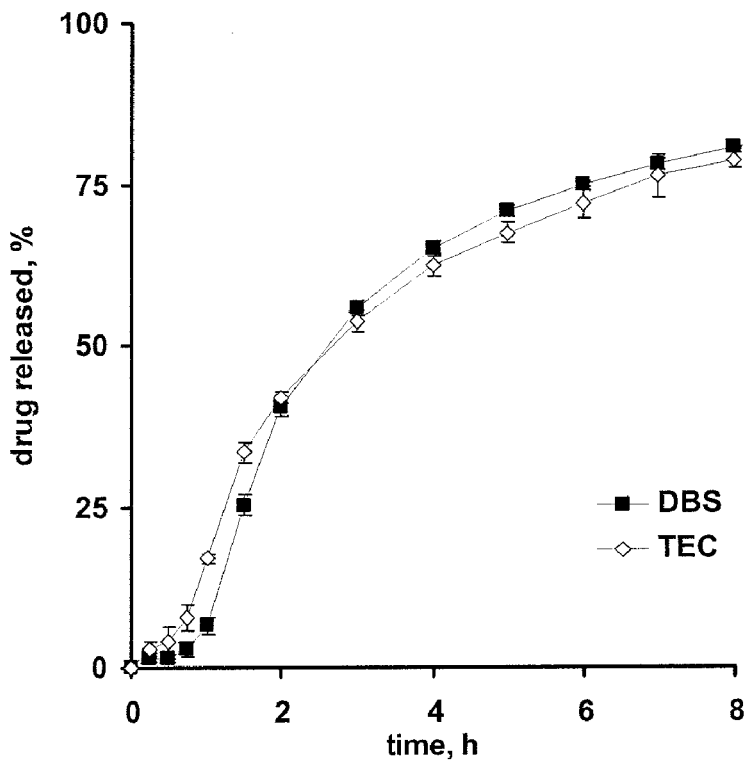
FIG. 21 shows the effects of the type of plasticizer on diltiazem-HCl release in 0.1M HCl from pellets coated with Aquacoat® ECD/Kollicoat® IR 95/05 blends (coating level: 15%; curing for 1 day at 60° C.).
Figure 22:
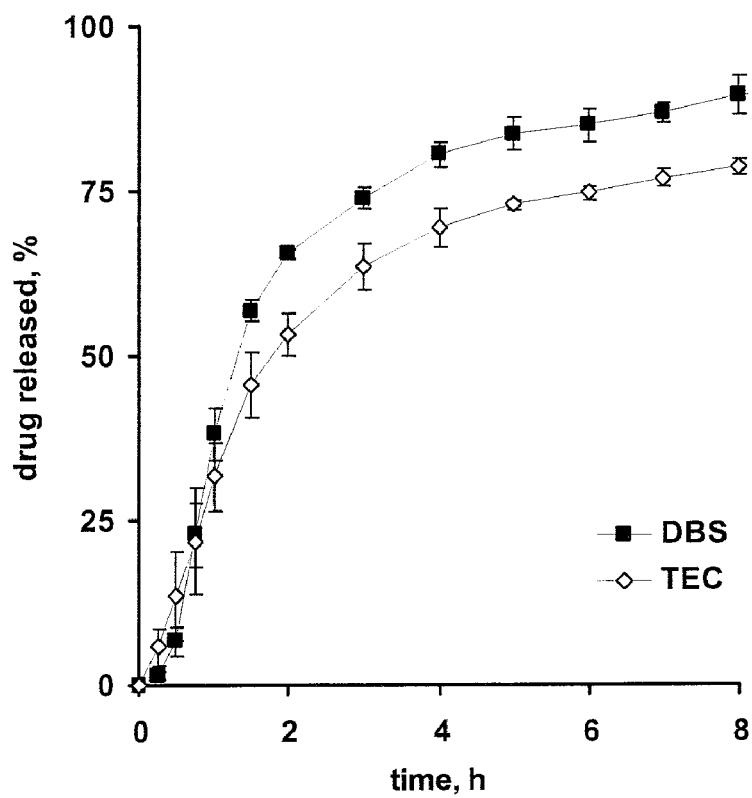
FIG. 22 shows the effects of the type of plasticizer on diltiazem-HCl release in phosphate buffer pH 7.4 from pellets coated with Aquacoat® ECD/Kollicoat® IR 95/05 blends (coating level: 15%; curing for 1 day at 60° C.).

For reasons of comparison, also the $Ca^{2+}$ ion-sensitivity of theophylline release from pellets coated with ethylcellulose containing 10% (w/w) PG alginate or 15% (w/w) PVA-PEG graft copolymer was studied in 0.1M HCl and demineralized water (FIGS. 16(u)-16(v)). Clearly, the sensitivity of ethylcellulose:PG alginate coatings is less pronounced than that of ethylcellulose:carrageenan coatings. In demineralized water, the release rate slightly/moderately decreases with increasing $Ca^{2+}$ ion concentration due to cross-linking of free $-COO^-$ groups present in PG alginate. In contrast, there is no effect in 0.1M HCl, because the carboxylic groups are mostly protonated and, thus, not available for cross-linking. The synthetic PVA-PEG graft copolymer (not containing any groups that can be negatively charged at low or high pH) did not show any $Ca^{2+}$ ion-sensitivity (FIGS. 16(w)-16(x)).

Effect of Different Types of Plasticizer

Studies were undertaken on the effects of the type of plasticizer on diltiazem-HCl release in 0.1M HCl from pellets coated with Aquacoat® ECD/Kollicoat® IR 95/05 blends (coating level: 5%; curing: 1 day at 60° C.). The results are given in FIGS. 17-22. Adding different amounts of a poly(vinyl alcohol)-poly(ethylene glycol)-graft-copolymer to ethylcellulose-based film coatings, broad ranges of release patterns can be achieved, irrespective of the water-solubility of the drug as well as of the osmotic activity of the pellet core.

Effect of Kollicoat® IR Content on Drug Release

Figure 23:
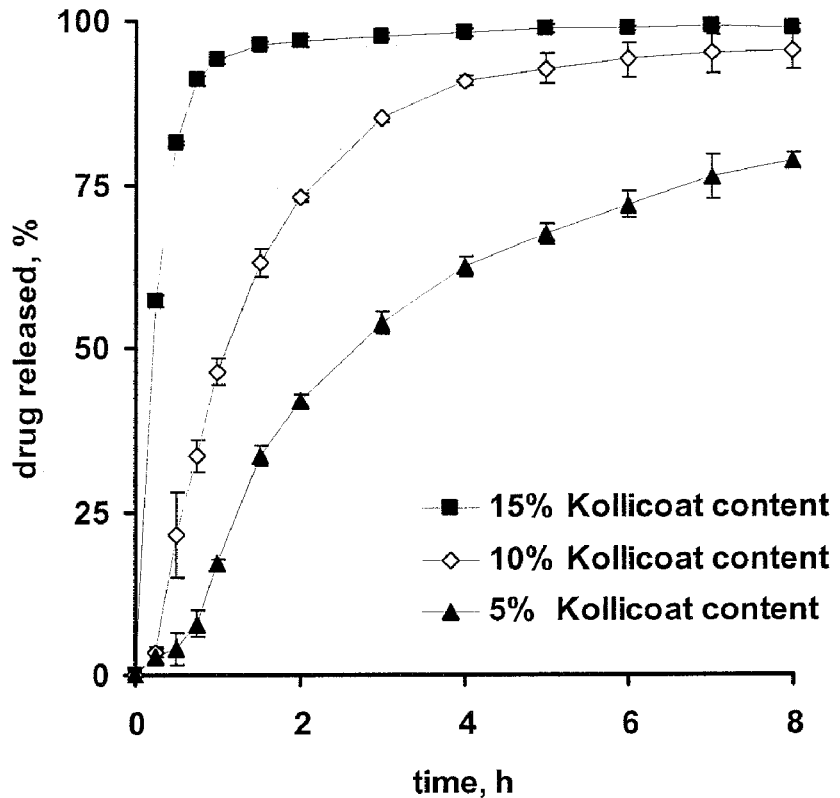
FIG. 23 shows the effects of the Kollicoat® IR content on diltiazem-HCl release in 0.1M HCl from pellets coated with Aquacoat® ECD/Kollicoat® IR 95/05 blends (coating level: 15%; curing for 1 day at 60° C. plasticizer: TEC, drug loading: 10%).
Figure 24:
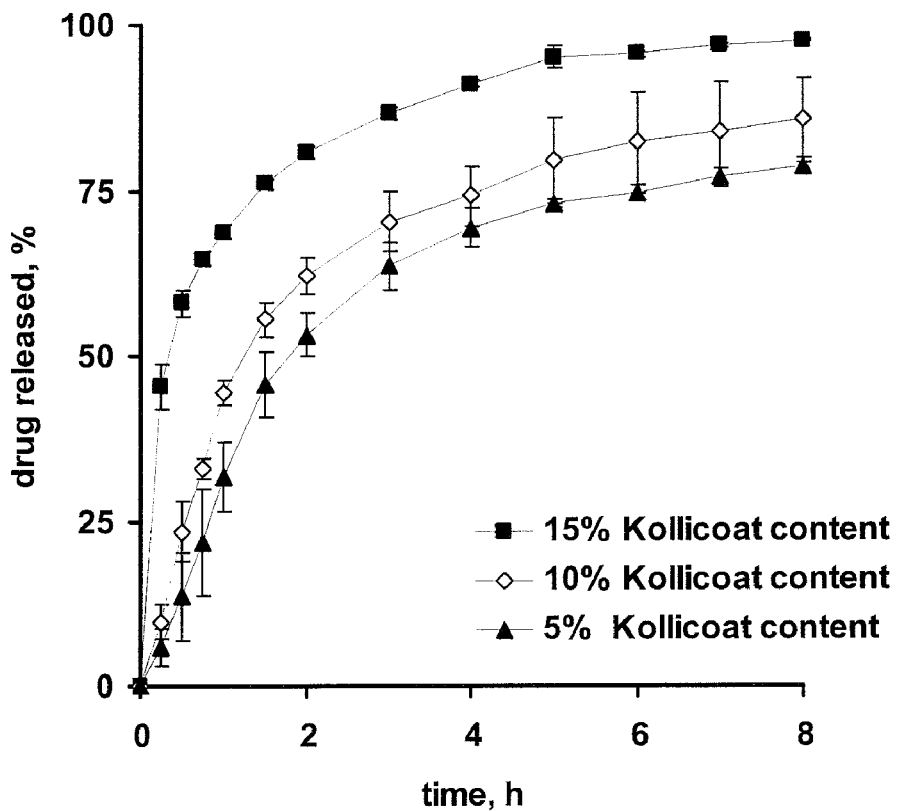
FIG. 24 shows the effects of the Kollicoat® IR content on diltiazem-HCl release in phosphate buffer pH 7.4 from pellets coated with Aquacoat® ECD/Kollicoat® IR 95/05 blends (coating level: 15%; curing for 1 day at 60° C., plasticizer: TEC, drug loading: 10%).

The effects of the Kollicoat® IR content on diltiazem-HCl release in 0.1M HCl from pellets coated with Aquacoat® ECD/Kollicoat® blends is shown in FIGS. 23-24.

Effect of Single Pellet Release

Figure 25:
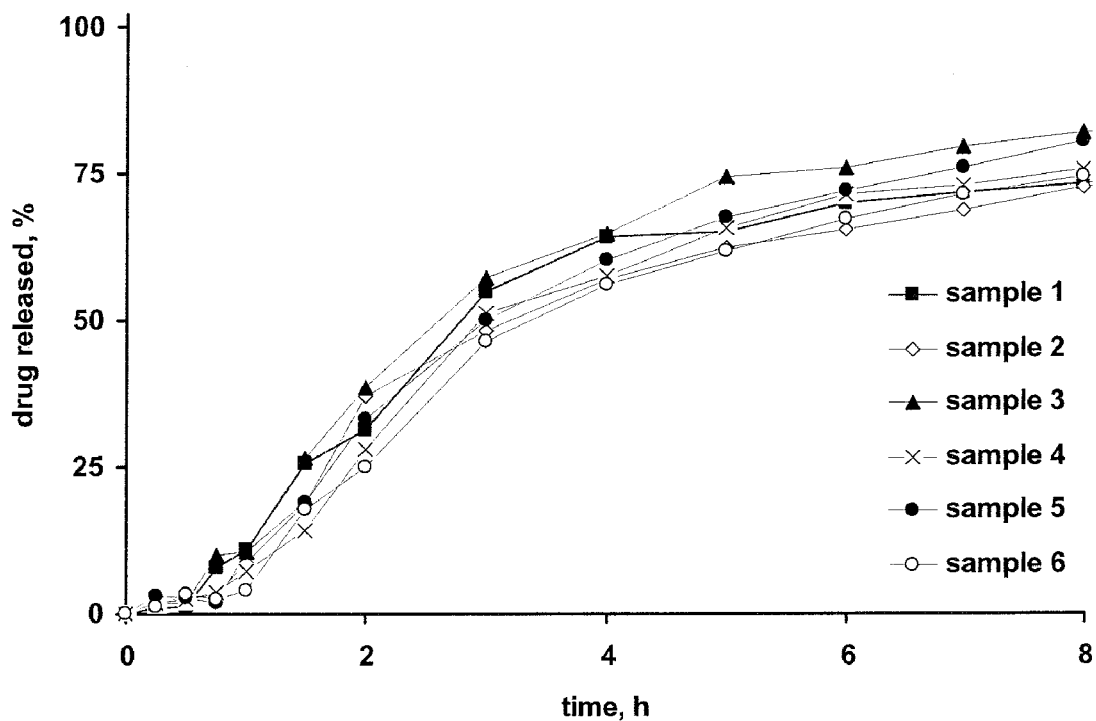
FIG. 25 shows the effects of Diltiazem-HCl release in 0.1M HCl from single pellets, coated with Aquacoat® ECD/Kollicoat® IR 95/05 blends with a coating level of 15% (curing for 1 day 60° C., drug loading: 10%).
Figure 26:
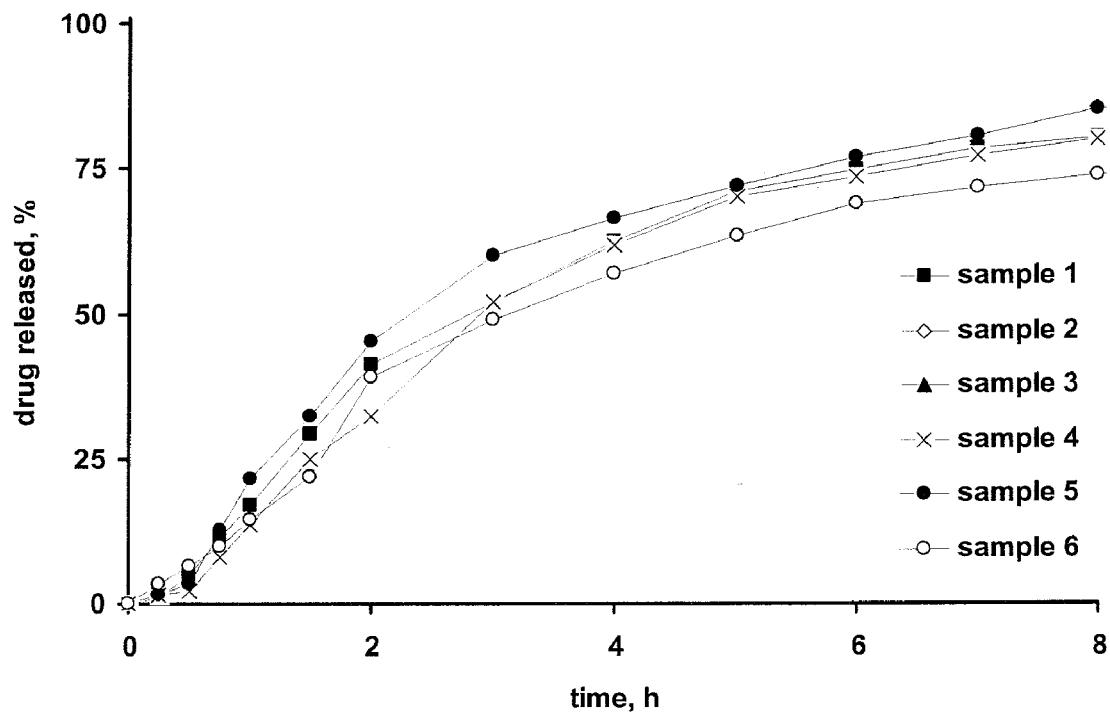
FIG. 26 shows the effects of Diltiazem-HCl release in phosphate buffer pH 7.4 from single pellets, coated with Aquacoat® ECD/Kollicoat® IR 95/05 blends with a coating level of 15% (curing for 1 day at 60° C., drug loading: 10%).

FIGS. 25-26 show the effects of Diltiazem-HCl release in 0.1M HCl from single pellets, coated with Aquacoat® ECD/Kollicoat® IR 95/05 blends with a coating level of 15% (curing for 1 day 60° C., drug loading: 10%).

Figure 28A:
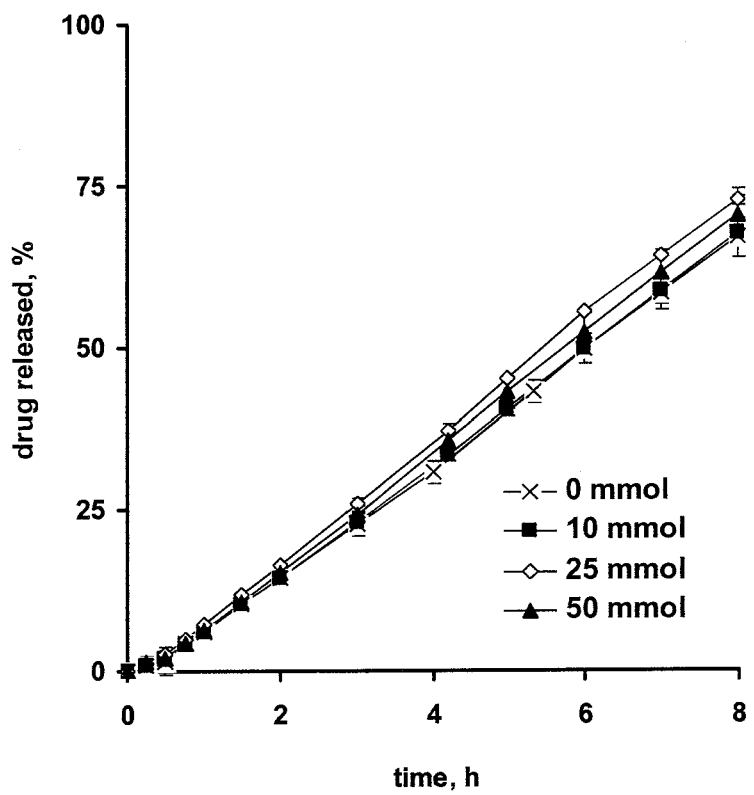
FIGS. 28(a)-28(b) show the importance of the calcium ion concentration in the release medium on theophylline release in 0.1M HCl (A) and in water (B) from pellets, coated with Aquacoat® ECD/Kollicoat® IR 85/15 blends (coating level: 20%, curing for 1 day at 60° C.).
Figure 28B:
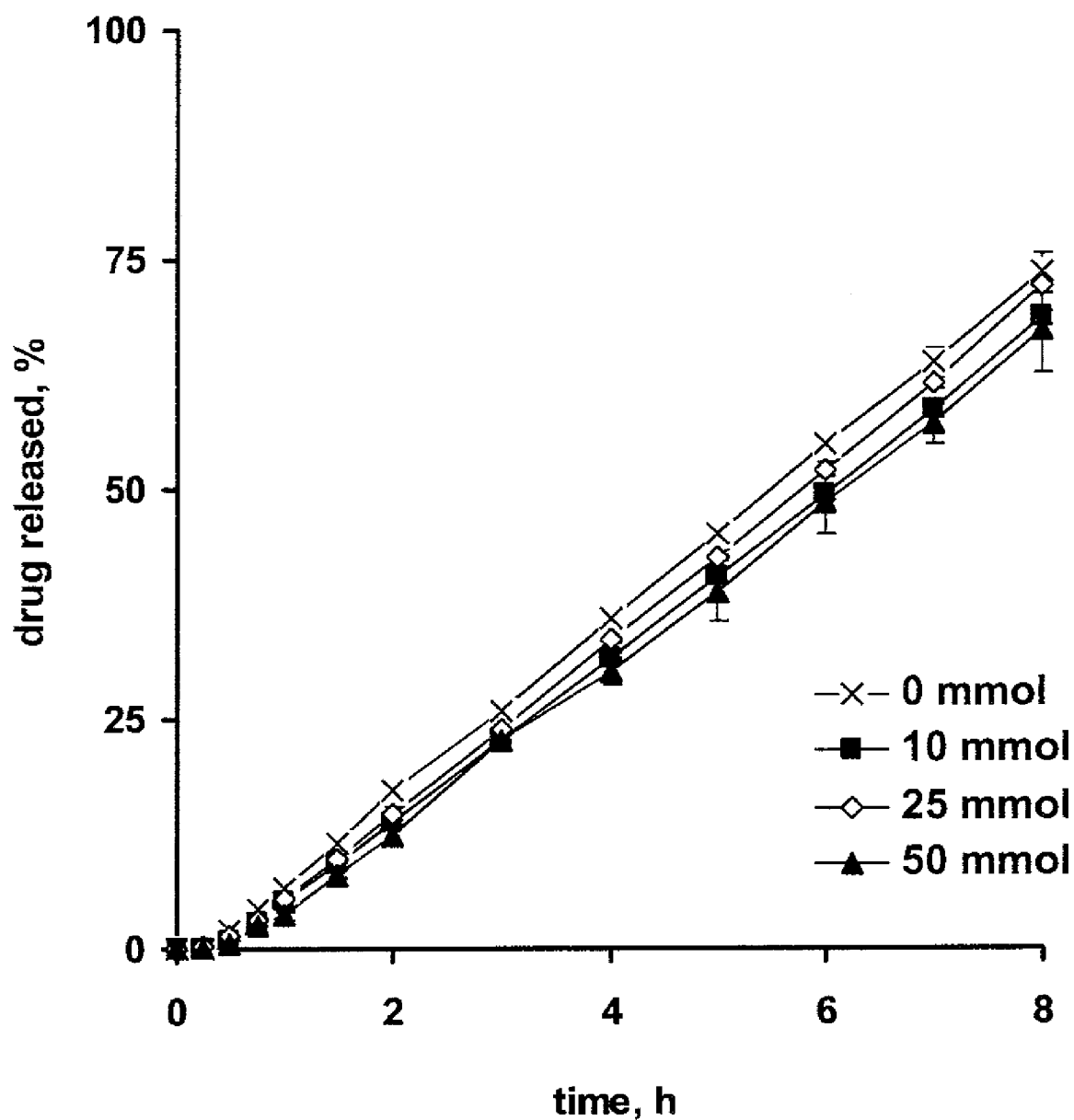
Figure 29:
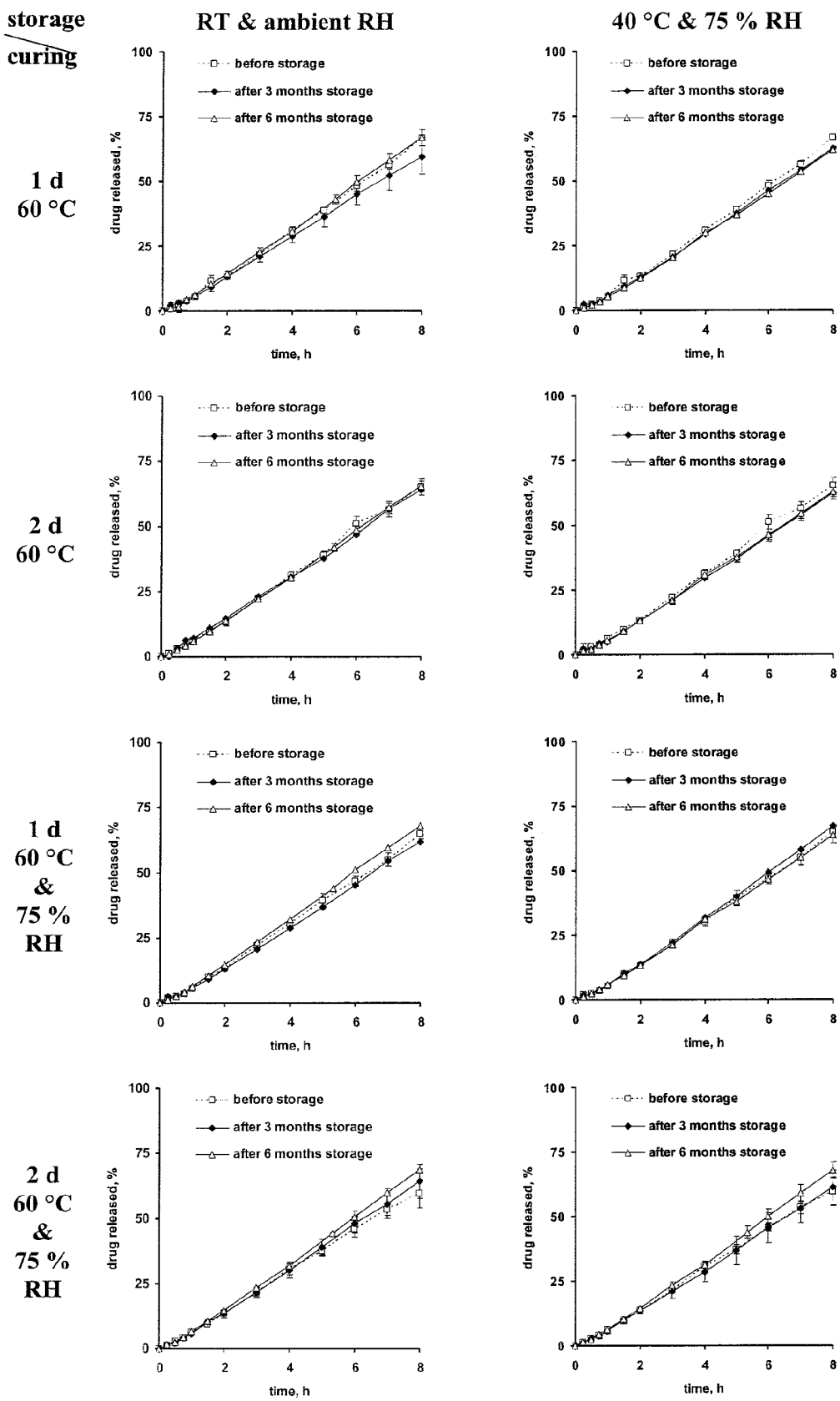
FIG. 29 shows the storage stability of pellets coated with ethylcellulose:PVA-PEG graft copolymer 85:15 blends: Theophylline release in 0.1M HCl before (dotted lines) and after 3 and 6 months storage (full lines, as indicated). The curing conditions are shown on the left, the storage conditions at the top (coating level=20%).
Figure 30:
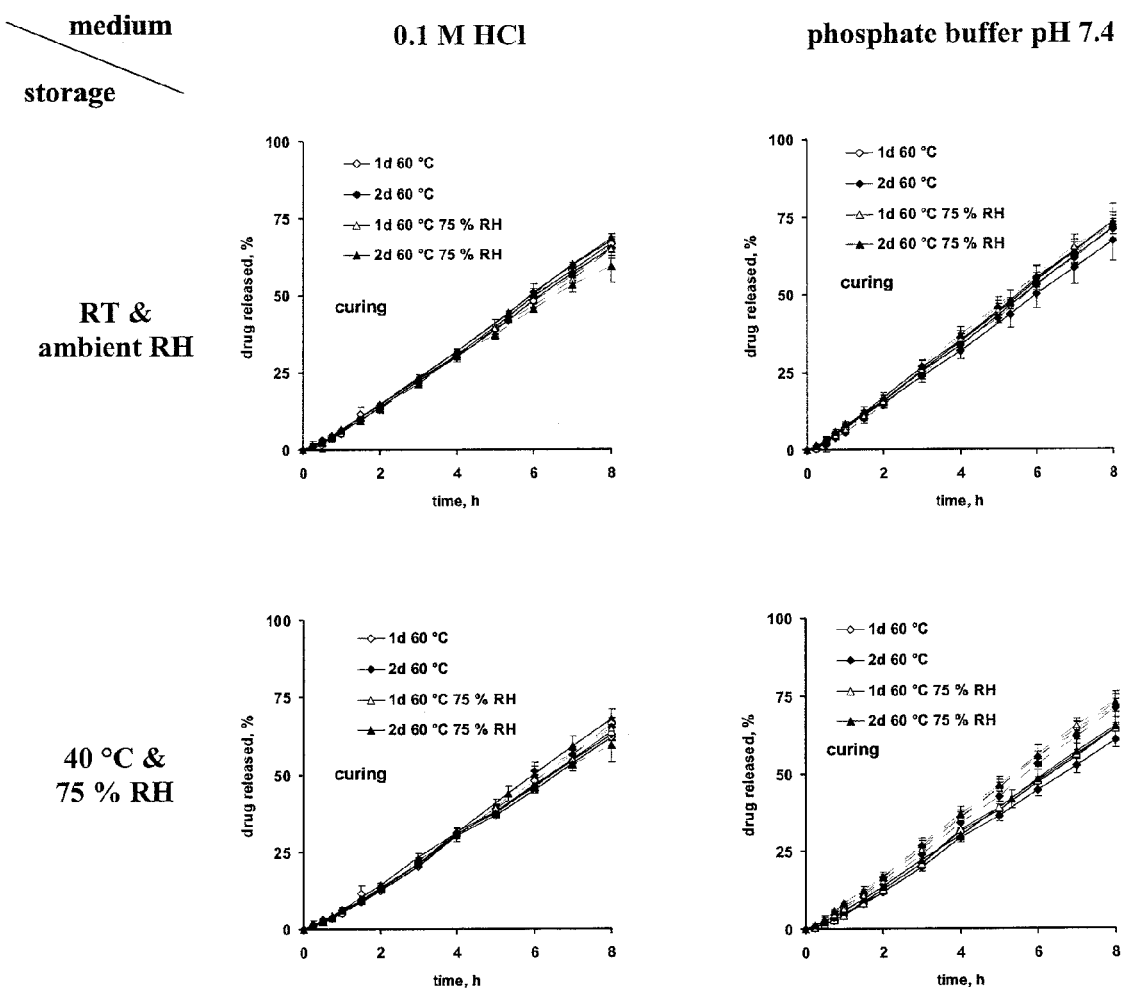
FIG. 30 shows the importance of the curing conditions (indicated in the diagrams) for theophylline release from pellets coated with ethylcellulose:PVA-PEG graft copolymer 85:15 blends before (dotted lines) and after 6 months storage (full lines) at different temperatures and relative humidity's (as indicated on the left) in 0.1M HCL or phosphate buffer pH 7.4 (as indicated at the top) (coating level=20%).
Figure 31:
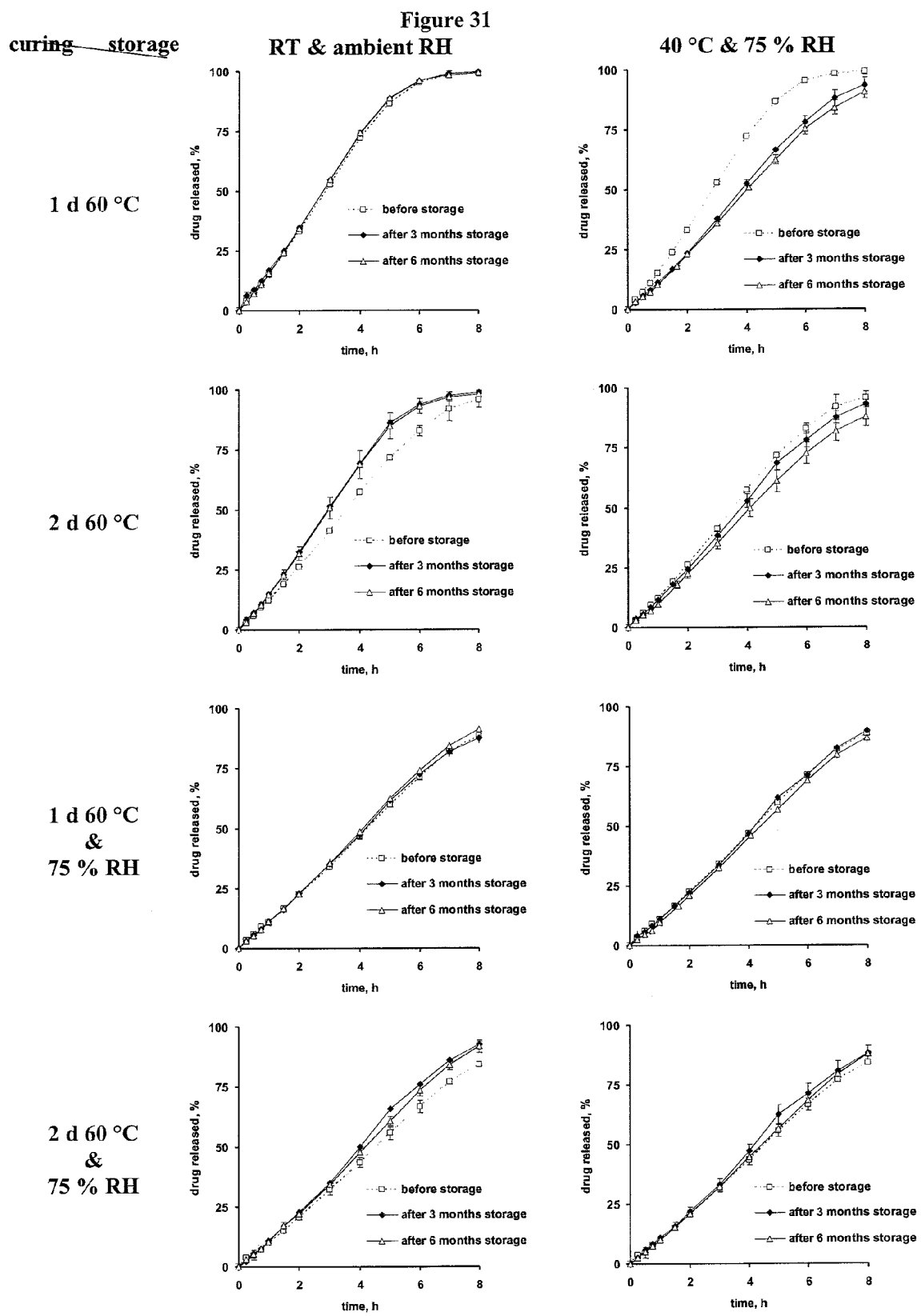
FIG. 31 shows the storage stability of pellets coated with ethylcellulose:carrageenan 90:10 blends: Theophylline release in 0.1M HCl before (dotted curves) and after 3 and 6 months storage (full curves, as indicated). The curing conditions are shown on the left, the storage conditions at the top (coating level=20%).
Figure 32:
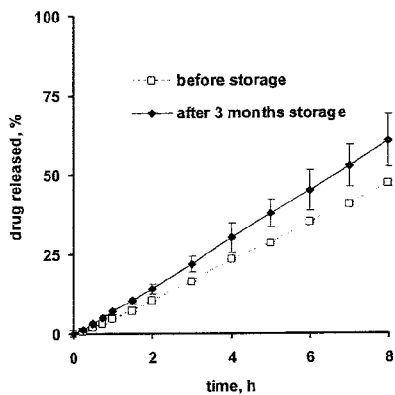
FIG. 32 shows the storage stability of pellets coated with ethylcellulose:carrageenan 95:5 blends: Theophylline release in phosphate buffer pH 7.4 before (dotted curves) and after 3 months storage (full curves, as indicated). The curing conditions are shown on the left, the storage conditions at the top (coating level=20%).
Figure 32:
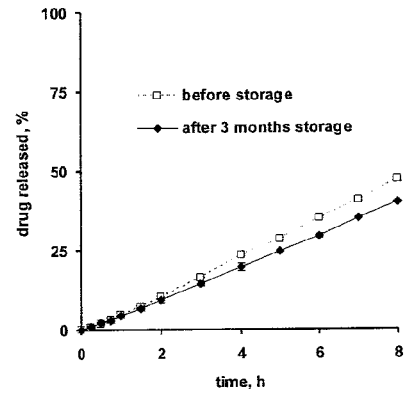
Figure 32:
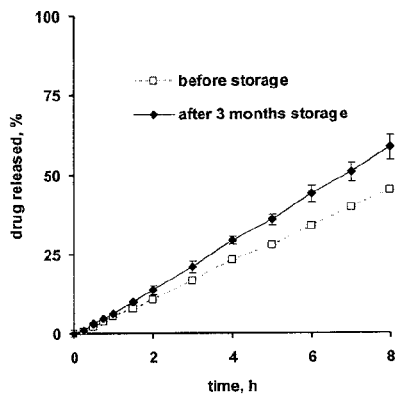
Figure 32:
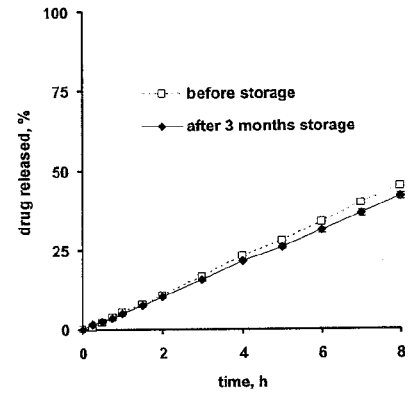
Figure 32:
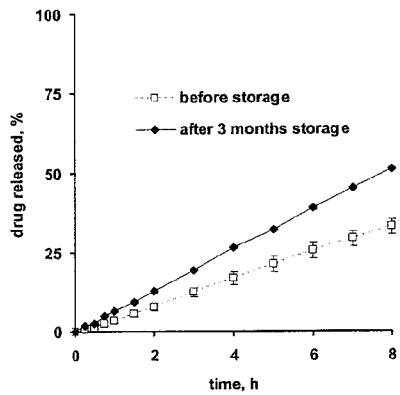
Figure 32:
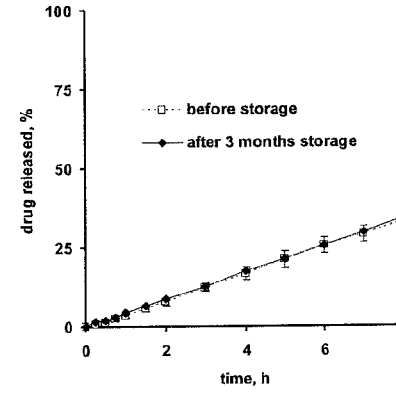
Figure 32:
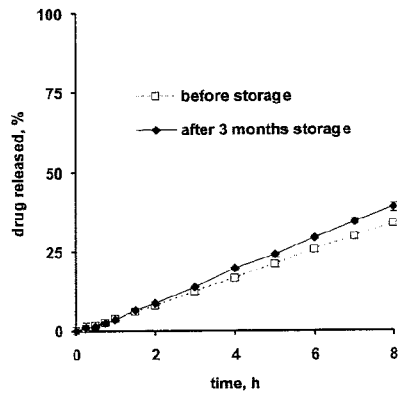
Figure 32:
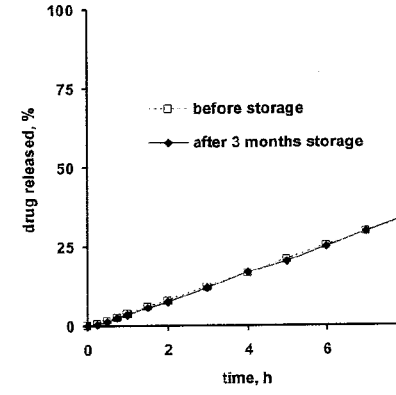
Figure 33:
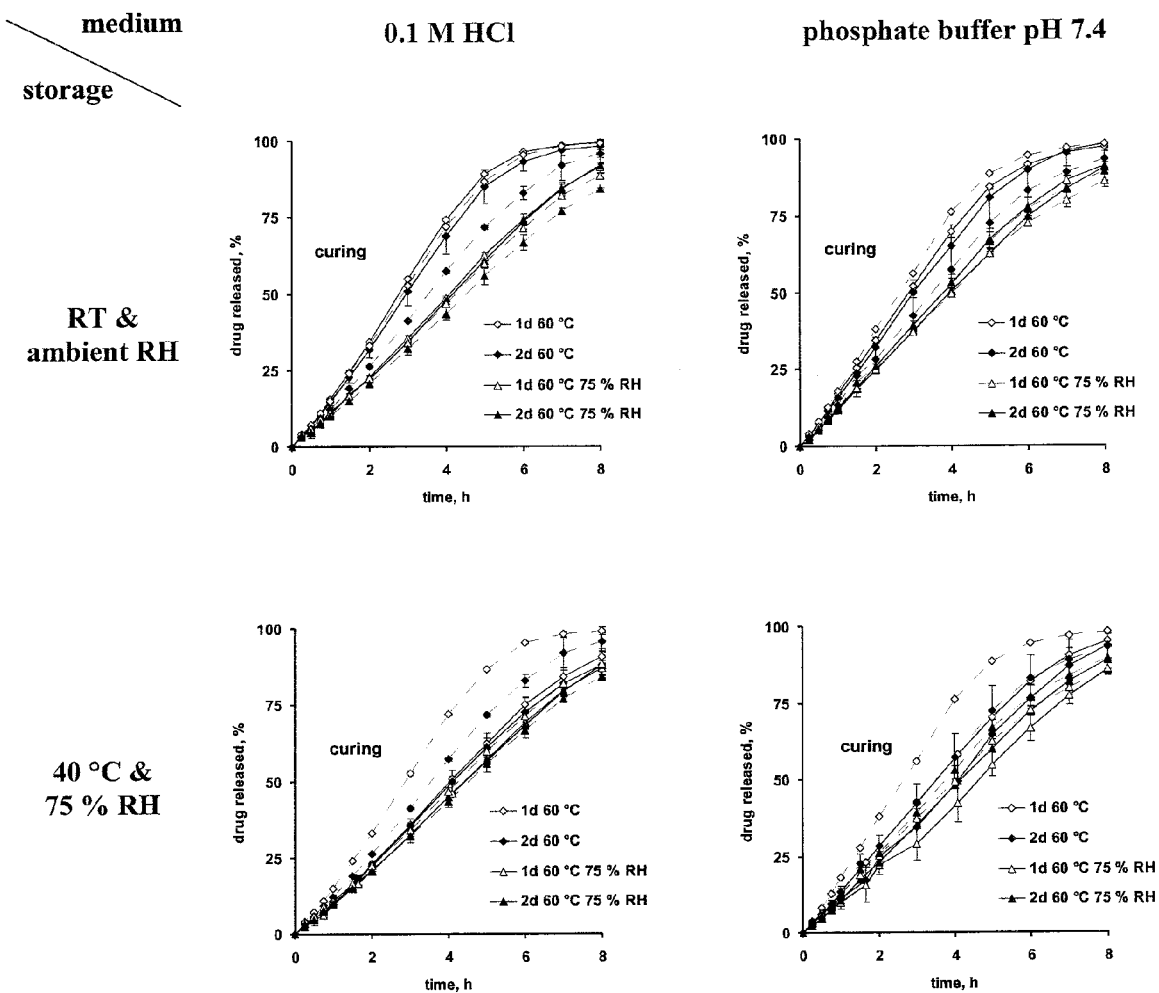
FIG. 33 shows the importance of the curing conditions (indicated in the diagrams) for theophylline release from pellets coated with ethylcellulose:carrageenan 90:10 blends before (dotted curves) and after 6 months storage (full curves) at different temperatures and relative humidities (as indicated on the left) in 0.1M HCl or phosphate buffer pH 7.4 (as indicated at the top) (coating level=20%).
Figure 34:
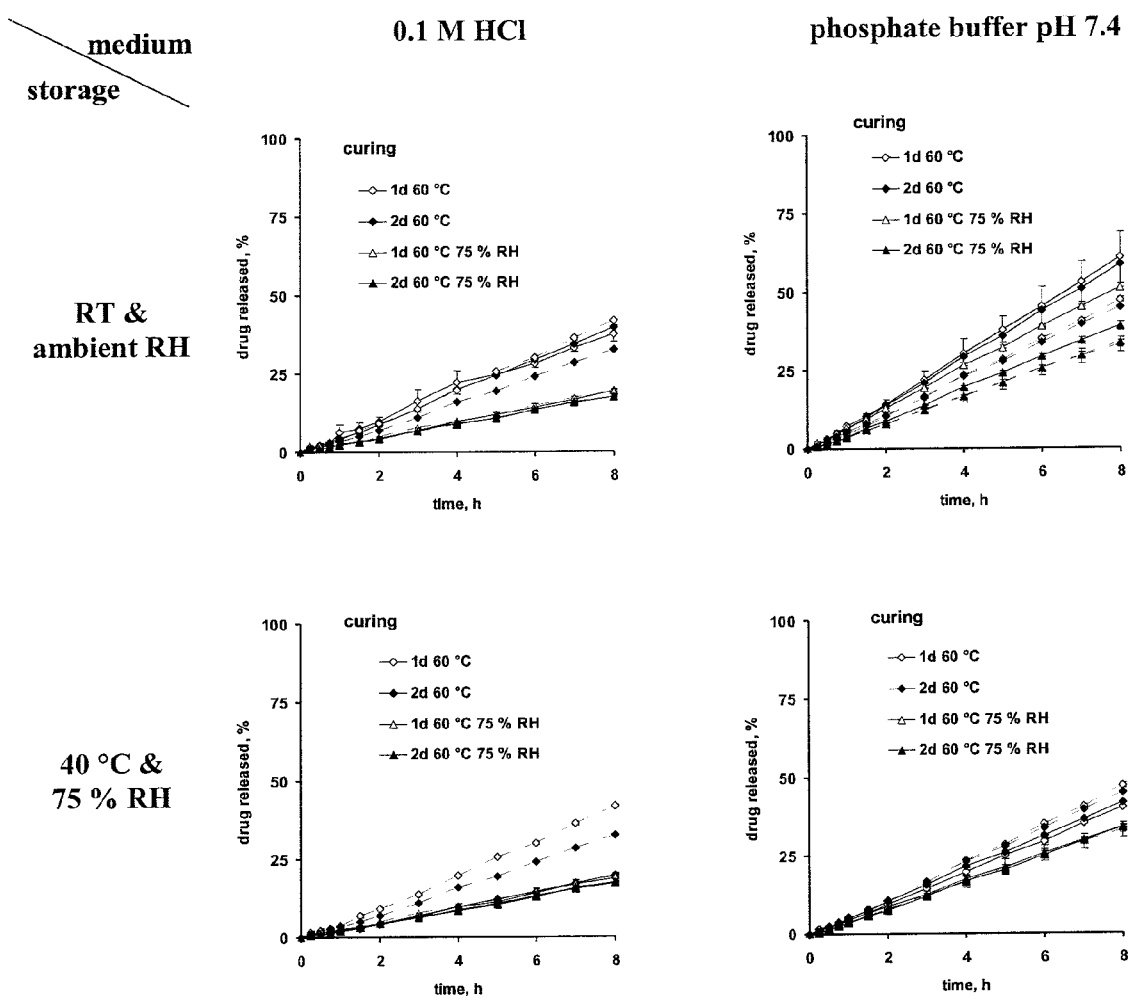
FIG. 34 shows the importance of the curing conditions (indicated in the diagrams) for theophylline release from pellets coated with ethylcellulose:carrageenan 95:5 blends before (dotted curves) and after 3 months storage (full curves) at different temperatures and relative humidity's (as indicated on the left) in 0.1M HCl or phosphate buffer pH 7.4 (as indicated at the top) (coating level=20%).

Importance of the Calcium Ion Concentration in the Release Medium on Drug Release from Theophylline-Loaded Pellets FIG. 28 shows the importance of calcium ion concentration in the release medium on drug release from theophylline-loaded pellets.

Long-Term Stability of Coatings

The major aim of this study was to identify an easy tool to improve the long term stability of polymeric film coatings applied from aqueous dispersions. Potential changes in the drug release patterns from theophylline-loaded pellets during 6 months storage under ambient as well as stress conditions ["room temperature and ambient relative humidity (RH)" and "40° C. & 75% RH"] were monitored. The pellets were cured for 1 or 2 days at 60° C. or for 1 or 2 days at 60° C. & 75% RH (followed by 1 day at 60° C. for drying). Drug release from ethylcellulose-coated pellets was measured in 0.1M HCl as well as in phosphate buffer pH 7.4.

The addition of only small amounts of poly(vinyl alcohol)-poly(ethylene glycol) graft copolymer provided stable drug release patterns under all the investigated conditions, irrespective of the type of release medium, coating level, polymer blend ratio and curing conditions.

The presence of minor percentages of propylene glycol alginate resulted in unaltered drug release kinetics during storage under ambient conditions, but decreasing theophylline release rates during storage under stress conditions as shown in FIGS. 43(a)-43(b) and 44(a)-44(b). This can be explained by the increased mobility of the ethylcellulose chains at elevated temperature and relative humidity, facilitating polymer particle coalescence. The addition of small amounts of carrageenan led to about stable theophylline release patterns in all cases (the release rate slightly decreased, slightly increased or remained unaltered). Thus, the presence of only minor amounts of appropriate additives can effectively provide long term stability of aqueous ethylcellulose-based film coatings even under stress conditions.

Figure 45A:
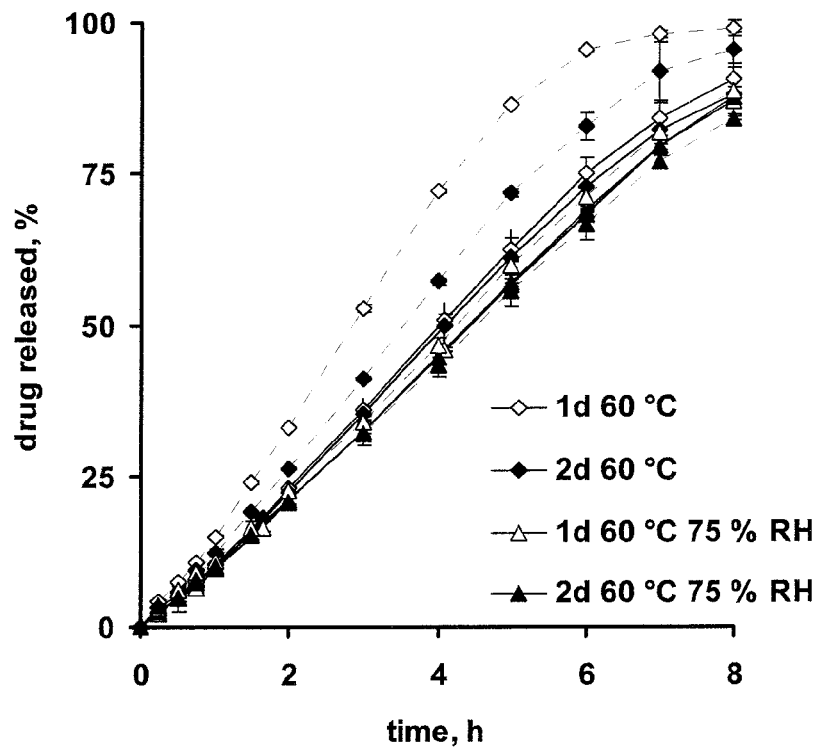
FIGS. 45(a)-45(b) show theophylline release from pellets coated with ethylcellulose:carrageenan 90:10 blends in 0.1M HCl before (dotted curves) and after (solid curves) 6 months storage at 45(a) room temperature, and 45(b) 40° C. and 75% RH (coating level: 20%, the curing conditions are indicated in the figures).
Figure 45B:
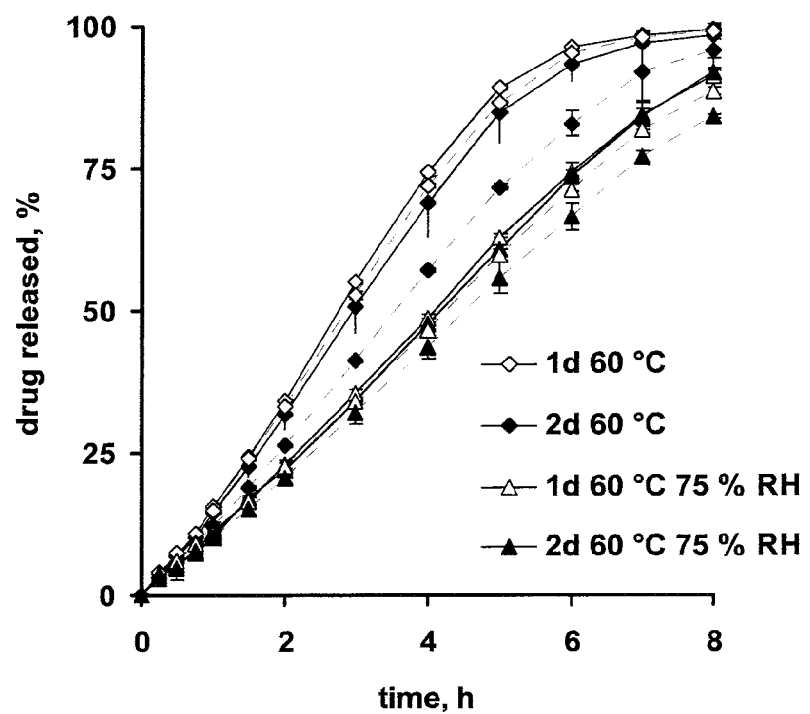

FIGS. 45(a)-45(b) show theophylline release from pellets coated with ethylcellulose:carrageenan 90:10 blends in 0.1M HCl before (dotted curves) and after (solid curves) 6 months storage at room temperature (FIG. 45(a)) and at 40° C. and 75% relative humidity (FIG. 45(b)), both with coating levels of 20% with the curing conditions indicated in the figures. The addition of small amounts of carrageenan led to substantially stable theophylline release patterns in all cases.

Figure 35A:
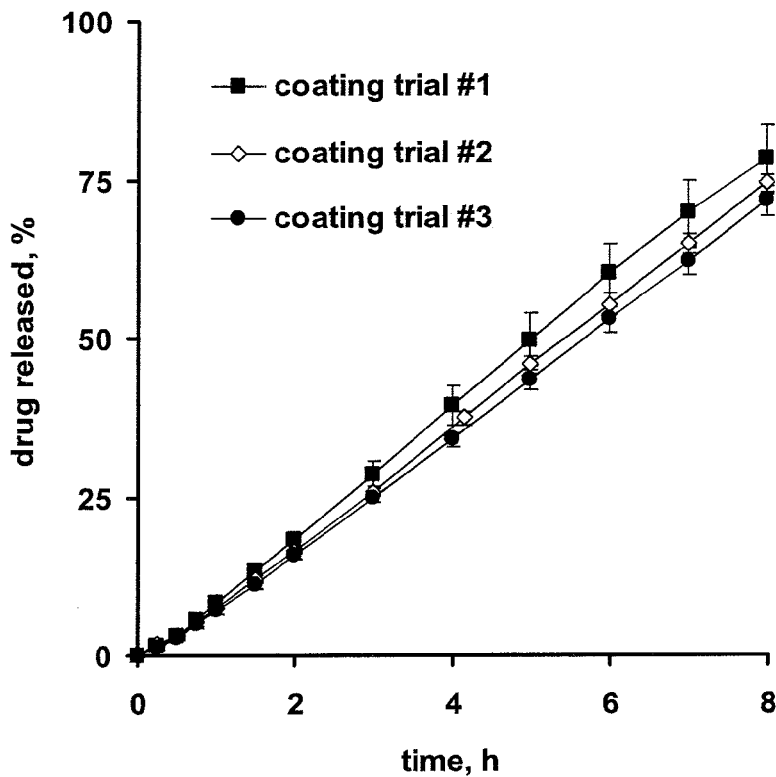
FIG. 35 shows the reproducibility of the coating process with ethylcellulose:PVA-PEG graft copolymer 85:15 blends: Theophylline release in: (a) 0.1M HCl, (b) phosphate buffer pH 7.4 from pellets coated in three different trials (the number is indicated in the diagrams) (coating level=15%; curing=1 day at 60° C.).
Figure 35B:
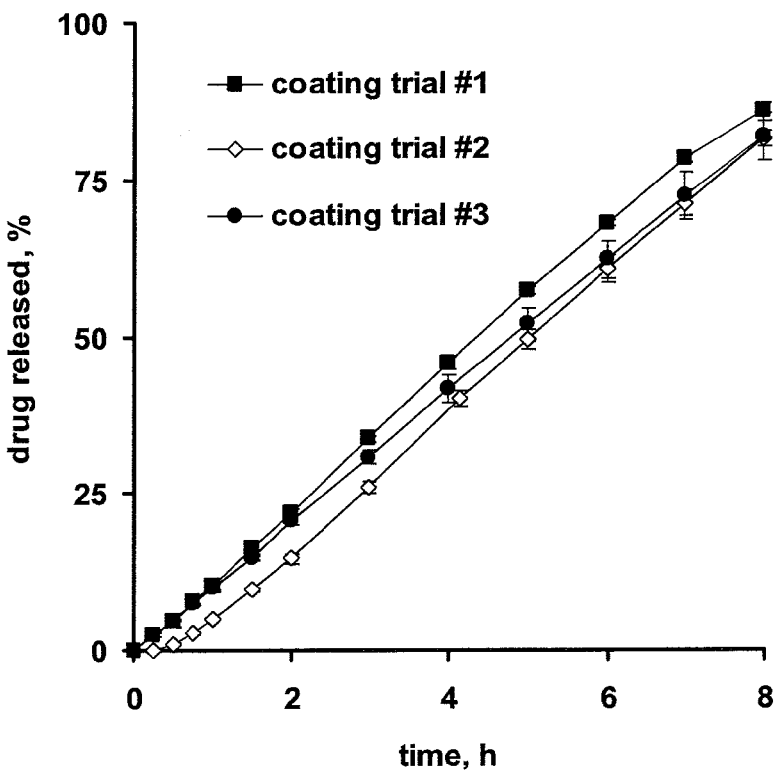

FIG. 35 shows exemplarily the release of theophylline from pellets coated with ethylcellulose:PVA-PEG graft copolymer 85:15 blends at three different days (coating trials #1-3) in 0.1M HCl and phosphate buffer pH 7.4, respectively. The coating level was 15% w/w, the pellets were cured for 1 day at 60° C. Clearly, the observed variations in the drug release kinetics were only minor in all cases (irrespective of the type of release medium), indicating the good reproducibility of the coating process with this type of polymer blends.

Figure 36A:
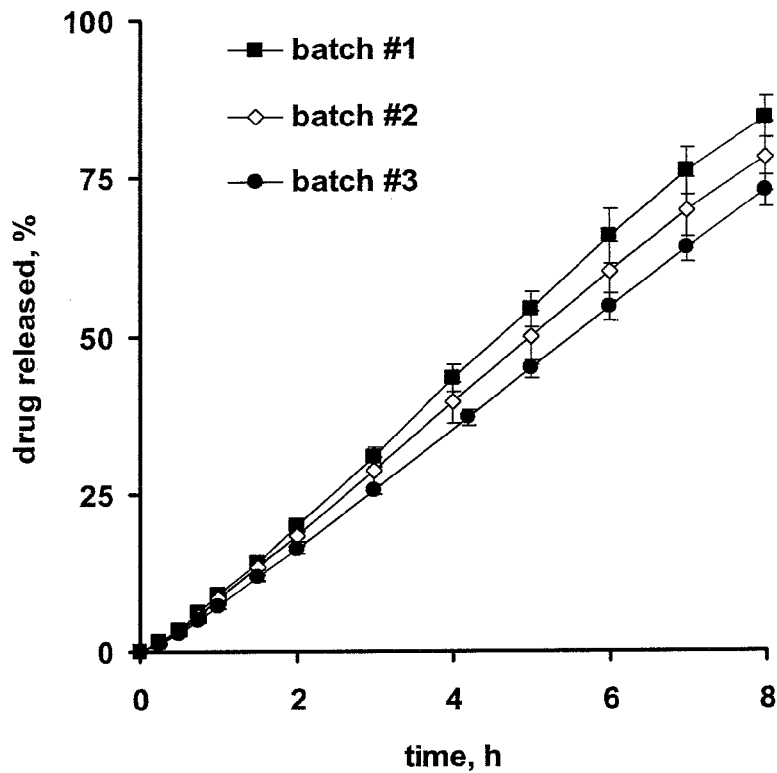
FIG. 36 shows the importance of potential batch-to-batch variability of Aquacoat® ECD used for film coating of theophylline-loaded pellets: Drug release in: (a) 0.1M HCl, (b) phosphate buffer pH 7.4 from pellets coated with three different Aquacoat® ECD batches (the number is indicated in the diagrams) (coating level=15%; ethylcellulose:PVA-PEG graft copolymer blend ratio=85:15; curing=1 day at 60° C.).
Figure 36B:
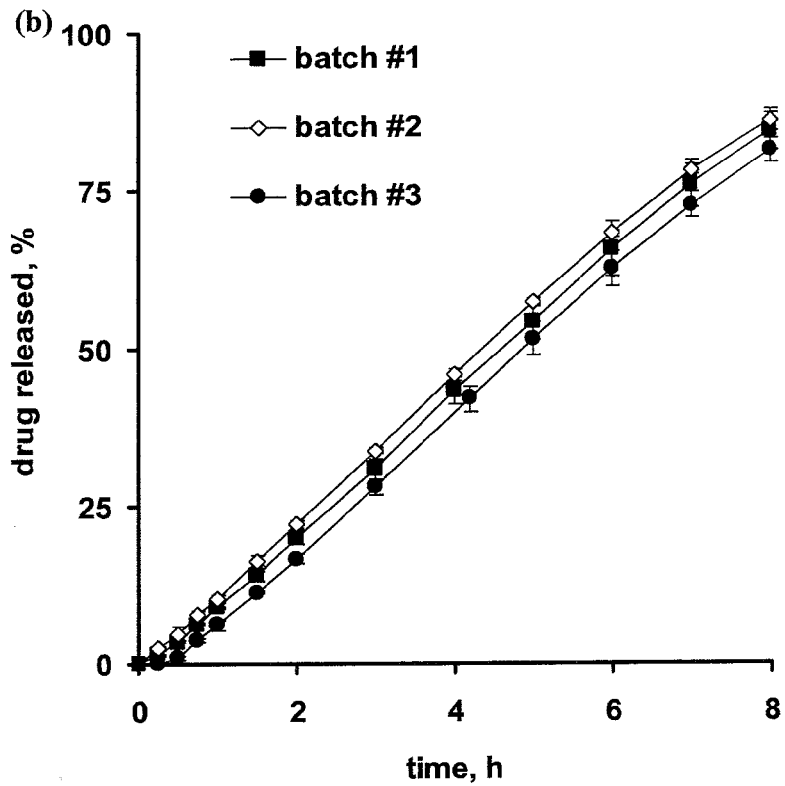

The importance of potential Aquacoat® ECD batch-to-batch variability's for the resulting drug release kinetics at low as well as at high pH from theophylline-loaded pellets coated with ethylcellulose:PVA-PEG graft copolymer 85:15 blends is illustrated in FIG. 36 (the batch numbers are indicated in the diagrams). The coating level was 15% w/w, the pellets were cured for 1 day at 60° C. Clearly, there were no significant differences in the drug release kinetics in any case.

Figure 37A:
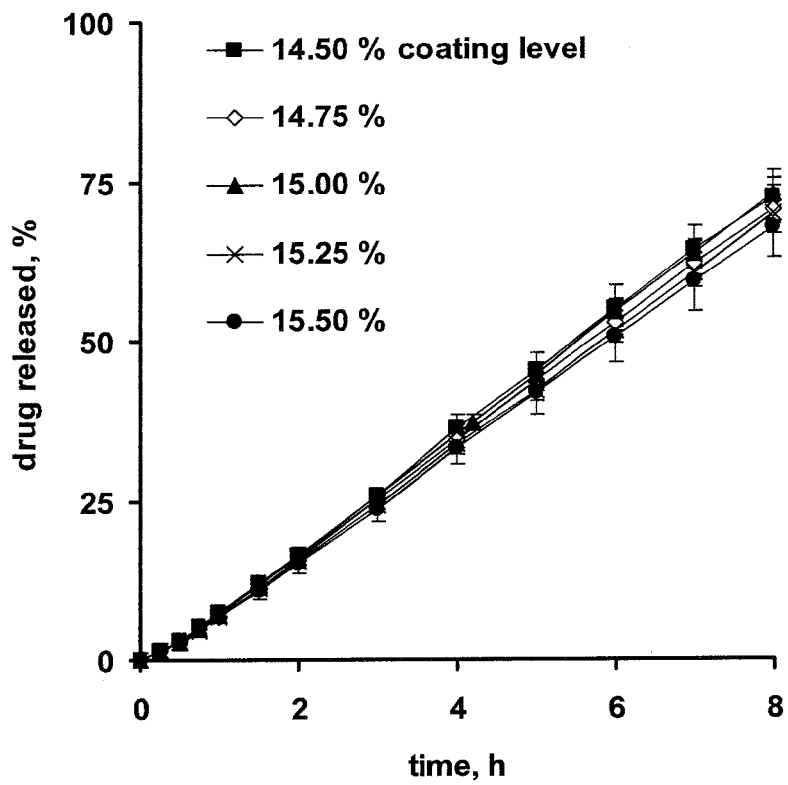
FIG. 37 shows the robustness of the coating process with ethylcellulose:PVA-PEG graft copolymer blends: Effects of slight variations in the coating level (indicated in the diagrams) on theophylline release in: (a) 0.1M HCl, (b) phosphate buffer pH 7.4 (polymer blend ratio=85:15; curing=1 day at 60° C.).
Figure 37B:
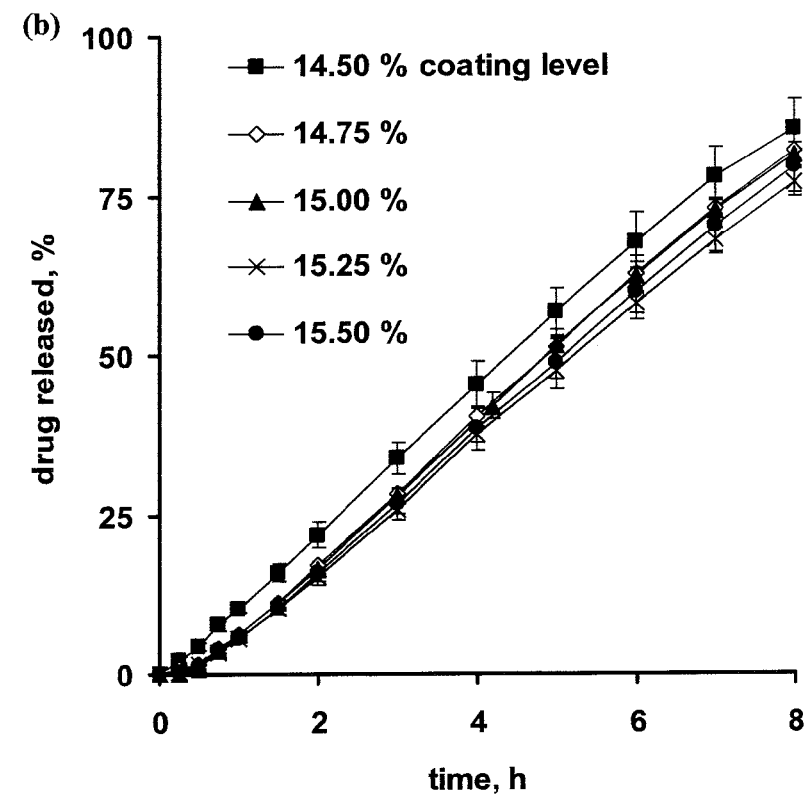

Thirdly, the sensitivity of the resulting drug release rates on slight, unintended variations in the coating level was studied (FIG. 11) The actual coating level can for instance slightly vary when using different types of fluidized bed coating apparatus, e.g. in the case of different production scales or different manufacturers (with non-identical coating chamber geometries, air flow streams etc.). The less the resulting drug release kinetics depend on such slight, unintended changes in the coating level, the more robust and easy to perform is the coating process. As it can be seen in FIG. 37, the theophylline release rate in 0.1M HCl as well as in phosphate buffer pH 7.4 only slightly decreases when increasing the (theoretical) coating level from 14.50 to 15.50% (w/w) (due to the increasing length of the diffusion pathways). This clearly indicates that this type of coating with ethylcellulose:PVA-PEG graft copolymer blends is a robust process.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A composition comprising: (i) an aqueous dispersion of at least one latex or pseudolatex comprising a water insoluble film former wherein said latex or pseudolatex water insoluble film former comprises ethylcellulose in an amount greater than or equal to 60% by weight of said composition on a dry weight basis; and (ii) a permeation enhancing agent comprising polyvinyl alcohol-polyethylene glycol copolymer; wherein said permeation enhancing agent is present in an amount of 0.5 to 30% by weight of said composition, on a dry weight basis; and wherein said composition is a sustained release coating composition.

2. The composition of claim 1, further comprises at least one plasticizer selected from the group consisting of triethyl citrate, tributyl citrate, acetyl tributylcitrate, dibutyl sebacate, glycerol, propylene glycol and polyethylene glycol.

3. The composition of claim 1, further comprises at least one plasticizer selected from the group consisting of triethyl citrate, tributyl citrate, acetyl tributylcitrate, dibutyl sebacate, glycerol, polyethylene glycol.

4. The composition of claim 1, further comprising a plasticizer in an amount of less than or equal to 50% by weight of said composition on a dry weight basis.

5. The composition of claim 1, further comprising a plasticizer in an amount of from 0.5% to 25% by weight of said composition on a dry weight basis.

6. The composition of claim 1, wherein said latex or pseudolatex water insoluble film former is present in an amount greater than or equal to 65% by weight of said composition on a dry weight basis.

7. The composition of claim 1, wherein said latex or pseudolatex water insoluble film former is present in an amount greater than or equal to 70% by weight of said composition on a dry weight basis.

8. The composition of claim 1, wherein said latex or pseudolatex water insoluble film former is present in an amount greater than or equal to 75% by weight of said composition on a dry weight basis.

9. The composition of claim 1, wherein said latex or pseudolatex water insoluble film former is present in an amount greater than or equal to 85% by weight of said composition on a dry weight basis.

10. The composition of claim 1, wherein said latex or pseudolatex water insoluble film former is present in an amount greater than or equal to 90% by weight of said composition on a dry weight basis.

11. A composition comprising: (i) at least one latex or pseudolatex comprising a water insoluble film former wherein said latex or pseudolatex water insoluble film former comprises ethylcellulose in an amount greater than or equal to 60% by weight of said composition on a dry weight basis; and (ii) a permeation enhancing agent comprising polyvinyl alcohol-polyethylene glycol copolymer; wherein said permeation enhancing agent is present in an amount of 0.5 to 30% by weight of said composition, on a dry weight basis; and wherein said composition is a sustained release coating composition.

12. The composition of claim 11, wherein said permeation enhancing agent is present in an amount of 0.5% to 20% by weight of said composition.

13. The composition of claim 11, wherein said permeation enhancing agent is present in an amount of 0.5% to 15% by weight of said composition.

14. The composition of claim 11, wherein said permeation enhancing agent is present in an amount of 0.5% to 10% by weight of said composition.

15. The composition of claim 11, wherein said permeation enhancing agent is present in an amount of 0.5% to 5% by weight of said composition.

16. The composition of claim 11, wherein said permeation enhancing agent is present in an amount of 0.5% to 3% by weight of said composition.

17. The composition of claim 11, wherein said permeation enhancing agent is present in an amount of 0.5% to 1% by weight of said composition.

18. The composition of claim 11, wherein said permeation enhancing agent is present in an amount of 0.5% to 25% by weight of said composition.

19. The composition of claim 11, wherein said latex or pseudolatex water insoluble film former is present in an amount greater than or equal to 65% by weight of said composition on a dry weight basis.

20. The composition of claim 11, wherein said latex or pseudolatex water insoluble film former is present in an amount greater than or equal to 70% by weight of said composition on a dry weight basis.

21. The composition of claim 11, wherein said latex or pseudolatex water insoluble film former is present in an amount greater than or equal to 75% by weight of said composition on a dry weight basis.

22. The composition of claim 11, wherein said latex or pseudolatex water insoluble film former is present in an amount greater than or equal to 85% by weight of said composition on a dry weight basis.

23. The composition of claim 11, wherein said latex or pseudolatex water insoluble film former is present in an amount greater than or equal to 90% by weight of said composition on a dry weight basis.

24. A film comprising the composition of claim 11.

25. A pellet comprising a substrate coated with the film of claim 24.

26. A tablet comprising a substrate coated with the film of claim 24.

27. A capsule comprising a substrate coated with the film of claim 24.

28. A capsule as claimed in claim 27, wherein the capsule is a soft capsule.

29. A capsule as claimed in claim 27, wherein the capsule is a hard capsule.

30. The composition of claim 11, further comprises at least one plasticizer selected from the group consisting of triethyl citrate, tributyl citrate, acetyl tributylcitrate, dibutyl sebacate, glycerol, propylene glycol and polyethylene glycol.

31. The composition of claim 11, further comprises at least one plasticizer selected from the group consisting of triethyl citrate, tributyl citrate, acetyl tributylcitrate, dibutyl sebacate, glycerol, polyethylene glycol.

32. The composition of claim 11, further comprising a plasticizer in an amount of less than or equal to 50% by weight of said composition on a dry weight basis.

33. The composition of claim 11, further comprising a plasticizer in an amount of from 0.5% to 25% by weight of said composition on a dry weight basis.

34. A coated substrate comprising a substrate and a coating comprising the composition of claim 11.

35. The coated substrate of claim 34, wherein said coated substrate has a lower diffusivity as compared to a coated substrate of the same coating composition and a substrate prepared under low humidity coating and low humidity curing conditions.

36. The coated substrate of claim 34, wherein the composition of claim 11 further comprises a plasticizer in an amount of less than or equal to 50% by weight of said composition on a dry weight basis.

* * * * *